United States Patent
Berner, Jr. et al.

(10) Patent No.: US 12,263,012 B2
(45) Date of Patent: Apr. 1, 2025

(54) ATHLETIC OR OTHER PERFORMANCE SENSING SYSTEMS

(71) Applicant: NIKE, Inc., Beaverton, OR (US)

(72) Inventors: William E. Berner, Jr., Portland, OR (US); Albert Shum, Portland, OR (US); Charles W. Case, Lake Oswego, OR (US); Allan M. Schrock, Portland, OR (US); James A. Niegowski, Portland, OR (US); William F. Rauchholz, Portland, OR (US)

(73) Assignee: NIKE, Inc., Beaverton, OR (US)

(*) Notice: Subject to any disclaimer, the term of this patent is extended or adjusted under 35 U.S.C. 154(b) by 0 days.

(21) Appl. No.: 18/387,328

(22) Filed: Nov. 6, 2023

(65) Prior Publication Data
US 2024/0065627 A1    Feb. 29, 2024

Related U.S. Application Data

(63) Continuation of application No. 16/356,375, filed on Mar. 18, 2019, now Pat. No. 11,925,477, which is a
(Continued)

(51) Int. Cl.
| | |
|---|---|
| *A61B 5/00* | (2006.01) |
| *A43B 3/00* | (2022.01) |
| *A43B 3/34* | (2022.01) |
| *A43B 13/00* | (2006.01) |
| *A61B 5/11* | (2006.01) |

(Continued)

(52) U.S. Cl.
CPC .......... *A61B 5/6807* (2013.01); *A43B 3/0031* (2013.01); *A43B 3/34* (2022.01); *A43B 13/00* (2013.01); *A61B 5/1112* (2013.01); *G01C 22/006* (2013.01); *G06F 1/163* (2013.01); *A63B 24/0062* (2013.01)

(58) Field of Classification Search
CPC ......... G01C 22/006; A43B 3/34; A43B 13/00; A43B 3/0031; A61B 5/1112; A61B 5/6807; G06F 1/163; A63B 24/0062
See application file for complete search history.

(56) References Cited

U.S. PATENT DOCUMENTS

| | | |
|---|---|---|
| 847,825 A | 3/1907 | Rogers |
| 1,169,999 A | 2/1916 | Richards |

(Continued)

FOREIGN PATENT DOCUMENTS

| | | |
|---|---|---|
| CN | 1093247 A | 10/1994 |
| CN | 1545154 A | 11/2004 |

(Continued)

OTHER PUBLICATIONS

Article, "adidas and Polar Introduce the World's First Completely Integrated Training System", www.adidas-Polar.com.
(Continued)

*Primary Examiner* — Congvan Tran
(74) *Attorney, Agent, or Firm* — Banner & Witcoff, Ltd.

(57) ABSTRACT

Articles of footwear and other devices include modules, e.g., for sensing physical and/or physiological characteristics associated with use of the footwear or other devices. Such devices may include an authentication or activation system for providing power or otherwise determining the connection of a sensor in the article of footwear.

18 Claims, 23 Drawing Sheets

Related U.S. Application Data continuation of application No. 15/676,491, filed on Aug. 14, 2017, now Pat. No. 10,251,601, which is a continuation of application No. 14/491,376, filed on Sep. 19, 2014, now Pat. No. 9,782,125, which is a continuation of application No. 13/958,545, filed on Aug. 3, 2013, now Pat. No. 8,857,078, which is a continuation of application No. 13/229,967, filed on Sep. 12, 2011, now Pat. No. 8,499,476, which is a continuation of application No. 12/605,811, filed on Oct. 26, 2009, now Pat. No. 8,015,732, which is a continuation of application No. 11/416,458, filed on May 3, 2006, now Pat. No. 7,607,243.

(51) Int. Cl.
*G01C 22/00* (2006.01)
*G06F 1/16* (2006.01)
*A63B 24/00* (2006.01)

(56) References Cited

U.S. PATENT DOCUMENTS

| | | |
|---|---|---|
| 1,170,767 A | 2/1916 | Lott |
| 1,291,968 A | 1/1919 | McEldowney |
| 1,559,165 A | 10/1925 | Hammond |
| 1,851,491 A | 3/1932 | Brown |
| 2,237,675 A | 4/1941 | Lazrus |
| 2,240,993 A | 5/1941 | Lazrus |
| 2,255,999 A | 9/1941 | Kuehner |
| 2,629,981 A | 3/1953 | Melik-Minassiantz |
| 2,653,442 A | 9/1953 | Kupchick |
| 2,749,634 A | 6/1956 | Billett et al. |
| 3,009,381 A | 11/1961 | Rapata |
| 3,034,189 A | 5/1962 | Twentier |
| 3,076,843 A | 2/1963 | Stacey |
| 3,208,238 A | 9/1965 | Spitzer |
| 3,421,341 A | 1/1969 | Hodge |
| 3,668,890 A | 6/1972 | Broido |
| 3,677,450 A | 7/1972 | Hodgson |
| 3,769,726 A | 11/1973 | Spence |
| 3,786,391 A | 1/1974 | Mathauser |
| 3,983,690 A | 10/1976 | McClintock |
| 4,048,796 A | 9/1977 | Sasaki |
| 4,055,755 A | 10/1977 | Nakamura et al. |
| 4,059,956 A | 11/1977 | Maeda et al. |
| 4,064,688 A | 12/1977 | Sasaki et al. |
| 4,090,353 A | 5/1978 | Maeda et al. |
| 4,120,036 A | 10/1978 | Maeda et al. |
| 4,139,837 A | 2/1979 | Liljenwall et al. |
| 4,198,772 A | 4/1980 | Furutu |
| 4,207,479 A | 6/1980 | Yamamoto et al. |
| 4,247,929 A | 1/1981 | Sasaki et al. |
| 4,255,802 A | 3/1981 | Ogawa |
| 4,257,115 A | 3/1981 | Hatuse et al. |
| 4,257,117 A | 3/1981 | Besson |
| 4,300,204 A | 11/1981 | Maeda et al. |
| 4,322,833 A | 3/1982 | Husted |
| 4,372,060 A | 2/1983 | Adamik |
| 4,402,147 A | 9/1983 | Wu |
| 4,466,204 A | 8/1984 | Wu |
| 4,477,797 A | 10/1984 | Nakagiri |
| 4,510,704 A | 4/1985 | Johnson |
| 4,571,680 A | 2/1986 | Wu |
| 4,578,769 A | 3/1986 | Frederick |
| 4,611,368 A | 9/1986 | Battersby |
| 4,630,383 A | 12/1986 | Gamm |
| 4,638,579 A | 1/1987 | Gamm |
| 4,649,552 A | 3/1987 | Yukawa |
| 4,671,671 A | 6/1987 | Suetaka |
| 4,697,359 A | 10/1987 | Balbinot |
| 4,697,363 A | 10/1987 | Gamm |
| 4,703,445 A | 10/1987 | Dassler |
| 4,770,008 A | 9/1988 | Yamaura |
| 4,771,394 A | 9/1988 | Cavanagh |
| 4,780,968 A | 11/1988 | Bragagnolo |
| 4,974,429 A | 12/1990 | Ferrara |
| 5,086,574 A | 2/1992 | Bacchiocchi |
| 5,088,070 A | 2/1992 | Shiff |
| 5,285,586 A | 2/1994 | Goldston et al. |
| 5,303,485 A | 4/1994 | Goldston et al. |
| 5,357,597 A | 10/1994 | Aparicio, IV et al. |
| 5,357,697 A | 10/1994 | Lin |
| 5,369,896 A | 12/1994 | Frachey et al. |
| 5,373,651 A | 12/1994 | Wood |
| 5,396,720 A | 3/1995 | Hwang et al. |
| 5,410,784 A | 5/1995 | Katz |
| 5,471,405 A | 11/1995 | Marsh |
| 5,487,053 A | 1/1996 | Beiswenger et al. |
| 5,490,338 A | 2/1996 | Hwang et al. |
| 5,500,635 A | 3/1996 | Mott |
| 5,546,681 A | 8/1996 | Goldston et al. |
| 5,583,776 A | 12/1996 | Levi et al. |
| 5,592,759 A | 1/1997 | Cox |
| 5,623,772 A | 4/1997 | Sunderland et al. |
| 5,640,786 A | 6/1997 | Buyayez |
| 5,640,857 A | 6/1997 | Halik |
| 5,644,858 A | 7/1997 | Bemis |
| 5,689,867 A | 11/1997 | Katz |
| 5,692,324 A | 12/1997 | Goldston et al. |
| 5,704,706 A | 1/1998 | Goldston et al. |
| 5,722,260 A | 3/1998 | Mangano |
| 5,724,265 A | 3/1998 | Hutchings |
| 5,732,486 A | 3/1998 | Rapisarda |
| 5,758,443 A | 6/1998 | Pedrazzini |
| 5,765,300 A | 6/1998 | Kianka |
| 5,775,005 A | 7/1998 | McClelland |
| 5,775,011 A | 7/1998 | Reitano, Jr. |
| 5,790,477 A | 8/1998 | Hauke |
| 5,866,987 A | 2/1999 | Wut |
| 5,921,008 A | 7/1999 | Ruff |
| 5,940,349 A | 8/1999 | Stewart |
| 5,955,667 A | 9/1999 | Fyfe |
| 5,983,529 A | 11/1999 | Serna |
| 6,000,149 A | 12/1999 | Pomerantz |
| 6,013,007 A | 1/2000 | Root et al. |
| 6,017,128 A | 1/2000 | Goldston et al. |
| 6,018,705 A | 1/2000 | Gaudet et al. |
| 6,052,654 A | 4/2000 | Gaudet et al. |
| 6,077,193 A | 6/2000 | Buhler et al. |
| 6,085,449 A | 7/2000 | Tsui |
| 6,122,340 A | 9/2000 | Darley et al. |
| 6,122,846 A | 9/2000 | Gray et al. |
| 6,158,884 A | 12/2000 | Lebby et al. |
| 6,195,921 B1 | 3/2001 | Truong |
| 6,215,985 B1 | 4/2001 | Tolvanen |
| 6,243,870 B1 | 6/2001 | Graber |
| 6,312,361 B1 | 11/2001 | Hayes |
| 6,324,053 B1 | 11/2001 | Kamijo |
| 6,331,965 B1 | 12/2001 | Sato et al. |
| 6,359,838 B1 | 3/2002 | Taylor |
| 6,386,041 B1 | 5/2002 | Yang |
| 6,430,843 B1 | 8/2002 | Potter et al. |
| 6,446,466 B1 | 9/2002 | Headley |
| 6,470,601 B1 | 10/2002 | Zane |
| 6,477,117 B1 | 11/2002 | Narayanaswami et al. |
| 6,510,988 B1 | 1/2003 | Kraus |
| 6,522,534 B1 | 2/2003 | Wu |
| 6,525,997 B1 | 2/2003 | Narayanaswami et al. |
| 6,527,610 B1 | 3/2003 | Hornsby et al. |
| 6,535,941 B1 | 3/2003 | Kruse |
| 6,536,139 B2 | 3/2003 | Darley et al. |
| 6,556,222 B1 | 4/2003 | Narayanaswami |
| 6,560,903 B1 | 5/2003 | Darley |
| 6,585,622 B1 | 7/2003 | Shum et al. |
| 6,589,630 B1 | 7/2003 | Crow |
| 6,603,708 B2 | 8/2003 | Tamagawa et al. |
| 6,619,835 B2 | 9/2003 | Kita |
| 6,639,791 B2 | 10/2003 | Su |
| 6,701,583 B1 | 3/2004 | McCullough |
| 6,714,486 B2 | 3/2004 | Biggs |
| 6,728,166 B2 | 4/2004 | Grupp |
| 6,733,329 B2 | 5/2004 | Yang |
| 6,736,759 B1 | 5/2004 | Stubbs et al. |

(56) References Cited

U.S. PATENT DOCUMENTS

| | | |
|---|---|---|
| 6,743,030 B2 | 6/2004 | Lin et al. |
| 6,745,069 B2 | 6/2004 | Nissilä et al. |
| 6,760,003 B1 | 7/2004 | Sase |
| 6,763,410 B2 | 7/2004 | Yu |
| 6,773,192 B1 | 8/2004 | Chao |
| 6,788,200 B1 | 9/2004 | Jamel et al. |
| 6,801,476 B2 | 10/2004 | Gilmour |
| 6,804,977 B1 | 10/2004 | Grabelle |
| 6,807,753 B2 | 10/2004 | Steszyn et al. |
| 6,807,869 B2 | 10/2004 | Farringdon et al. |
| 6,808,462 B2 | 10/2004 | Snyder et al. |
| 6,816,440 B2 | 11/2004 | Born et al. |
| D502,216 S | 2/2005 | Chen |
| 6,876,947 B1 | 4/2005 | Darley et al. |
| 6,882,955 B1 | 4/2005 | Ohlenbusch et al. |
| 6,895,261 B1 | 5/2005 | Palamides |
| 6,963,468 B2 | 11/2005 | Chang et al. |
| 6,967,903 B2 | 11/2005 | Guanter |
| 6,970,157 B2 | 11/2005 | Siddeeq |
| 6,977,868 B2 | 12/2005 | Brewer et al. |
| 6,980,204 B1 | 12/2005 | Hawkins et al. |
| 6,983,553 B2 | 1/2006 | Lussier et al. |
| 6,983,888 B2 | 1/2006 | Weng |
| 6,997,852 B2 | 2/2006 | Watterson et al. |
| 7,006,408 B2 | 2/2006 | Chen |
| 7,020,508 B2 | 3/2006 | Stivoric et al. |
| 7,029,193 B1 | 4/2006 | Chao |
| 7,030,735 B2 | 4/2006 | Chen |
| 7,031,226 B2 | 4/2006 | Farine |
| 7,031,228 B2 | 4/2006 | Born et al. |
| 7,035,170 B2 | 4/2006 | Narayanaswami et al. |
| 7,042,804 B2 | 5/2006 | Guanter |
| 7,057,551 B1 | 6/2006 | Vogt |
| 7,062,225 B2 | 6/2006 | White |
| 7,079,452 B2 | 7/2006 | Harrison |
| 7,081,905 B1 | 7/2006 | Raghunath |
| 7,083,296 B2 | 8/2006 | Chiang |
| 7,113,451 B1 | 9/2006 | Matthey |
| 7,177,234 B1 | 2/2007 | Paul |
| 7,221,624 B2 | 5/2007 | Harrison, Jr. |
| 7,234,010 B2 | 6/2007 | Gilmour |
| D545,896 S | 7/2007 | Qiu |
| D547,374 S | 7/2007 | Deng |
| 7,242,639 B2 | 7/2007 | Blondeau et al. |
| D553,130 S | 10/2007 | Fiorentino |
| 7,280,844 B2 | 10/2007 | Ikeda et al. |
| 7,293,332 B2 | 11/2007 | Maillard |
| 7,311,526 B2 | 12/2007 | Rohrbach et al. |
| 7,331,793 B2 | 2/2008 | Hernandez et al. |
| 7,351,066 B2 | 4/2008 | DiFonzo et al. |
| 7,603,255 B2 | 10/2009 | Case, Jr. et al. |
| 7,607,243 B2 | 10/2009 | Berner, Jr. et al. |
| 7,714,709 B1 | 5/2010 | Daniel |
| 8,015,732 B2 | 9/2011 | Berner, Jr. et al. |
| 8,943,713 B1 | 2/2015 | Eidson |
| 2002/0002863 A1 | 1/2002 | Slycke et al. |
| 2002/0116147 A1 | 8/2002 | Vock et al. |
| 2003/0009913 A1 | 1/2003 | Potter et al. |
| 2003/0097878 A1 | 5/2003 | Farringdon et al. |
| 2003/0148797 A1 | 8/2003 | Huang |
| 2003/0197678 A1 | 10/2003 | Siddeeq |
| 2003/0208382 A1 | 11/2003 | Westfall |
| 2003/0208928 A1 | 11/2003 | Steszyn et al. |
| 2003/0214885 A1 | 11/2003 | Powell et al. |
| 2004/0046692 A1 | 3/2004 | Robson et al. |
| 2004/0103000 A1 | 5/2004 | Owurowa et al. |
| 2004/0133081 A1 | 7/2004 | Teller et al. |
| 2004/0148799 A1 | 8/2004 | Lussier et al. |
| 2004/0151071 A1 | 8/2004 | Kocher |
| 2004/0163280 A1 | 8/2004 | Morris et al. |
| 2004/0177531 A1 | 9/2004 | DiBenedetto et al. |
| 2004/0198554 A1 | 10/2004 | Orr et al. |
| 2004/0216330 A1 | 11/2004 | Swigart |
| 2004/0233786 A1 | 11/2004 | Ting |
| 2004/0264301 A1 | 12/2004 | Howard et al. |
| 2005/0007337 A1 | 1/2005 | Sellen et al. |
| 2005/0016031 A1 | 1/2005 | Ruff |
| 2005/0075213 A1 | 4/2005 | Arick |
| 2005/0083315 A1 | 4/2005 | Pei |
| 2005/0108059 A1 | 5/2005 | Tay |
| 2005/0203349 A1 | 9/2005 | Nanikashvili |
| 2005/0209887 A1 | 9/2005 | Pollner |
| 2005/0227811 A1 | 10/2005 | Shum et al. |
| 2005/0228244 A1 | 10/2005 | Banet |
| 2005/0235528 A1 | 10/2005 | Tsai |
| 2005/0235539 A1 | 10/2005 | Story |
| 2005/0261609 A1 | 11/2005 | Collings et al. |
| 2006/0004303 A1 | 1/2006 | Weidenhaupt et al. |
| 2006/0010012 A1 | 1/2006 | Franzblau et al. |
| 2006/0012566 A1 | 1/2006 | Siddeeq |
| 2006/0015368 A1 | 1/2006 | Hockey |
| 2006/0022833 A1 | 2/2006 | Ferguson et al. |
| 2006/0035480 A1 | 2/2006 | Boyd et al. |
| 2006/0063980 A1 | 3/2006 | Hwang et al. |
| 2006/0064136 A1 | 3/2006 | Wang |
| 2006/0064900 A1 | 3/2006 | Aveni |
| 2006/0080137 A1 | 4/2006 | Chambers et al. |
| 2006/0080868 A1 | 4/2006 | Chi |
| 2006/0088171 A1 | 4/2006 | Yeh |
| 2006/0092177 A1 | 5/2006 | Blasko |
| 2006/0103642 A1 | 5/2006 | Hawkins et al. |
| 2006/0104046 A1 | 5/2006 | Guzman |
| 2006/0136173 A1 | 6/2006 | Case et al. |
| 2006/0140055 A1 | 6/2006 | Ehrsam et al. |
| 2006/0143645 A1 | 6/2006 | Vock et al. |
| 2006/0145663 A1 | 7/2006 | Shiff et al. |
| 2006/0156581 A1 | 7/2006 | Holden et al. |
| 2006/0168847 A1 | 8/2006 | Myers et al. |
| 2006/0170649 A1 | 8/2006 | Kosugi et al. |
| 2006/0174522 A1 | 8/2006 | Yu |
| 2006/0189218 A1* | 8/2006 | Uhari ............... G04B 37/1413 439/752 |
| 2006/0221772 A1 | 10/2006 | Vuilleumier et al. |
| 2006/0226242 A2 | 10/2006 | Kim |
| 2006/0230641 A1 | 10/2006 | Vick et al. |
| 2006/0230642 A1 | 10/2006 | Vick et al. |
| 2006/0248750 A1 | 11/2006 | Rosenberg |
| 2006/0261958 A1 | 11/2006 | Klein |
| 2006/0283050 A1 | 12/2006 | Carnes et al. |
| 2007/0016452 A1 | 1/2007 | Wilson |
| 2007/0021269 A1* | 1/2007 | Shum ................. A61B 5/0024 482/8 |
| 2007/0030442 A1 | 2/2007 | Howell et al. |
| 2007/0033717 A1 | 2/2007 | Anderson |
| 2007/0033838 A1 | 2/2007 | Luce et al. |
| 2007/0044346 A1 | 3/2007 | Ungari et al. |
| 2007/0058295 A1 | 3/2007 | Lasser |
| 2007/0064542 A1 | 3/2007 | Fukushima |
| 2007/0066088 A1 | 3/2007 | Rambosek et al. |
| 2007/0071643 A1 | 3/2007 | Hall et al. |
| 2007/0072442 A1 | 3/2007 | DiFonzo et al. |
| 2007/0073178 A1 | 3/2007 | Browning et al. |
| 2007/0080935 A1 | 4/2007 | Hanson et al. |
| 2007/0100935 A1 | 5/2007 | Miyazaki et al. |
| 2007/0104032 A1 | 5/2007 | Falkenstein et al. |
| 2007/0144040 A1 | 6/2007 | Chen |
| 2007/0208544 A1 | 9/2007 | Kulach et al. |
| 2007/0221140 A1 | 9/2007 | Warren et al. |
| 2007/0245465 A1 | 10/2007 | Neal et al. |
| 2007/0247306 A1 | 10/2007 | Case |
| 2007/0287302 A1 | 12/2007 | Lindberg et al. |
| 2008/0046179 A1 | 2/2008 | Mackintosh et al. |
| 2008/0125288 A1 | 5/2008 | Case |
| 2008/0214360 A1 | 9/2008 | Stirling et al. |
| 2008/0254944 A1 | 10/2008 | Muri et al. |
| 2008/0281168 A1* | 11/2008 | Gibson ............. A61B 5/02438 600/301 |
| 2009/0143689 A1 | 6/2009 | Berry et al. |
| 2009/0249655 A1 | 10/2009 | Portnell |
| 2010/0095209 A1 | 4/2010 | Gupta et al. |
| 2010/0210421 A1 | 8/2010 | Case, Jr. et al. |
| 2011/0269714 A1 | 11/2011 | Xiao et al. |
| 2011/0314702 A1 | 12/2011 | Berner, Jr. et al. |

(56) References Cited

U.S. PATENT DOCUMENTS

| | | | |
|---|---|---|---|
| 2012/0004046 A1 | 1/2012 | Baker | |
| 2013/0116514 A1* | 5/2013 | Kroner | A61B 5/339 |
| | | | 600/509 |
| 2013/0211204 A1* | 8/2013 | Caduff | A61B 5/14532 |
| | | | 600/300 |

FOREIGN PATENT DOCUMENTS

| | | |
|---|---|---|
| CN | 1647710 A | 8/2005 |
| CN | 2757431 Y | 2/2006 |
| DE | 29822640 U1 | 4/1999 |
| DE | 29822641 U1 | 7/1999 |
| DE | 102005014709 A1 | 10/2006 |
| EP | 0152057 A2 | 8/1985 |
| EP | 1120056 A2 | 8/2001 |
| EP | 1134555 A1 | 9/2001 |
| EP | 1362522 A1 | 11/2003 |
| GB | 2282521 A | 4/1995 |
| JP | S58186795 U | 12/1983 |
| JP | S60188101 A | 9/1985 |
| JP | H06-014803 A | 1/1994 |
| JP | 7-504602 T | 5/1995 |
| JP | 3065400 B2 | 7/2000 |
| JP | 2000236904 A | 9/2000 |
| JP | 3076843 U | 4/2001 |
| JP | 2002119498 A | 4/2002 |
| JP | 2002527124 A | 8/2002 |
| JP | 2002253301 A | 9/2002 |
| JP | 2003169702 A | 6/2003 |
| JP | 2003325201 A | 11/2003 |
| JP | 200426155 A | 1/2004 |
| JP | 2005203138 A | 7/2005 |
| JP | 2005237926 A | 9/2005 |
| JP | 2006001483 A | 1/2006 |
| JP | 62-40701 B2 | 11/2017 |
| WO | 9526652 A1 | 10/1995 |
| WO | 2005020734 A2 | 3/2005 |
| WO | 2007064735 A2 | 6/2007 |
| WO | 2009033034 A1 | 3/2009 |

OTHER PUBLICATIONS

Search Report and Written Opinion for international Application No. PCT/US2007/009919, mailing Nov. 25, 2008, 17 pages.

International Preliminary Report on Patentability for International Application No. PCT/US2007/009919, mailed Dec. 31, 2008, 10 pages.

First Office Action for Chinese Patent Application No. 200780015864.9 mailed Sep. 13, 2010.

Notice of Reasons for Rejection for Japanese patent application No. 2009-509602 mailed Jul. 7, 2011.

The Third Office Action for Chinese patent application No. 200780015864.9 mailed Apr. 20, 2012.

European office action for application No. 07776088.2 mailed Mar. 29, 2012.

Second office action for Chinese application No. 200780015864.9 mailed Aug. 1, 2011.

Notice of Reasons for Rejection for Japanese patent application No. 2009-509602 mailed Apr. 5, 2012.

European office action for application 07776088.2 mailed Oct. 23, 2012.

Chinese Patent Application No. 200780015864.9—Fourth Office Action dated Jan. 7, 2013.

Feb. 4, 2014 (US) Office Action issued in Japanese Patent Application No. 2012-277627.

Jul. 7, 2014 (US) Decision of Rejection Japanese Patent Application No. 2012-277627.

\* cited by examiner

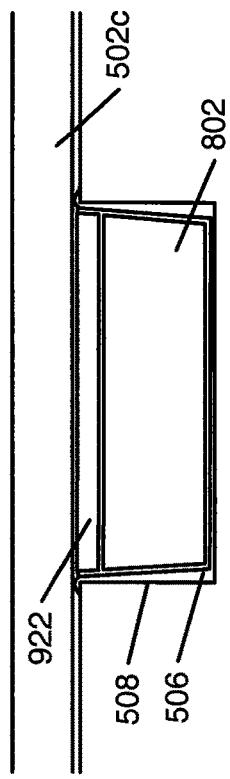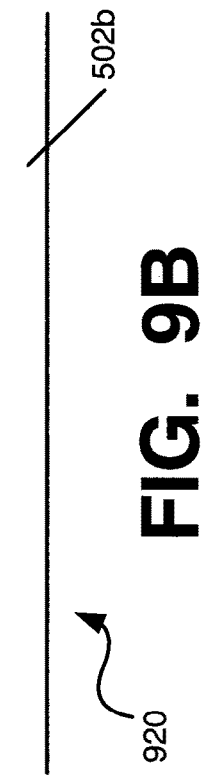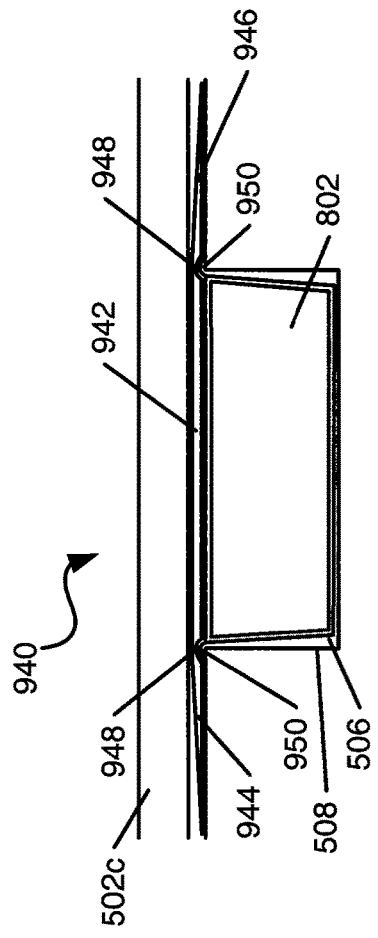

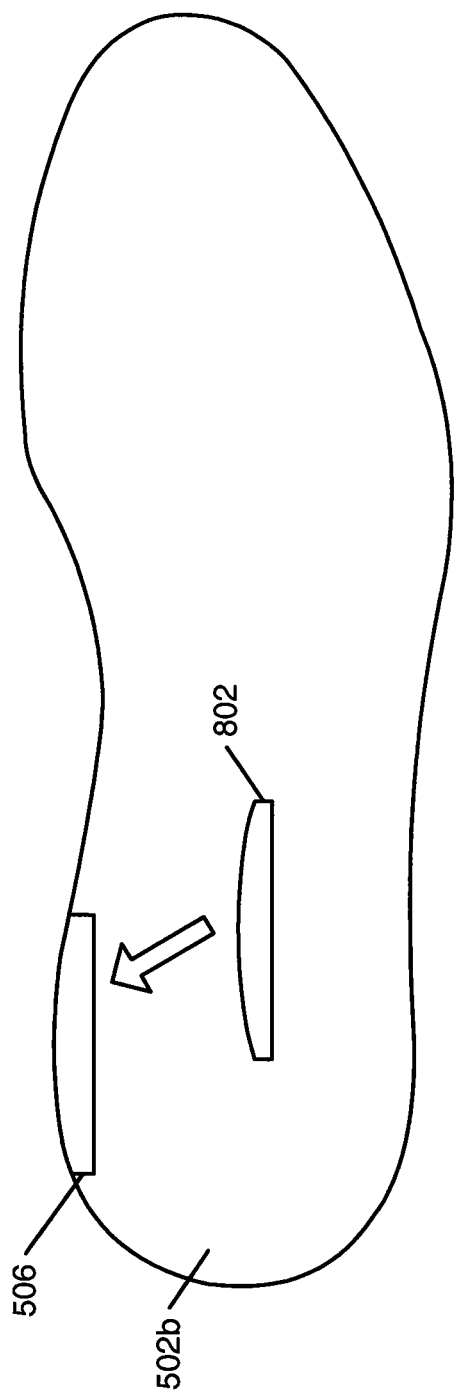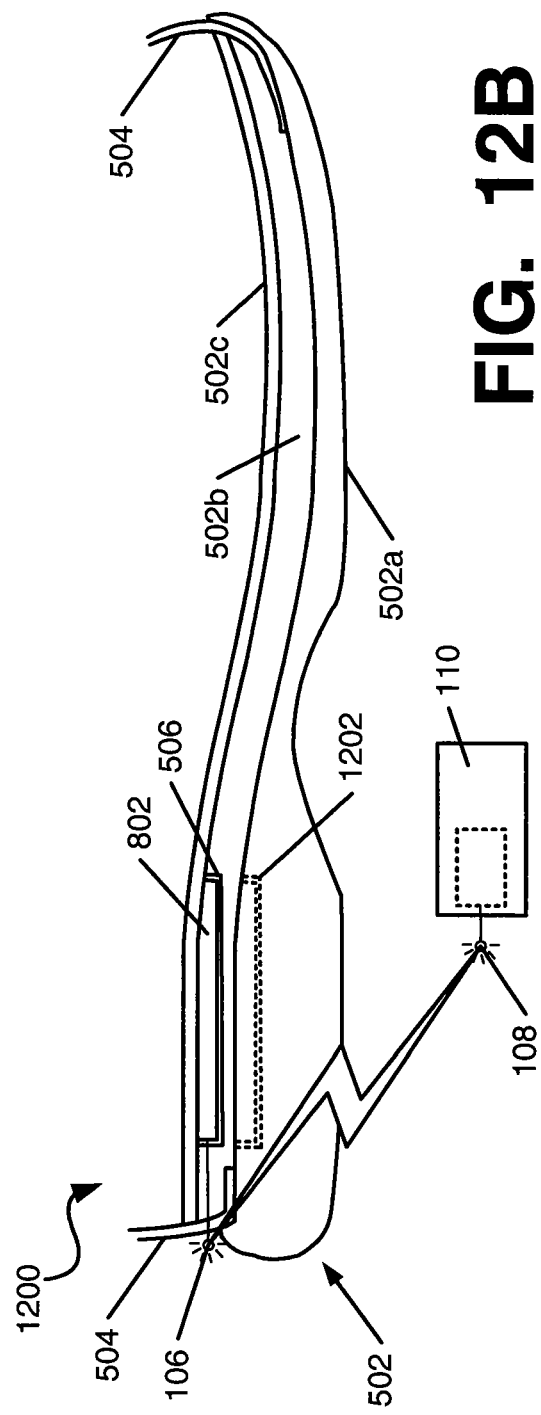
FIG. 12A
FIG. 12B

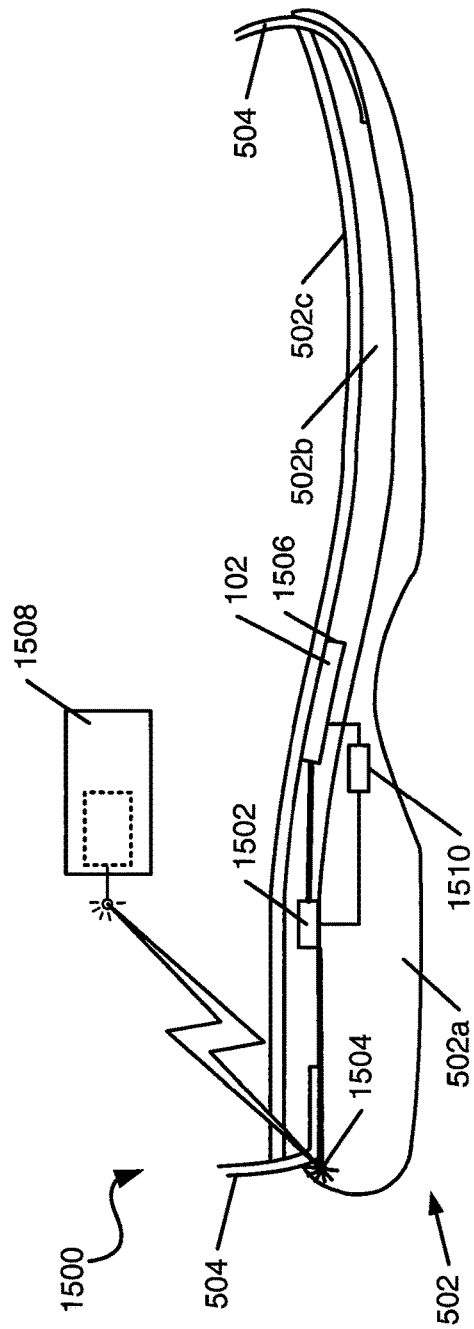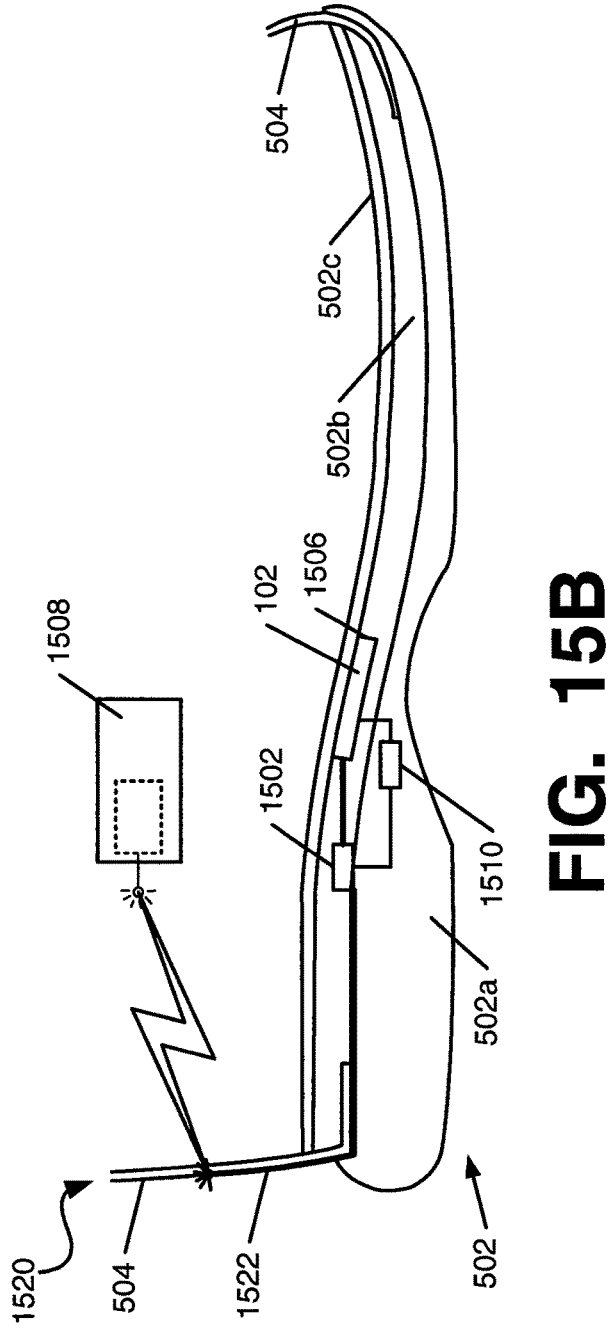
FIG. 15A
FIG. 15B

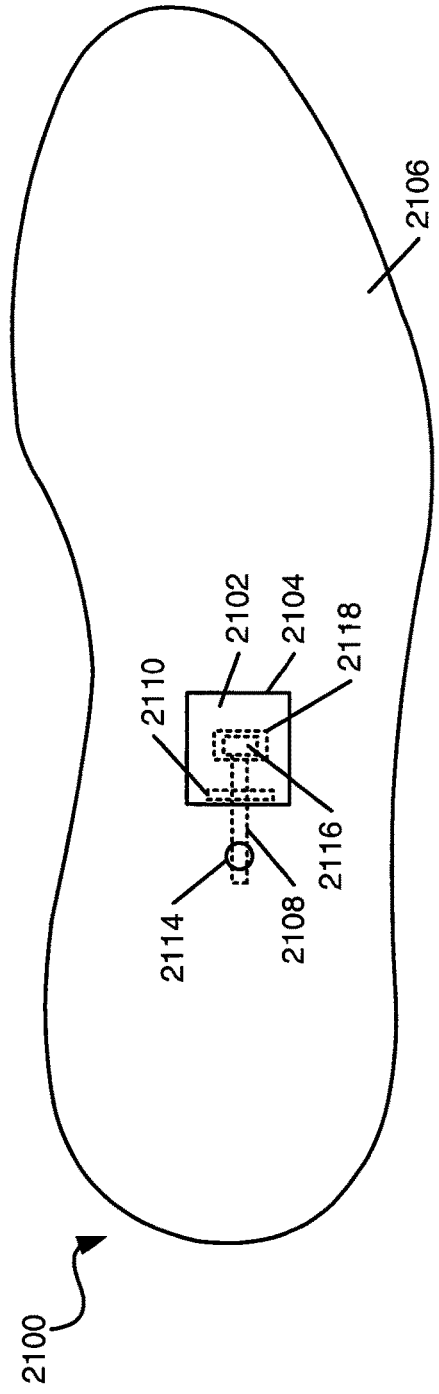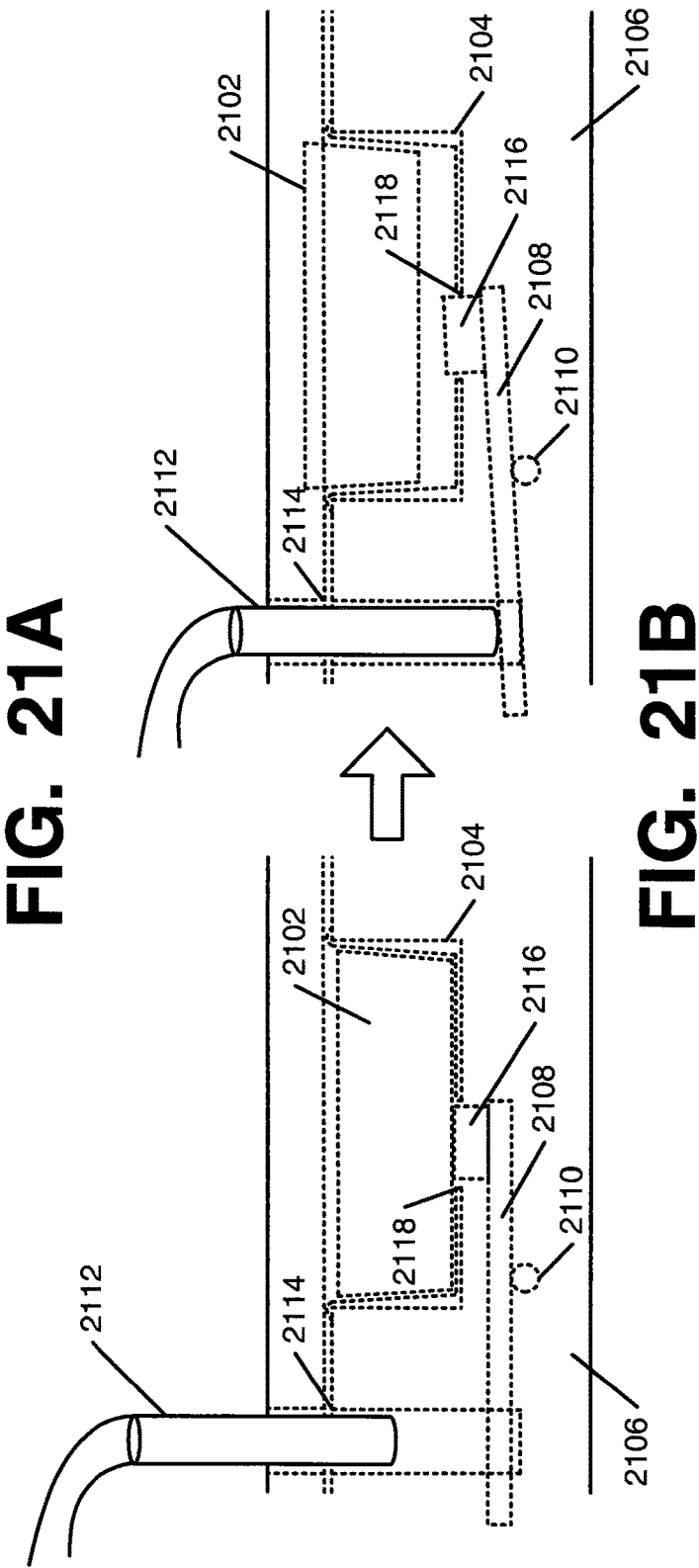
FIG. 21A
FIG. 21B

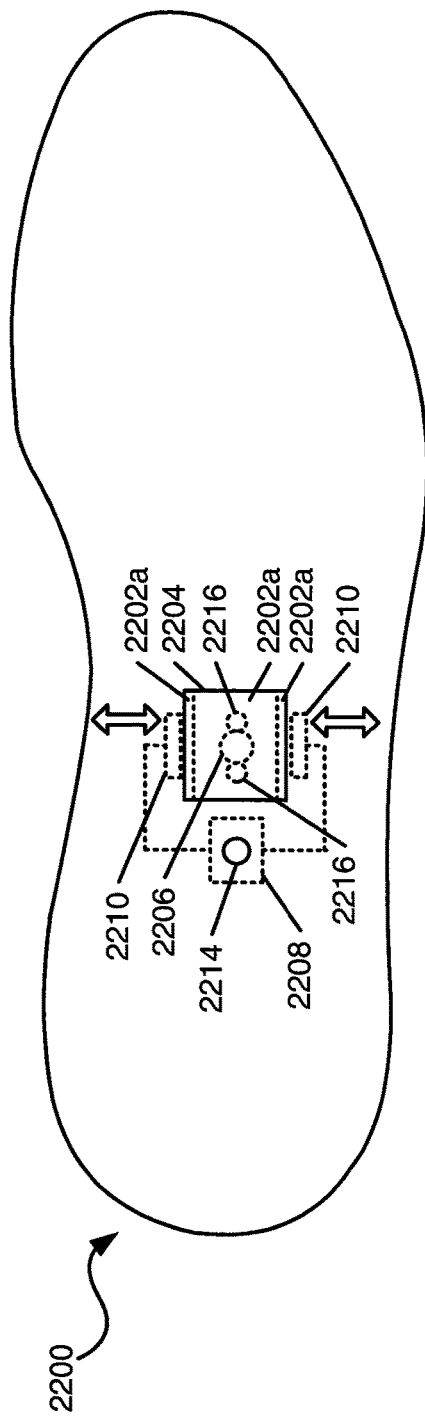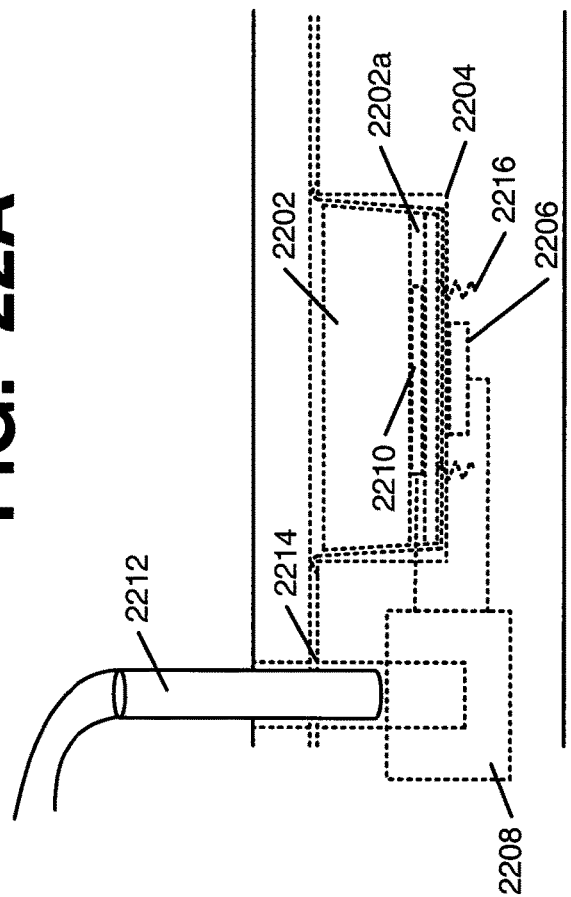

FIG. 25A
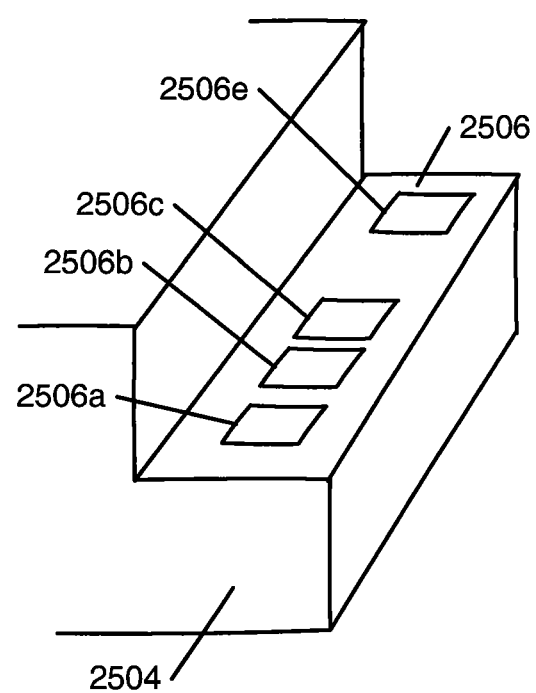
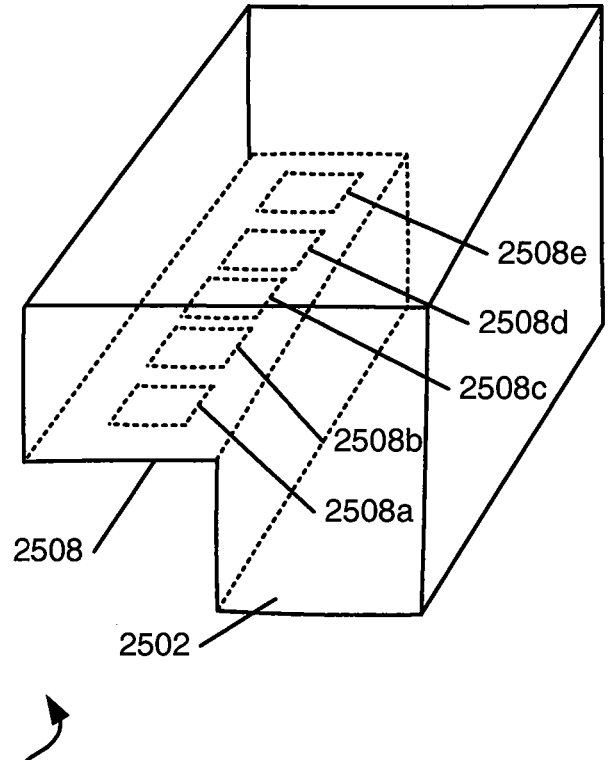
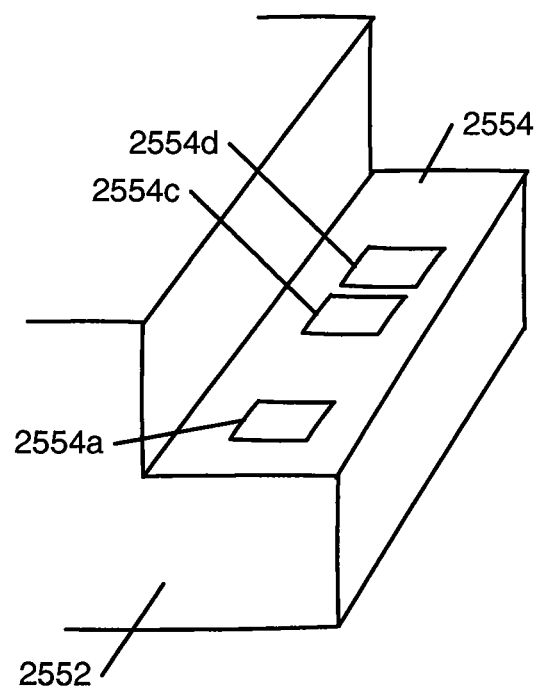
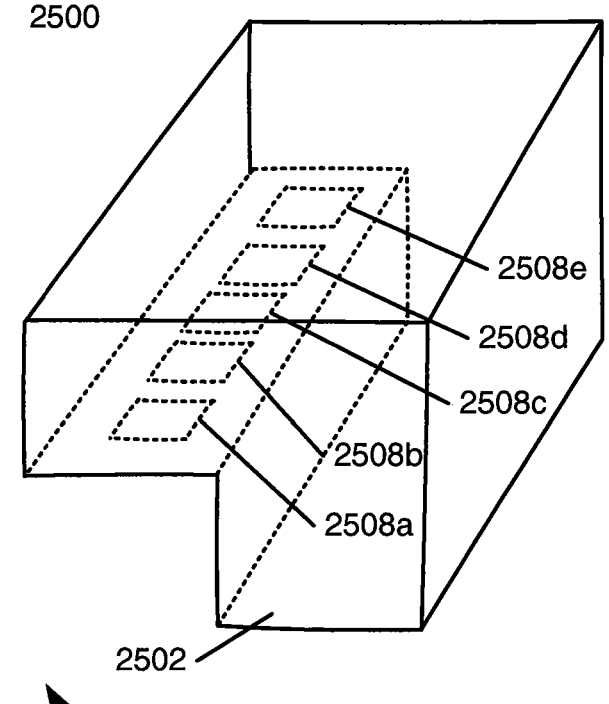
FIG. 25B

ATHLETIC OR OTHER PERFORMANCE SENSING SYSTEMS

CROSS-REFERENCE TO RELATED APPLICATIONS

This application is a continuation of U.S. patent application Ser. No. 16/356,375, filed Mar. 18, 2019, which is a continuation of U.S. patent application Ser. No. 15/676,491, filed Aug. 14, 2017, issued as U.S. Pat. No. 10,251,601 on Apr. 9, 2019, which is a continuation of U.S. patent application Ser. No. 14/491,376, filed Sep. 19, 2014, issued as U.S. Pat. No. 9,782,125 on Oct. 10, 2017, and claims the benefit of priority from U.S. patent application Ser. No. 13/958,545, filed Aug. 3, 2013, issued as U.S. Pat. No. 8,857,078 on Oct. 14, 2014, which is a continuation of U.S. patent application Ser. No. 13/229,967, filed Sep. 12, 2011, issued as U.S. Pat. No. 8,499,476 on Aug. 6, 2013, which is a continuation of U.S. patent application Ser. No. 12/605,811, filed Oct. 26, 2009, issued as U.S. Pat. No. 8,015,732 on Sep. 13, 2011, which is a continuation of U.S. patent application Ser. No. 11/416,458, filed May 3, 2006, issued as U.S. Pat. No. 7,607,243 on Oct. 27, 2009, each entitled "Athletic or Other Performance Sensing Systems." The contents of the above applications are hereby incorporated by reference in their entirety.

FIELD OF THE INVENTION

This invention relates generally to footwear and other products that include electronic modules, e.g., for sensing physical exertion or performance parameters, and housings for holding such modules. Additionally, performance sensing systems and methods of using the above devices for sensing a user's performance also are described.

BACKGROUND

Footwear technology has evolved in recent years such that at least some examples of modern footwear, including athletic footwear, may include various electronic components. For example, footwear systems are known that include devices for sensing and controlling the degree of impact force attenuation provided by the article of footwear, based, for example, on characteristics relating to the present and on-going use of the footwear. Other electronic systems and features associated with footwear are also known.

SUMMARY

Various aspects of this invention relate to articles of footwear, foot-receiving devices, and/or other devices that include one or more electronic modules, e.g., for sensing characteristics of a physical performance (e.g., for measuring one or more physical or physiological parameters associated with an athletic or other performance), as well as to articles of footwear, foot-receiving devices, and/or other devices that include systems for mounting such electronic modules. More specific aspects of this invention relate to: (a) articles of footwear or other structures that include a housing defined therein for receiving electronic modules of the types described above; (b) articles of footwear or other structures that include an asymmetrical housing defined therein for receiving asymmetric electronic modules of the types described above; (c) articles of footwear or other structures that include securing systems and/or release mechanisms for removably mounting electronic modules of the types described above (or other devices) with an article of footwear or other product; (d) articles of footwear or other structures that include activation systems for selectively activating electronic modules of the types described above; (e) articles of footwear or other structures that include authentication systems for selectively activating electronic modules of the types described above; and/or (f) universal receptacles or devices for receiving electronic modules of the types described above (optionally with any one or more of the additional features described above).

Additional aspects of this invention relate to methods of making articles of footwear, other foot-receiving devices, and/or other structures that include housings, electronic modules, securing systems, release systems, activation systems, authentication systems, etc. of the various types described above. Still additional aspects of this invention relate to performance sensing systems (or other physical or physiological parameter measuring or sensing systems) that include electronic modules, articles of footwear, and/or other devices of the types described above, as well as to methods of making and using such systems (e.g., for measuring one or more physical or physiological parameters, optionally associated with a performance, for providing data or other information to the athlete or other user before, during, and/or after the performance, etc.).

BRIEF DESCRIPTION OF THE DRAWINGS

A more complete understanding of aspects of the present invention and at least some features and advantages thereof may be acquired by referring to the following description and the accompanying drawings, in which like reference numbers indicate like features throughout, and wherein:

FIGS. 9A through 9C illustrate various examples of modulating user feel of a housing for an electronic module or other element, optionally including the module or other element mounted therein;

FIGS. 12A and 12B illustrate a portion of an example article of footwear including an athletic performance sensing module or other device in another mounting position in accordance with some examples of this invention;

FIGS. 15A and 15B illustrate various example features and structures for power, antenna, and/or transmission/reception systems in accordance with some examples of this invention;

FIGS. 20-24 illustrate various example features and structures for securing a module in a housing member and releasing a module from the securing system in accordance with examples of this invention;

FIGS. 25A through 26 illustrate various example features and structures of activation, authentication, and/or data algorithm selection features of systems and methods according to examples of this invention.

DETAILED DESCRIPTION

Figure 1:
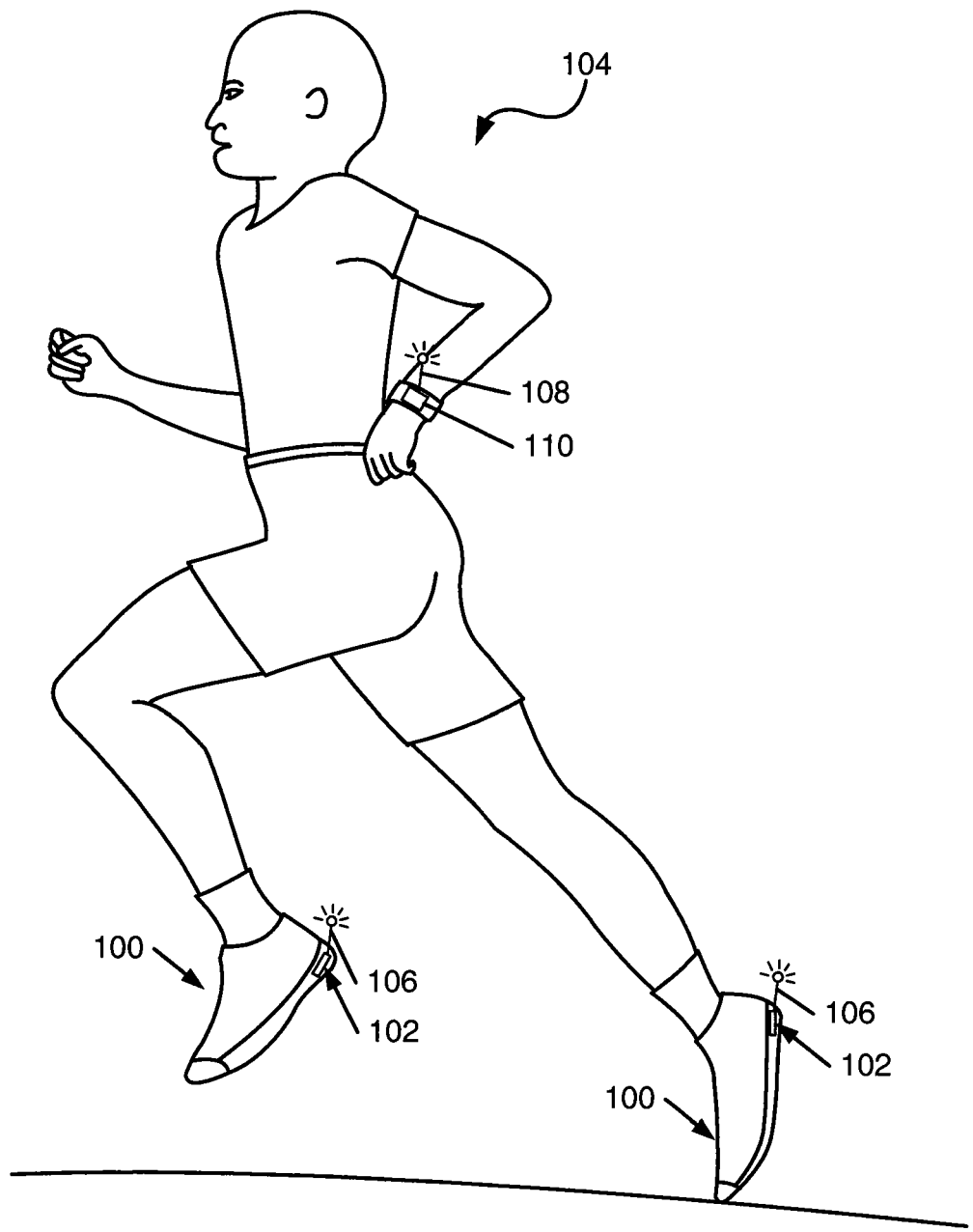
FIG. 1 illustrates an example environment in which footwear products and/or other features and aspects in accordance with examples of this invention may be used.

In the following description of various examples of the present invention, reference is made to the accompanying drawings, which form a part hereof, and in which are shown by way of illustration various structures, embodiments, examples, and environments relating to aspects of the present invention. It is to be understood that other structures, embodiments, examples, and environments may be utilized and structural and functional modifications may be made to the various systems and methods described herein without departing from the scope of the present invention.

The terms "performance" or "athletic performance," as used herein, mean any type of physical exertion or activity. Such activities include, but are not necessarily limited to: workout routines; training exercises; time trials; formal competitions; informal workouts; etc. "Performances" also include activities by persons not involved in physical exertion or activities for purposes of sport, such as children while playing, first responders, elderly or other assisted living and/or hospital patients, physical rehabilitation patients, and the like. The terms "athletic event" or "event" may be used synonymously with "athletic performance" or "performance" in this specification.

"Physical data" or "physical parameters" relating to a "performance" corresponds to any data associated with or relating to any measurable characteristic relating to the performance. Such physical data or parameters include, but are not limited to: physiological data or parameters (described in more detail below); elapsed time; time of day; distance covered; number of steps taken; speed; acceleration; angular velocity; angular acceleration; altitude; barometric pressure; gyroscope generated data; heading or directional data; ambient temperature data; ambient humidity data; wind direction data; wind speed data; global positioning satellite ("GPS") based data; etc.

"Physiological data" or "physiological parameters" relating to a "performance" corresponds to any data associated with or relating to any measurable characteristic relating to a user's person or body. Such physiological data or parameters include, but are not limited to: heart rate; pulse rate; calories burned; calorie burn rate; METS; body weight; body temperature; blood pressure; electrocardiogram data; EEG data; etc.

"Shoes" or "articles of footwear," as used herein, mean any type of product worn on the feet, and these terms include, but are not limited to: all types of shoes, boots, sneakers, sandals, thongs, flip-flops, mules, scuffs, slippers, sport-specific shoes (such as golf shoes, tennis shoes, running shoes, cross-training shoes, baseball cleats, soccer or football cleats, ski boots, etc.), and the like. "Footwear" may protect the feet from the environment and/or enhance a wearer's performance (e.g., physically, physiologically, medically, etc.). As described herein, however, aspects of the invention also may be used and/or practiced in conjunction with any type of "foot-receiving device." The term "foot-receiving device," as used herein, includes any device into which a user places at least some portion of his or her foot. In addition to all types of footwear (described above), foot-receiving devices include, but are not limited to: bindings and other devices for securing feet in snow skis, cross country skis, water skis, snowboards, and the like; bindings, clips, or other devices for securing feet in pedals for use with bicycles, exercise equipment, and the like; bindings, clips, or other devices for receiving feet during play of video games or other games; and the like.

I. GENERAL DESCRIPTION OF ASPECTS OF THE INVENTION

Aspects of the present invention relate generally to footwear and other devices including user performance sensing equipment. As shown in FIG. 1, which generally illustrates an example of the invention and an example environment in which aspects of the invention may be used, one or more individual articles of footwear 100 (such as athletic footwear) may be equipped with electronic modules 102, such as performance measuring modules 102 or modules 102 for other purposes (e.g., RFID transmission/reception, radio or other audio/video transmission/reception, GPS data transmission/reception etc.). The modules 102 may include electronic devices for sensing and/or collecting information during a performance (e.g., during an athletic event or exercise or other performance), for providing information to the footwear user or others (e.g., transmission devices, RFID devices, etc.), and/or for controlling another device (e.g., a footwear impact attenuation system, etc.). While any desired or suitable type(s) of information may be sensed, provided to the user or others, and/or otherwise used or generated, more specific examples of the types of information include: user traveling speed information; distance traveled information; step count information; elapsed time information; GPS information; altitude information; user physiological information; information derived from the GPS, speed, distance, step count, elapsed time, physiological, or other information (e.g., warning information, route information, geographical information, etc.); RFID generated information; and the like.

Additionally or alternatively, the module 102 may be used to control other devices or functions and/or to provide data to other devices, including devices present as part of the article of footwear, devices on the user's person, devices carried by the user, and/or devices at other locations, such as the impact-attenuation characteristics of active impact-attenuation elements included with the article of footwear, display devices, data receiving and processing devices, etc.

As shown in the example of FIG. 1, as the user 104 moves, devices provided in the modules 102 mounted to or included in the footwear 100 will measure, generate, or receive data relating to one or more physical or physiological characteristics associated with the motion and/or with the use of the footwear (e.g., like speed and/or distance information, GPS information, pulse rate, heart rate, and/or the type(s) of information described above), and/or perform other desired functions. If desired, at least some of the data may be stored in a memory (e.g., a memory included with the module 102, separately provided in the footwear 100, provided with a peripheral or remote device, etc.), e.g., for later use and/or analysis, and/or it may be transmitted to the user or others, e.g., via wireless transmission devices 106 optionally included as part of the module 102 or the article of footwear 100. Optionally, if desired, the module 102 and/or the footwear 100 may include one or more microprocessors or other data processing systems or capabilities to enable processing of the data before transmitting the data or other information to the user 104 or others.

The data or desired information may be conveyed to the user 104 or others in any desired manner without departing from the invention, for example, to a wireless receiver 108 provided with a display device 110 carried by the user 104. Optionally, if desired, the display device 110 may be equipped with a microprocessor or other data processing systems or capabilities to enable initial processing of the raw data sent by the module 102 or footwear 100, to enable further processing of data and/or information sent by the module 102 or footwear 100, to enable display of desired data, etc. As more specific examples, the display device 110 may include various electronic devices and/or may be formed in any desired configuration, such as portable, user carried devices, e.g., similar to and/or including functions of a watch, a stopwatch, a PDA type device, a cellular telephone, an MP3 or other audio player, a head worn display device, a pager type device, headphones or earphones, etc. Any type of "display device" also may be provided, such as audio devices, video devices, audio/video devices, alphanumeric displays, radios, televisions, etc., including small, portable, user-carriable versions of such devices.

In light of this general example and general description of an example environment of use, various example aspects of the invention will be described in more detail below, including various example features relating to: the manner in which the module may be engaged with a footwear or other structure, the manner in which the module and/or electronic devices included with it may be activated, the manner in which use of the module by a specific user or in a specific article of footwear or other device may be authenticated, the manner in which data processing algorithms may be selected, the manner in which an electronic module may be secured and/or released from the article of footwear or other device, etc.

A. Footwear Including Interior Plastic Receptacle

One aspect of this invention relates to footwear (or other foot-receiving devices) that include a receptacle for holding an electronic module used in performance sensing (e.g., for use in the various example systems described above in conjunction with FIG. 1). An article of footwear (or other foot-receiving device product) in accordance with at least some examples of this invention may include: (a) an upper member (or other foot-contacting member) at least partially defining a foot-receiving chamber; (b) a sole structure (or other foot-supporting member) engaged with the upper member, wherein the sole structure includes an exterior outsole surface (or other ground-contacting surface) and an impact-attenuating member (e.g., a midsole element, an insole element, a sock liner, a portion of an outsole member, etc.) located between the outsole surface and the foot-receiving chamber, wherein a major surface of the impact-attenuating member has an opening or recess defined therein; and (c) a housing provided in the opening or recess, wherein the housing defines a receptacle facing the foot-receiving chamber.

The receptacle defined by the housing is provided for containing a performance sensing electronic module, such as a module 102 of the various types described above. In some more specific examples, the electronic module may provide at least one of location, speed, or distance information associated with use of the article of footwear. The receptacle, however, need not always contain an electronic module. For example, if desired, the article of footwear may be sold and/or worn without inclusion of an electronic module 102 in the receptacle. In such instances and/or environments, if desired, a fill element (e.g., a non-electronic blank sized and shaped to fit in the housing) may be provided in the housing to at least partially fill the receptacle. The fill element may be made from any desired material, including, for example: a foam material; a rigid plastic, metal, or composite block of material; or other material. This fill material may be used, in at least some instances or in some environments, to at least partially fill the receptacle and prevent an undesirable feel that may be present, e.g., if the empty receptacle is located at a position that would cause a strange feel or discomfort to the wearer.

The electronic module, and/or optionally any desired fill material, may be secured to the housing within the receptacle, optionally in a removable or releasable manner, in any desired manner without departing from this invention. In some examples, a system may be provided to enable stable securing of the electronic module with the housing. Any desired securing system may be used without departing from this invention, including, for example: a cover element engaged with at least one of the impact-attenuating member or the housing that extends across the receptacle (e.g., akin to a battery covering element in various electronic devices, such as handheld electronic games, cellular telephones, cameras, remote controls, and the like); a retaining device engaged with at least one of the impact-attenuating member or the housing that extends at least partially across the receptacle (e.g., such as a restraining strap, bar, or the like); a fastener for holding the module in place with respect to the housing (e.g., a screw or other threaded engagement element, a hook-and-loop type fastener arrangement, a flexible plastic retaining arrangement of the types provided in many battery receptacles for electronic games, etc.); a spring-loaded engagement system (e.g., such as spring biased balls or other members that fit into detent mechanisms (akin to those used in hydraulic couplings), mechanisms of the types used to secure memory cards or other cards in electronic devices such as cellular telephones, digital cameras, audio and/or video recording devices, and the like, etc.); adhesive based securing systems; etc. If desired, at least a portion of the securing system may directly engage at least a portion of the electronic module or fill element, but this is not a requirement. As still another example, if desired, the securing system may include a member (as part of the housing and/or other portion of the footwear structure) that extends into a recess, opening, groove, or discontinuity defined in the electronic module and/or the electronic module may include an extending member that extends into a recess, opening, groove, or discontinuity defined in the housing and/or other portion of the footwear structure.

In at least some examples of footwear structures in accordance with this invention, the housing and the electronic module may be structured so as to be asymmetrical in at least one direction, e.g., such that the electronic module will fit within the housing in a single orientation or in a limited number of orientations with respect to the housing. In at least some examples, these elements may be asymmetrical in a direction extending from the foot-receiving chamber toward the outsole surface of the shoe, such that if the electronic module is not properly mounted (e.g., it is inverted) it will project into the foot-receiving chamber causing discomfort to the user and prompting him/her to correct the module's orientation. Such arrangements can be particularly effective, for example, in situations where the housing is located in an arch, midfoot, or heel portion of the article of footwear. As additional examples, if desired, the housing and/or electronic modules may be designed such that their top and bottom perimeters are sized and/or shaped different from one another (e.g., with a top perimeter or circumference larger than the bottom), such that the electronic module and housing will engage together in a limited and restricted number of relative orientations. In other structures, if desired, the electronic module may be designed to fit into the receptacle in at least two different orientations, one orientation corresponding to an electronic module "ON" position and one orientation corresponding to an electronic module "OFF" position (e.g., changing acceptable orientations by rotating the module by 180 degrees). Such arrangements can be useful, for example, to break electrical connections and/or otherwise turn the electronic module off when collection of data and/or transmission of signals is not desired, e.g., to save battery life, to preserve the lifetime of various components of the system, to disable transmission capability on airplanes, to prevent loss of the electronic module, etc.

The housing, electronic module, and/or receptacle need not be directly exposed to the foot-receiving chamber of the article of footwear. Rather, if desired, a foot-contacting member may be provided to at least partially cover the housing, electronic module, and/or receptacle. This foot-contacting member may constitute, for example, a conventional insole member, sock liner, bootie element, or the like for the article of footwear. Additionally, if desired, this foot-contacting member may include additional impact-attenuating material at the location of the housing, electronic module, and receptacle, to help better mask or modulate user feel and/or awareness of the housing, electronic module, and receptacle. Of course, the foot-contacting member may be readily movable or removable with respect to the housing, if desired, to allow user access to the housing, electronic module, and receptacle.

Articles of footwear according to at least some examples of this invention further may include features and structures that assist in performance data collection and/or transmission aspects as described above in conjunction with FIG. 1. For example, an article of footwear according to at least some aspects of this invention may include an antenna system engaged with and/or formed as part of at least one of the upper member or the sole structure, e.g., to transmit data to an external or remote data processing system and/or display device. The antenna system may be arranged to extend from the housing and operatively couple with an electronic module engaged at least partially within the housing to enable data transfer to/from the module. Alternatively, if desired, the antenna and/or transmission system may be included as part of the electronic module without departing from this invention, such that the footwear structure itself does not require any electrical contacts, data processing capabilities, and/or data transmission/reception capabilities. Of course, any antenna and/or transmission system and/or arrangement with respect to the electronic module and/or housing may be used without departing from this invention.

Another example of potential features and structures for articles of footwear according to this invention includes a power source engaged with at least one of the upper member or the sole structure, e.g., to provide power for operating the electronic device and/or the transmission system (if any). In at least some examples, if desired, the power source may be mounted with the article of footwear and include an electrical contact or terminal located at or engaged with the housing such that the electronic module can receive power from the power source located independent of the electronic module. Alternatively, if desired, the electronic module may include its own power source (e.g., a battery) for operating its sensors and/or processing system, and the footwear may include a separate power source (e.g., for operating a processing system, a transmission system, etc.). As still another example, if desired, a power source on board the electronic module may be used (e.g., via an electrical connection provided through the housing) to provide power to a separate antenna and/or transmission system provided as part of the footwear structure. Of course, any power system arrangement with respect to the antenna and/or transmission system, the housing, and/or the electronic module may be used without departing from this invention.

As is conventional, footwear in accordance with aspects of this invention may be sold and used in pairs. In some examples, both shoes of a pair may include similarly or differently located housings and electronic module receptacles. In such arrangements, the electronic module may be selectively located in either shoe of the pair (one shoe may be better than the other in certain situations or for certain purposes, for example, for data transmission purposes, e.g., depending on whether the user-carried data processing system and/or display system (e.g., a watch or belt-mounted device including athletic performance data processing and/or display capabilities) is carried on his/her right or left side. In such arrangements, a fill element, e.g., of the various types described above, may be provided in any receptacle that does not include an electronic module. As another example, if desired, different electronic modules may be provided in the two shoes, e.g., to measure different physical or physiological parameters, to provide back-up or redundancy in the data capture, etc. In some instances or situations, if desired, fill elements may be provided in both shoes (e.g., when measurements and/or data transmission are not desired, such as during air travel, etc.; at sales locations (e.g., when electronic modules are sold or provided separate from the shoes, etc.); when not engaged in athletic or other performances where measurements are desired; to preserve battery, module, or other system component life; etc.).

Of course, if desired, an individual article of footwear may include plural electronic module mounting locations, e.g., in the form of housings of the types described above, located at multiple locations on a single shoe (e.g., in the interior, in the heel, in the arch or midfoot area, on the shoe exterior, in the tongue area, on the upper member, in the sole member, etc.). If desired, features of the connection between the electronic module and its housing may be used by systems and methods according to the invention for providing information to the electronic module or other data processing system (e.g., as to the type of shoe in which it is mounted, its location in the shoe, etc.). This information may be used for various purposes, such as for data algorithm selection purposes (e.g., to determine the type of physical or physiological parameters to sense and/or display, to determine the frequency of data update or measurement polling, etc.). Also, features of the connection between the electronic module and its housing may tell the data processing system and/or electronic module whether it is mounted in the user's right shoe or left shoe, and this information may be used for any desired purpose in systems and methods in accordance with this invention (e.g., to selectively connect to or activate one of a laterally or medially located antenna system for data transmission/reception purposes, etc.).

Still additional aspects of this invention relate to physical and/or physiological parameter sensing systems that use articles of footwear and electronic modules of the various types described above. In addition, such systems may include one or more of: an electronic module provided in a housing in the article of footwear, wherein the electronic module provides data relating to at least one physical or physiological parameter associated with use of the article of footwear; a transmission system (optionally a wireless transmission system) operatively coupled to the electronic module (e.g., included as part of the module, mounted in the shoe and electrically coupled to the module, etc.) for transmitting data relating to the physical or physiological parameter associated with use of the article of footwear; a processing system for receiving the data relating to the physical or physiological parameter associated with use of the article of footwear; a display device for receiving information from the processing system and displaying information relating to the physical or physiological parameter; and/or a power source operatively connected to at least partially power the electronic module, the transmission system, the processing system, and/or the display device. Of course, additional features, elements, components, and the like may be provided in such sensing systems without departing from this invention, such as module securing systems, module release systems, activation systems, authentication systems, data processing algorithm selection systems, etc.

Still additional features and aspects of this invention relate to methods of making articles of footwear of the various types described above, as well as to methods of using articles of footwear and performance sensing systems of the various types described above to sense one or more characteristics of performances.

B. Other Features and Arrangements for Performance Measuring Electronic Modules

At least some example aspects of this invention do not require the electronic module receiving housing to be located in the footwear interior as described above. Rather, the housing may be provided at a wide variety of positions on an article of footwear without departing from this invention. Accordingly, additional aspects of this invention relate to articles of footwear that include: (a) an upper member at least partially defining a foot-receiving chamber; (b) a sole structure directly or indirectly engaged with the upper member; and (c) a housing for releasably receiving an electronic module, the housing directly or indirectly engaged with at least one of the upper member or the sole structure, wherein the housing defines a receptacle, and wherein an electronic module receiving chamber of the receptacle is asymmetrical in at least one respect (e.g., such that an electronic module can fit therein in a single or limited number of orientations). The housing may be provided at a wide variety of locations, accessible from the footwear interior chamber or exterior to this chamber. As some more specific examples, the housing may be provided: in a midsole portion of the sole structure, in a heel portion of the sole structure, between a midsole member and an outsole member of the sole structure, at a medial posting location, between impact-attenuating column structures included as part of the sole structure, as part of the upper member (e.g., as part of a tongue member, at the rear heel area, in a pocket defined in or on the upper member, etc.), as part of the sole structure (e.g., extending into a portion of the sole structure, fitting into a pocket provided in or on the sole structure, etc.), etc. The chamber of the housing may be accessible from either or both of the article of footwear's interior or exterior. Articles of footwear according to these example aspects of the invention further may include an antenna/data transmission system and/or a power supply, e.g., in the general manners described above.

The electronic module may be engaged with the article of footwear, optionally in a releasable manner, e.g., in any of the various manners and/or using any of the various securing systems and/or releasing systems described above. Additionally, as also described above, the electronic module may be structured such that it will fit within the housing in a single orientation with respect to the housing (and optionally project out from the housing and/or prevent proper closing of the housing when improperly mounted). Alternatively, if desired, the electronic module may be structured such that it will fit within the housing in two or more different orientations, e.g., one orientation corresponding to an electronic module "ON" position and one orientation corresponding to an electronic module "OFF" position, as described above.

Still additional features of this aspect of the invention relate to a pair of shoes, either or both of which may include one or more housings for releasably receiving an electronic module, as described above. Both shoes of the pair may include similarly or differently located housings, and in such arrangements, one or more electronic modules may be selectively located in either shoe of the pair (as noted above, one shoe may be better positioned or situated than the other in certain situations, for example, for data transmission/reception purposes, e.g., depending on whether the user-carried data processing system and/or display system (e.g., a watch or belt-mounted device including performance data processing and/or display capabilities) is carried on the user's right or left side). Again, in such arrangements, a non-electronic fill element, e.g., of the various types described above, may be provided in any receptacle that does not include an electronic module. As another example, if desired, different electronic modules may be provided in the two shoes, e.g., to measure different parameters, to provide back-up or redundancy in the data capture, etc. In some instances, if desired, fill elements may be provided in both shoes (e.g., when measurements and/or data transmission are not desired, such as during air travel, etc.; at sales locations (e.g., when electronic modules are sold or provided separate from the shoes, etc.); when not engaged in performances where measurements are desired; to preserve battery, module, or other system component life; etc.).

Of course, if desired, an individual shoe of the types described above in accordance with this aspect of the invention may include plural electronic module mounting locations, e.g., in the form of housings of the types described above located at multiple locations on a single shoe (e.g., in the interior, in the heel, in the arch or midfoot area, on the shoe exterior, in the tongue area, etc.). The individual housings on a single shoe may be the same or different. If desired, features of the connection between the electronic module and its housing may be used by systems and methods according to the invention for providing information to the electronic module or other data processing system (e.g., as to the type of shoe in which it is mounted, its location in the shoe, etc.). This information may be used for various purposes, such as for data algorithm selection purposes (e.g., to determine the type of physical or physiological parameters to sense and/or display, to determine the frequency of data update or measurement polling, etc.). Also, features of the connection between the electronic module and its housing may tell the data processing system and/or electronic module whether it is mounted in the user's right shoe or left shoe, and this information may be used for any desired purpose in systems and methods in accordance with this invention (e.g., to determine whether to connect to and/or activate a laterally or medially oriented antenna device, etc.).

Still additional features relating to this aspect of the invention relate to physical or physiological parameter sensing systems that use articles of footwear of the various types described above. Such systems additionally may include one or more of: an electronic module provided in the housing, wherein the electronic module provides data relating to at least one physical or physiological parameter associated with use of the article of footwear; a transmission system (optionally a wireless transmission system) operatively coupled to the electronic module (e.g., included as part of the module, mounted in the shoe and electrically coupled to the module, etc.) for transmitting data relating to the physical or physiological parameter associated with use of the article of footwear; a processing system for receiving the data relating to the physical or physiological parameter associated with use of the article of footwear; a display device for receiving information from the processing system and displaying information relating to the physical or physiological parameter; a power source operatively connected to at least partially power the electronic module, the transmission system, the processing system, and/or the display device; an electronic module securing system; an electronic module release system; an activation system; an authentication system; a data processing algorithm selection system; etc. Of course, additional features, elements, components, and the like may be provided in such sensing systems without departing from this invention.

Still additional features relating to this aspect of the invention relate to methods of making articles of footwear of the various types described above, as well as methods of using articles of footwear and performance sensing systems of the various types described above to sense physical parameters, physiological parameters, and/or performances.

C. Features and Arrangements for Securing and Releasing Performance Measuring Electronic Modules from Articles of Footwear or Other Devices Additional aspects of this invention relate to engagement of an electronic module for performance characteristic sensing with an article of footwear. At least some examples of this aspect of the invention relate to an article of footwear that includes: (a) an upper member at least partially defining a foot-receiving chamber; (b) a sole structure directly or indirectly engaged with the upper member; (c) a housing for releasably receiving an electronic module, the housing directly or indirectly engaged with at least one of the upper member or the sole structure, wherein the housing defines an electronic module receiving chamber formed in or on at least one of the upper member or sole structure; and (d) a system for releasably securing an electronic module with the housing and/or in the chamber.

Any desired system for releasably securing the electronic module within the chamber of the housing may be used without departing from this invention. For example, this securing system may include one or more retaining members (e.g., as part of the housing or other portion of the shoe structure) that extend into one or more openings, recesses, grooves, and/or discontinuities provided in the electronic module structure. As additional examples, the securing system may include a cover element or a retaining device, optionally including a fastener element that engages with the housing or the electronic module, that extends at least partially across the chamber or receptacle. Adhesives and/or hook-and-loop type fastener arrangements also may be used to engage a cover or retaining element over the electronic module and/or to directly engage the electronic module with the housing. The securing system may be mechanically activated or operated, electronically activated or operated, and/or electromechanically activated and/or operated.

In accordance with at least some examples of this aspect of the invention, a release mechanism may be provided for releasing an electronic module mounted in the chamber (e.g., to release the electronic module from its secured engagement with the housing or the article of footwear). The release mechanism may be mechanically operated or activated, electronically operated or activated, and/or electromechanically operated or activated, and it may include a spring member, e.g., that biases the securing system and/or release system into a module engaging or disengaging position, that helps push the electronic module out of the housing, etc. As additional examples, the release mechanism may include movable retaining elements that engage/disengage the module in some manner and/or move the module into or out of the housing in some manner.

Still further examples of articles of footwear and/or systems according to this aspect of the invention may include a tool for activating the securing system and/or its release mechanism. If desired, the tool may be releasably engagable with the article of footwear, such as via a friction fit, retaining strap, cover member, detent or other retaining mechanism, or via other securing means. The releasing tool may be internally or externally located with respect to the footwear's foot-receiving chamber and may be engaged with the upper member (e.g., in a pocket provided in the tongue or other portion of the upper member, etc.) or with the sole structure (e.g., in a pocket or chamber defined in or between various portions of the sole member, etc.). In at least some examples, the tool may be constructed as the aglet for a shoe lace engaged with the article of footwear, e.g., that extends into an opening in the upper member or sole structure to provide access to the securing and/or release mechanisms and/or an activation system for such mechanisms. As more specific examples, if desired, the housing for the electronic module may be provided in the interior of an article of footwear, and the securing and/or release mechanisms (which may be mechanically, electronically, and/or electromechanically activated and/or operated) may be accessed and activated by pushing the aglet of a shoe lace (or other tool) through an opening defined in the impact-attenuating element of the shoe (e.g., the shoe midsole) and/or through an opening defined in an insole member or a sock liner. If desired, the aglet, tool, and/or access openings therefor may have their exterior surfaces shaped in any desired manner, e.g., to limit the shape of a tool capable of accessing the securing and/or release mechanisms. As another alternative, if desired, the securing system and/or release system may be included as part of the electronic module and/or may be activated through use of a tool as described above, which may be inserted into an opening provided in the electronic module.

If desired, systems and methods according to this example aspect of the invention (as well as the various aspects of the invention described above) further may include an electronic module activation system for activating an electronic module when included in the chamber. This activation system, in some examples, may constitute an ON/OFF switch. If desired, the activation system may be located at a remote or not easily accessible position in the footwear structure, e.g., within the interior of the sole structure, such that an activation tool of some sort may be required to activate the electronic module. The activation system and/or activation tool for that system may be located and utilized in the various manners described above for the release mechanism location and tool (e.g., by providing the activation system switch within the sole structure and activating it with a tool (such as an aglet or other narrow key type element) that extends into corresponding openings provided in one or more of the sock liner, insole member, midsole member, housing element, or the like. Alternatively, if desired, the activation system may include a button on the module itself or an activation system activated by a tool as described above through an opening defined in the module.

Of course, if desired, individual shoes of the types described above in accordance with this aspect of the invention may include plural electronic module mounting locations, securing systems, release mechanisms, activation systems, activation tools, release tools, and the like, e.g., of the types described above, located at multiple locations on a single shoe. Also, either or both shoes of a single pair may include these various systems and features without departing from this invention.

Still additional features relating to this aspect of the invention relate to physical and/or physiological parameter sensing systems that use articles of footwear of the various types described above in accordance with this aspect of the invention. Additional features relating to this aspect of the invention relate to methods of making articles of footwear of the various types described above, as well as to methods of using articles of footwear and sensing systems of the various types described above. Still additional features relating to this aspect of the invention relate to methods for securing electronic modules with articles of footwear, activating electronic modules secured with articles of footwear, and/or releasing electronic modules from a secured relationship with an article of footwear using the various systems and methods described above.

D. Features and Arrangements for Activating and/or Authenticating Operation of Performance Measuring Electronic Modules This invention additionally relates to various structures and systems for activating and/or authenticating operation of a performance parameter sensing module with a specific shoe. Such systems may include: (a) an upper member at least partially defining a foot-receiving chamber; (b) a sole structure directly or indirectly engaged with the upper member; (c) a housing for receiving an electronic module, the housing engaged with at least one of the upper member or the sole structure, wherein the housing defines an electronic module receiving chamber formed in or provided on at least one of the upper member or sole structure; (d) an activation system for activating an electronic module with the chamber; and/or (e) an authentication system for receiving input information (e.g., electronic data, sensor readings, detector signals, user entered input, etc.) and confirming authorization for use of an electronic module in the chamber based, at least in part, on the input information. The activation and/or authentication systems further may include activation tools, e.g., of the various types described above (e.g., as an aglet for the shoe lace, as a separate member releasably engagable with the upper member or the sole structure, as a separately carried member, etc.). The activation and/or authentication systems or portions thereof may be provided at any desired locations in the shoe structure, including in the various locations described above. Alternatively, if desired, at least portions of the activation and/or authentication systems may be included in or with the electronic module, and the tool may engage or interact with the module. Additionally or alternatively, some or all of the activation system and/or authentication system may be provided as part of other features of the sensing systems, such as with a remote processing device, with a remote display device, etc.

As noted above, activation and/or authentication systems in accordance with at least some examples of this invention may include a wide variety of different structures, at a wide variety of different locations, including the various structures and locations described above. As still further examples, the activation and/or authentication systems may include one or more members extending from one or more walls of the housing for extending into one or more openings, recesses, grooves, or discontinuities defined in the electronic module and/or one or more members extending from one or more walls of the electronic module into one or more openings, recesses, grooves, or discontinuities defined in the housing and/or footwear structure. As still additional examples, if desired, the activation and/or authentication systems may include one or more members extending from a sock liner, insole element, bootie member, or the like that extend into one or more openings, recesses, grooves, and/or discontinuities defined in the electronic module. In at least some instances, use of the activation and/or authentication systems will result in making an electrical connection, e.g., between a first electrical conductor provided with the module and a second electrical conductor provided with the housing and/or shoe structure, between the electronic module and a power source optionally located external to the electronic module, etc.

In at least some examples of this invention, the activation and/or authentication systems may provide information to a data processing system associated with the electronic module (e.g., on board or in communication with the electronic module). This information may include, for example, mounting location information (e.g., with respect to the shoe structure); shoe type information; right or left shoe mounting information, etc. This information may be used, at least in part, in selecting a data processing algorithm for use by the electronic module (e.g., to determine the type of physical and/or physiological parameters to measure, to determine the type of information data provided for display, to determine characteristics of the data collection or display, etc.) and/or in selecting various components of the system to activate and/or utilize.

Of course, if desired, individual shoes of the types described above in accordance with this aspect of the invention may include plural electronic module mounting locations, activation systems, authentication systems, activation tools, and the like, e.g., of the types described above, located at multiple locations on a single shoe. Also, either or both shoes of a single pair may include these various systems and features without departing from this invention.

Additional features relating to this aspect of the invention relate to physical and/or physiological parameter sensing systems that use articles of footwear of the various types described above. Still additional features relating to this aspect of the invention relate to methods of making articles of footwear of the various types described above, as well as methods of using articles of footwear and performance parameter sensing systems of the various types described above to sense one or more characteristics of a performance. Still additional features relating to this aspect of the invention relate to methods for activating electronic modules and/or authenticating use of electronic modules secured with articles of footwear using the various systems and methods described above.

E. Universal Receptacles for Performance Measuring Electronic Modules

Aspects of this invention further relate to other systems and/or devices that include receptacles for electronic modules for sensing one or more characteristics of performances of the various types described above. Performance sensing systems in accordance with this aspect of the invention may include one or more of the following: (a) a housing defining an electronic module receiving chamber, wherein the electronic module receiving chamber is asymmetrical in at least one respect (e.g., sized and/or shaped so that the electronic module will fit therein in a single or limited number of orientations); (b) an electronic module received in the chamber, wherein the electronic module provides data relating to at least one physical or physiological parameter associated with a performance, optionally wherein the electronic module is structured such that it will fit into the housing in a single or limited number of orientations with respect to the housing; (c) a system for securing the electronic module in and/or releasing the module from the chamber; (d) a system for securing the housing to another object; (e) a power source for providing power to the electronic module; (f) a data transmission system for transmitting data relating to the physical or physiological parameters from the electronic module; (g) a data processing system for receiving the data from the data transmission system; (h) a display system for displaying data or information relating to the performance; (i) an activation and/or authentication system; etc.

A wide variety of potential structures and arrangements of these elements may be provided without departing from the invention. For example, the data transmission system may be engaged with the electronic module, engaged with the housing and operatively coupled with the electronic module, or separate from the module and the housing. Additionally, at least some portion of the data processing system and/or data processing capabilities of the system may be included as part of the electronic module, included as part of the housing, remote from the housing and connected via the data transmission system (including a wired or wireless connection, etc.), etc. If desired, at least some portions of the system, including the data processing system and/or display system, may be sized, shaped, and/or weighted so as to be carried by a user of the performance sensing system, e.g., during an athletic or other performance being sensed, e.g., as a wrist mounted system, as a belt or clothing mounted system, as a shoe mounted system, etc.

Any desired system for securing the electronic module to and/or releasing the electronic module from the housing may be used without departing from this invention, including the various systems described above. Also, any desired system and/or structures for securing the housing to another object (including a person or a person's clothing) may be used without departing from this invention, including, for example, a belt member, a band member, a shoe lace member, a clip or clasp member, an adhesive, a suction member, a fastener arrangement, and the like.

Still additional features of this aspect of the invention relate to methods for providing performance sensing systems and/or methods for using performance sensing systems of the various types described above.

II. SPECIFIC EXAMPLES OF THE INVENTION

While aspects of the invention generally have been described above, the following provides more detailed, specific examples of systems, methods, and structures in accordance with the invention. Those skilled in the art should understand, of course, that the following description constitutes descriptions of examples of the invention and should not be construed as limiting the invention in any way. Moreover, in the description that follows, various connections are described between elements in overall structures. The reader should understand that these connections in general, and unless other specified, may be direct or indirect and that this specification is not intended to be limiting in this respect.

A. Basic Example of an Overall System

As noted above, FIG. 1 generally illustrates an example environment in which systems and methods according to at least some examples of this invention may be used. In this example, the system includes one or more articles of footwear 100 and an electronic module 102 engaged with the article of footwear 100 (or otherwise carried by the user 104). The electronic module 102 of this example system transmits data from the article of footwear 100 via data transmission system 106 to a remote system 110. In this illustrated example system, the data transmission system 106 of the electronic module 102 communicates wirelessly with a receiver element 108 provided with the remote system 110.

The article of footwear 100 may be of any desired construction without departing from this invention. For example, the article of footwear 100 may include an upper member engaged with a sole member in any desired manner, such as via stitching, adhesives, cements, mechanical connectors, fusing techniques, and the like, including in conventional manners known and used in the art. The article of footwear 100 may be of any desired construction, made up of any desired materials, and may include any desired type of closure system (such as laces, buckles, hook-and-look fasteners, magnetic closure systems, clamps, clasps, other mechanical connectors, retaining elements, and the like) or no closure system. In general, the article of footwear 100 may represent any of many conventional footwear structures, including athletic footwear type structures and/or structures known and available in the art.

The electronic module 102 may be engaged with the article of footwear 100 in any desired manner without departing from the invention. For example, the electronic module 102 may be integrally formed with the article of footwear 100 during manufacture such that the electronic module 102 is fully or partially concealed within the remainder of the structure of the article of footwear 100. As another example, if desired, the electronic module 102 may fit into a pocket, slot, groove, housing, or other structure integrally formed in or on the article of footwear 100 (e.g., formed in or on the upper member or in or on any portion of the sole member) such that the electronic module 102 may be removably inserted into and/or otherwise attached with the article of footwear 100 and freely engagable with and/or detachable therefrom. In some examples, the electronic module 102 may fit into a housing, slot, or pocket formed in a midsole or other portion of an article of footwear 100, e.g., using any desired connection structure, such as structures of the types used for releasably securing battery compartment covers, memory cards, PCMCIA cards, and/or other devices with electronic or computer devices.

The electronic module 102 may include and/or operatively connect with one or more data transmission/reception elements 106 capable of electronic communication and data transfer with one or more remote devices 110 (e.g., communication and data transfer with a transmission/reception element 108 provided with the remote device 110). Electronic communications in any form, using any desired data transfer forms, formats, and/or protocols, may be used without departing from this invention. As examples, the data transmission/reception elements 106 and/or 108 may communicate with one another in wired or wireless manners without departing from this invention. As some more specific examples, the data transmission/reception elements 106 and/or 108 may communicate with one another via radio transmissions, cellular telephone transmissions, infrared radiation transmissions, RFID transmissions, or the like. Also, if desired, each of the data transmission/reception systems 106 and 108 and/or remote system 110 may be capable of both sending and receiving data, to thereby enable two way communications between the electronic module 102 and the remote system 110 without departing from this invention (e.g., to allow data input to the electronic module 102 and/or its various components or electronic components of the footwear, if necessary or desired, for example reasons to be explained in more detail below, etc.).

Figure 2:
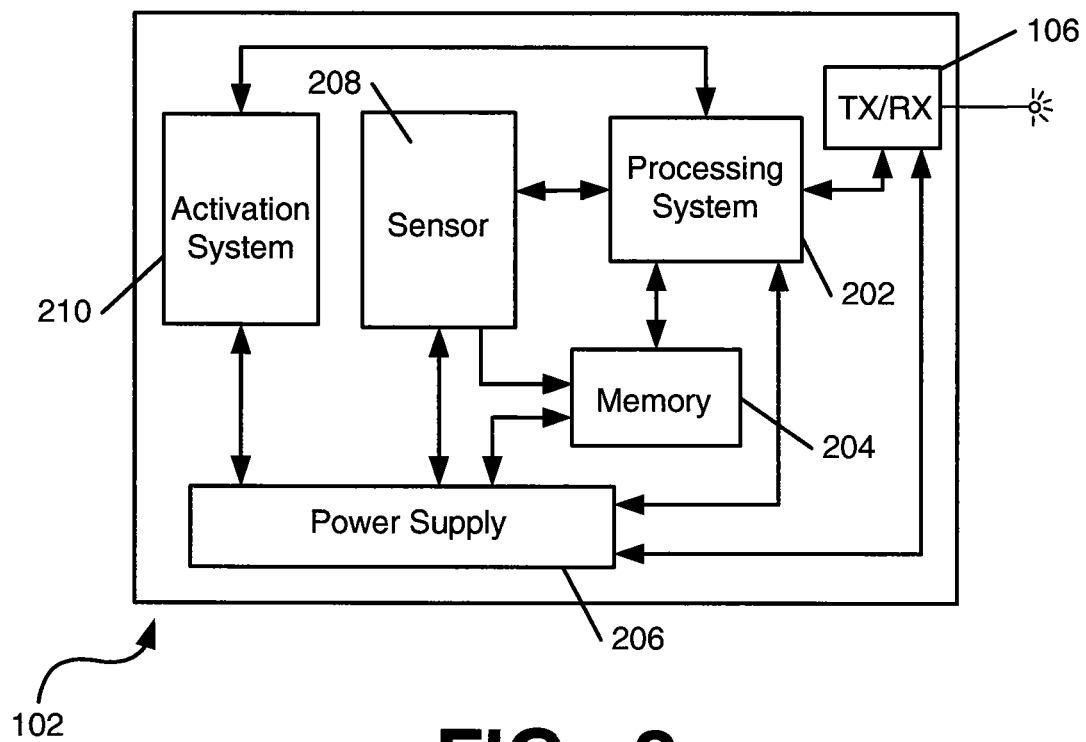
FIG. 2 illustrates a schematic block diagram of an example electronic module that may be used, e.g., for sensing physical or physiological characteristics or data, for example, associated with physical exertion or exercise or the like, in accordance with examples of this invention.

FIG. 2 includes a schematic diagram of an example electronic module 102 including data transmission/reception capabilities that may be used in accordance with at least some examples of this invention. While the example structures of FIGS. 1 and 2 illustrate the data transmission/reception system 106 as integrated into the electronic module structure 102, those skilled in the art will appreciate (as described in various examples below) that a separate component may be included as part of a footwear structure 100 or other structure for data transmission/reception purposes and/or that the data transmission/reception system 106 need not be entirely contained in a single housing or a single package in all examples of the invention. Rather, if desired, various components or elements of the data transmission/reception system 106 may be separate from one another, in different housings, on different boards, and/or separately engaged with the article of footwear 100 or other device in a variety of different manners without departing from this invention. Various examples of different potential mounting structures are described in more detail below.

In the example of FIG. 2, the electronic component 102 includes a data transmission/reception element 106 for transmitting data to and/or receiving data from one or more remote systems (e.g., to/from remote system 110). The electronic component 102 of this example further includes a processing system 202 (e.g., one or more microprocessors), a memory system 204, and a power supply 206 (e.g., a battery or other power source). A "sensor" 208 may be provided to sense or provide data or information relating to a wide variety of different types of parameters, such as physical or physiological data associated with use of the article of footwear 100 or the user, such as pedometer type speed and/or distance information, other speed and/or distance data sensor information, temperature, altitude, barometric pressure, humidity, GPS data, accelerometer output or data, heart rate, pulse rate, blood pressure, body temperature, EKG data, EEG data, etc., and this data may be stored in memory 204 and/or made available, for example, for transmission by the transmission/reception system 106 to some remote location or system. The sensor 208 may include an accelerometer, e.g., for sensing direction changes during steps (for pedometer type speed and/or distance information), for sensing jump height, etc.

As additional examples, electronic modules, systems, and methods of the various types described above may be used for providing automatic impact attenuation control for articles of footwear. Such systems and methods may operate, for example, like those described in U.S. Pat. No. 6,430,843, U.S. Patent Application Publication No. 2003/0009913, and U.S. Patent Application Publication No. 2004/0177531, which describe systems and methods for actively and/or dynamically controlling the impact attenuation characteristics of articles of footwear (U.S. Pat. No. 6,430,843, U.S. Patent Application Publication No. 2003/0009913, and U.S. Patent Application Publication No. 2004/0177531 each are entirely incorporated herein by reference). When used for providing speed and/or distance type information, sensing units, algorithms, and/or systems of the types described in U.S. Pat. Nos. 5,724,265, 5,955,667, 6,018,705, 6,052,654, 6,876,947 and 6,882,955 may be used. These patents each are entirely incorporated herein by reference.

As further shown in FIG. 2, the electronic module 102 of this example includes an activation system 210. The activation system 210 or portions thereof may be engaged with the module 102 or with the article of footwear 100 (or other device) together with or separate from other portions of the electronic module 102. The activation system 210 may be used for selectively activating the electronic module 102 and/or at least some functions of the electronic module 102 (e.g., data transmission/reception functions, etc.). A wide variety of different activation systems may be used without departing from this invention, and a variety of such systems will be described in more detail below with respect to various included figures.

Figure 3:
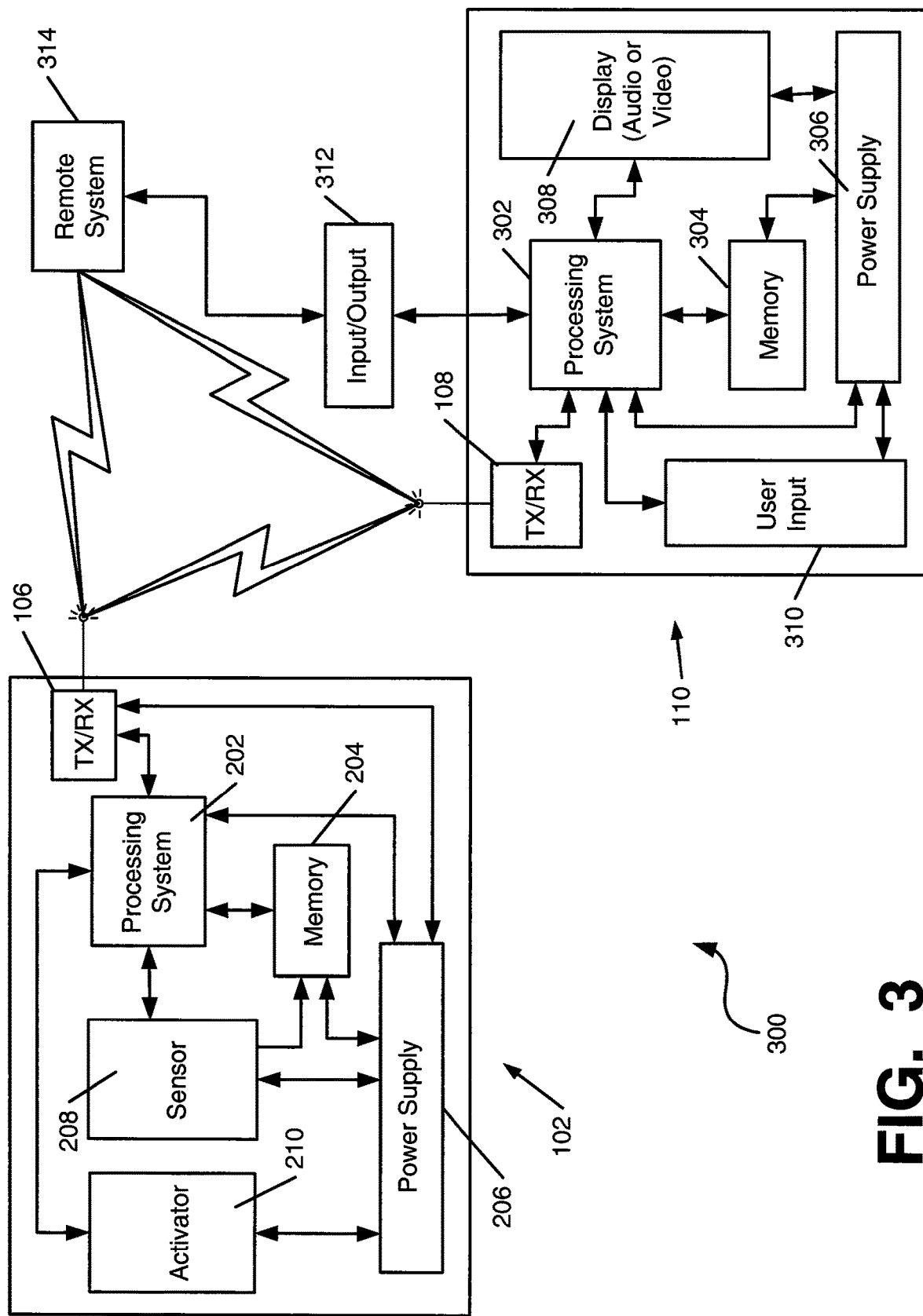
FIG. 3 illustrates a schematic block diagram of an example athletic performance sensing system or other physical or physiological data measuring or sensing system in accordance with examples of this invention.

FIG. 3 illustrates a schematic diagram of an overall example performance sensing system 300 in accordance with some examples of this invention. This system 300 includes an electronic module 102 of the type described above in conjunction with FIG. 2. As noted above, if desired, at least some portions of the illustrated module 102 (e.g., the activation system 210, the transmission/reception system 106, etc.) actually may be provided separate from the electronic module 102 (in which case, input from these systems may be provided to module 102 in any desired manner, e.g., to processing system 202 via a wired or wireless connection, via pins or contact pads, etc.). The input from the activation system 210 also may be provided in any desired form or format without departing from the invention. As some more specific examples, if desired, the activation system 210 may include a simple button, switch, or other input source that simply provides an activation or deactivation signal to the processing system 202 and/or transmission/reception system 106 of the electronic module 102 (e.g., a logical "1" or "0"). If desired, in at least some examples according to this invention, the activation system 210 may constitute an external button or other device, optionally mounted on the article of footwear 100, the remote system 110, or otherwise carried by the user, such that a user can manually activate the system or it can otherwise be activated (optionally automatically activated when a user steps down, stomps, lands a jump, etc.), to induce the electronic module 102 or its data transmitter/receiver 106 to operate.

FIG. 3 further includes a schematic diagram illustrating various example components and features of a remote device 110, e.g., as shown in FIG. 1. This remote device 110 includes a transmitter/receiver element 108 for transmitting data to and/or receiving data transmitted by electronic module 102. The remote device 110, as illustrated in FIG. 3, may include its own processing system 302 (e.g., one or more microprocessors), memory system 304, and/or power supply 306.

The remote device 110 may be programmed and adapted to perform various functions in accordance with examples of this invention. For example, the remote device 110 may include an audio, video, and/or alphanumeric display device 308 for displaying information, e.g., to the footwear user or to a third party, wherein the displayed information may be based, at least in part and in some instances, on the data transmitted by the electronic module 102. Additionally or alternatively, if desired, the remote device 110 may include a user input system 310, for receiving user input, e.g., to enter or adjust settings, to control the functions or settings of the remote system 110 or various components thereof, and/or to enter settings or control the functions of the electronic module 102 or the various components thereof (such as the activation system 210, the sensing system 208, etc.). Any desired type of input system 310 may be provided without departing from the invention, including, for example, a keyboard input, a stylus type input, a voice input, a button type input, a soft keyboard, etc.

If desired, user input and/or other data or information accepted and/or generated by the remote system 110 may be transmitted back to the electronic module 102, e.g., via data transmission/reception element 108. Alternatively or additionally, if desired, user input or other data or information generated by the remote system 110 may be sent to the electronic module 102 and/or to one or more other systems (such as remote system 314) via input/output system 312 (e.g., a data transmission line, a wireless transmission system, an internet connection, etc.). The remote systems 314 may take on any desired form without departing from the invention, such as a computer or computing system, a remote display device, another data transmission system, or the like. If desired, communication directly between the remote system 314 and the electronic module 102 may be enabled (without the need to pass through the intermediate remote device 110). Connections between remote system 110, remote system 314, and/or the electronic module 102 may take on any desired form, such as wired or wireless connections, and the data may be transferred in any desired form or format without departing from this invention.

Figure 4:
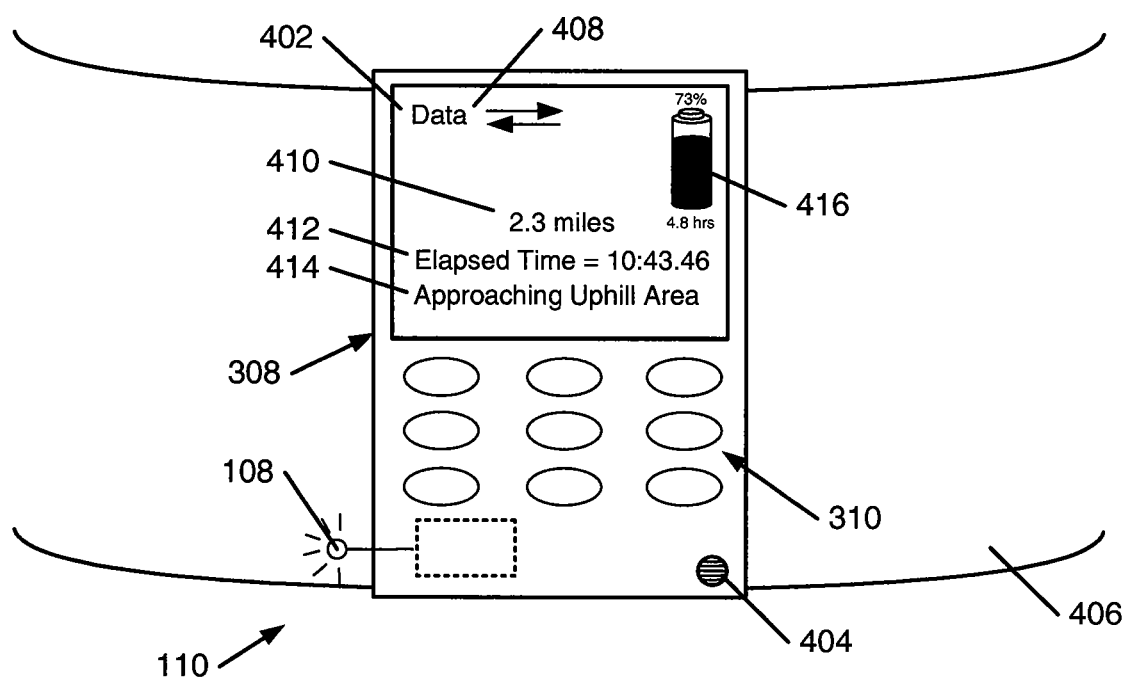
FIG. 4 illustrates an example remote device that may be used to display information to an athlete or other user during the course of a performance, in accordance with examples of this invention.

FIG. 4 illustrates an example of a remote device 110 of the type that may be carried by an athlete or other user during the course of the performance being sensed. In this illustrated example, the remote device 110 includes the data transmitter/receiver element 108 as well as display device 308 (including a video/alphanumeric display device 402 and audio speaker 404) and user input device 310. The remote device 110 further includes a band member 406, e.g., for attachment to a user's clothing, body, or equipment. Of course, any desired type of system may be provided for attaching this remote device 110 to another object, if desired, including bands of different types (e.g., various types of watch-type bands), chains or other neck engaging devices, clips, clamps, clasps, mechanical fasteners, and the like.

Also, while any desired type of information may be provided on display 402 and/or warning beeps or audio information may be provided via audio element or speaker 404, in this illustrated example, the video display device 402 provides a data transmission/reception icon 408, a "traveled distance" display 410, an "elapsed time" display 412, a "warning" display 414 (which may obtain data or information from GPS, map data, communication from remote system 314, etc.), and a battery life indicator 416. Of course, other information, changing information, and/or combinations of different types of information may be provided without departing from this invention. Additionally or alternatively, if desired, the remote device 110 may include one or more buttons (hard or soft buttons, such as input device 310) or other input elements that allow user selection of various different types of information for display and/or forms, formats, or manners of displaying such information.

Given the above description of various example elements of an overall performance sensing system, a more detail description follows of various example footwear structures and other structures and components that may be used in performance sensing systems.

B. Footwear Structures with Electronic Module Receptacles

While there are many ways that a user 104 can carry a physical or physiological measuring electronic module or other module 102 in the systems and methods illustrated by FIGS. 1-4, in at least some examples of this invention, the electronic module 102 will be mounted and carried in or on an article of footwear 100. In this manner, the electronic module 102 can be carried easily by the user 104, in many instances without the user really feeling or noticing its presence. Moreover, the size, shape, and mounting of the module 102 may be selected such that the presence of the module 102 has little or no adverse effect on the performance. A wide variety of footwear or other structures 100 may be used to hold an electronic module 102 without departing from this invention.

Figure 5A:
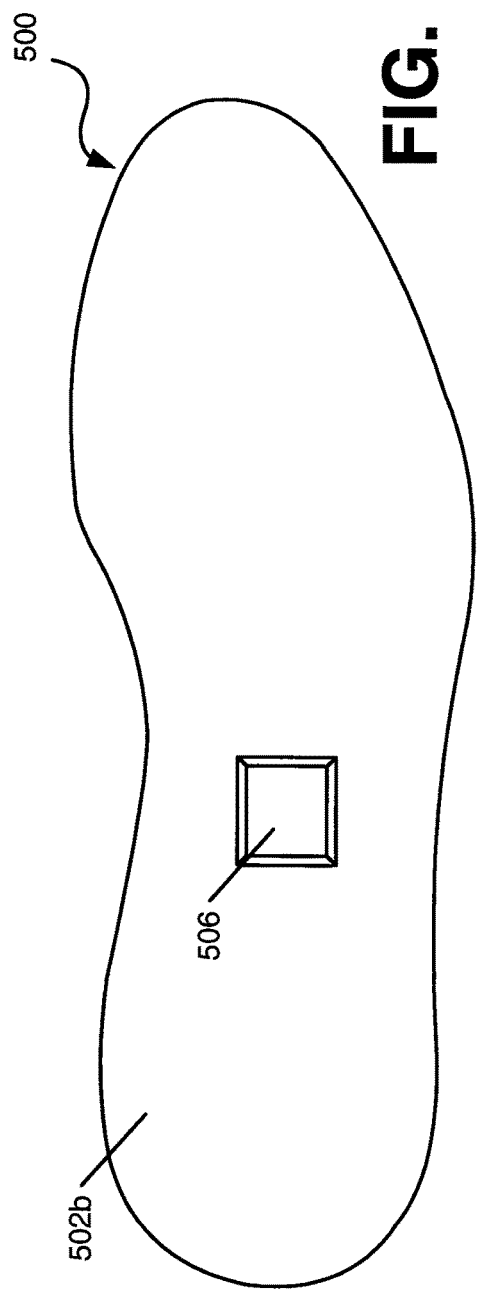
FIGS. 5A through 5C illustrate portions of example articles of footwear including an athletic performance sensing module or other device in a first position in accordance with some examples of this invention.
Figure 5B:
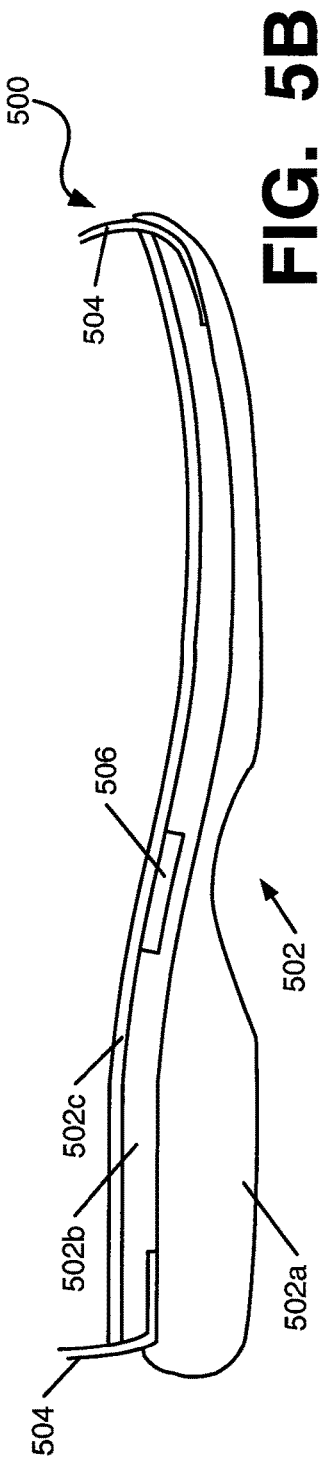

FIGS. 5A and 5B illustrate a partial view of one example of an article of footwear 500 that may be used in accordance with at least some examples of this invention. As shown, the article of footwear 500 includes a sole structure 502 engaged with an upper member 504. Any desired materials and construction of the upper member 504 and sole structure 502 may be used without departing from this invention, including conventional materials and constructions that are known and used in the art. In this illustrated example, as is common with athletic footwear, the sole structure 502 includes an outsole member 502a (e.g., for directly contacting the ground and providing traction, e.g., made of rubber, polymers, leather, combinations thereof, etc.), an impact-attenuating midsole member 502b (e.g., for attenuating ground or other contact surface impact forces, e.g., made from polyurethane foam, ethylvinylacetate, phylon, phylite, or the like), and a comfort-enhancing insole member, sock liner, or bootie element 502c. Of course, the various portions of the sole member 502 and the upper member 504 may be constructed from any desired number of pieces or parts, and these members, pieces, and/or parts may be engaged with one another in any desired manner, such as via cements, adhesives, stitching, mechanical connectors, and the like. Additionally, any desired closure system to help hold the article of footwear 500 on a wearer's foot may be used without departing from this invention, including, for example, laces, buckles, straps, hook-and-loop fasteners, mechanical fasteners, expandable elastic elements, and the like.

FIG. 5A illustrates a top-down view of the midsole element 502b according to this example of the invention. As shown in this figure, as well as in FIG. 5B, the midsole element 502b of this example structure 500 includes a hole into which a housing member 506 for receiving an electronic module is fit. The housing 506 in this example structure 500 is located in the middle arch or midfoot region of the article of footwear 500. While the housing 506 may be located in a variety of positions without departing from the invention, preferably it will be provided at a position and orientation and/or otherwise structured so as to avoid or minimize contact with and/or irritation of the wearer's foot, e.g., as the wearer steps down in and/or otherwise uses the article of footwear 500 (e.g., for an athletic performance).

Other features of the footwear structure 500 may help reduce or avoid contact between the wearer's foot and the housing 506 (or an element received in the housing 506) and improve the overall comfort of the footwear structure 500. For example, as illustrated in FIG. 5B, the insole member, sock liner, or bootie element 502c of the article of footwear 500 may fit over and at least partially cover the housing 506, thereby providing a layer of padding between the wearer's foot and the housing 506. Additional features for reducing contact between and modulating any undesired feel of the housing 506 at the wearer's foot will be described in more detail below, e.g., with reference to FIGS. 9A through 9C. This footwear interior housing arrangement is advantageous because the insole member 502c and the wearer's foot can reliably hold an electronic module or other object in the housing 506 during storage and/or use of the article of footwear 500, but access to the housing 506 remains readily available, e.g., for module or other element insertion, removal, exchange, etc.

Figure 5C:
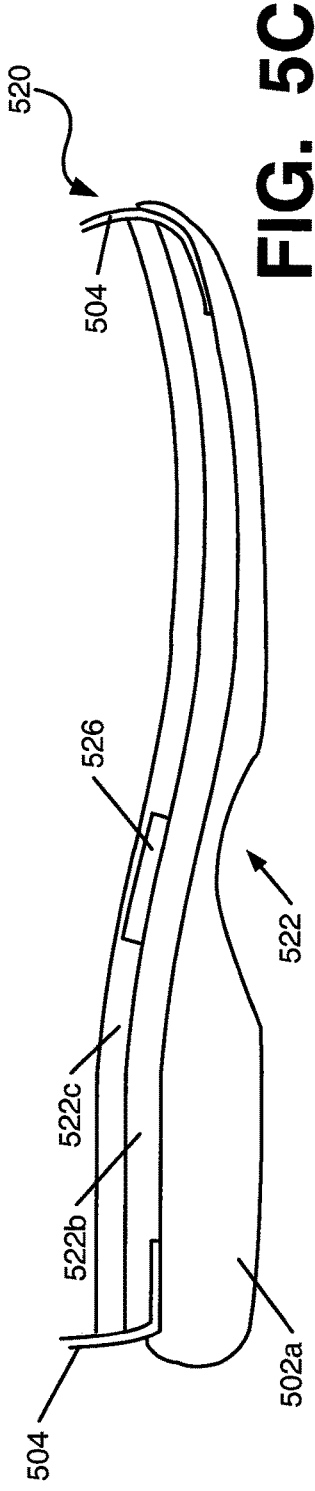

Housing members for electronic modules also may be provided as part of an insole member, sock liner, or interior footwear bootie member structure without departing from this invention. FIG. 5C illustrates a partial view of an example of such an article of footwear 520. While similar to the structure 500 illustrated in FIGS. 5A and 5B (and similar parts are labeled using the same reference numbers), in this illustrated example structure 520 of FIG. 5C, the sole structure 522 differs somewhat from that shown in FIGS. 5A and 5B. More specifically, in this example sole structure 522, the housing member 526 is provided (e.g., attached to, integrally formed as part of, etc.) as part of the insole member, sock liner, or bootie member structure 522c rather than as part of the midsole member 522b. While a wide variety of constructions are possible, in this illustrated example, the opening of the housing member 526 is located at the insole member, sock liner, or bootie member 522c bottom surface (i.e., adjacent the midsole member 522b). In this manner and with this illustrated structure 520, some portion of the insole member, sock liner, or bootie member structure 522c may remain between the user's foot and the housing member 526 to thereby modulate the feel of the housing member 526 at the user's foot. Access to the housing member 526 may be provided in a variety of ways, for example, by lifting the insole member, sock liner, or bootie member structure 522c away from the midsole structure 522b to expose its underside, by providing an access opening through the insole member, sock liner, or bootie member 522c (and optionally through the housing member 526), etc.

Of course, if desired, the opening to the housing member 526 may be provided through the top surface of the insole member, sock liner, or bootie member structure 522c without departing from the invention. Such a construction may be used, for example, when the housing 526 and/or electronic module include structures and/or are made from materials so as to modulate the feel at the user's foot, when additional comfort and feel modulating elements are provided, etc. Any of the various features described above that help reduce or avoid contact between the wearer's foot and a housing (or an element received in the housing) and improve the overall comfort of the footwear structure may be provided without departing from this invention, including the various features described above in conjunction with FIGS. 5A and 5B, as well as those described in more detail below, e.g., with reference to FIGS. 9A through 9C.

As still another example, if desired, portions of a housing member may be provided in both the midsole member (e.g., members 502b or 522b) and the insole member, sock liner, or bootie member structures (e.g., structures 502c or 522c) without departing from this invention (e.g., such that the electronic module or fill element is sandwiched or contained between adjacent portions of the housing structure). A wide variety of relative arrangements of the housing member with respect to one or more of the midsole member, insole member, outsole member, and/or upper member in an article of footwear are possible without departing from this invention.

Figure 6A:
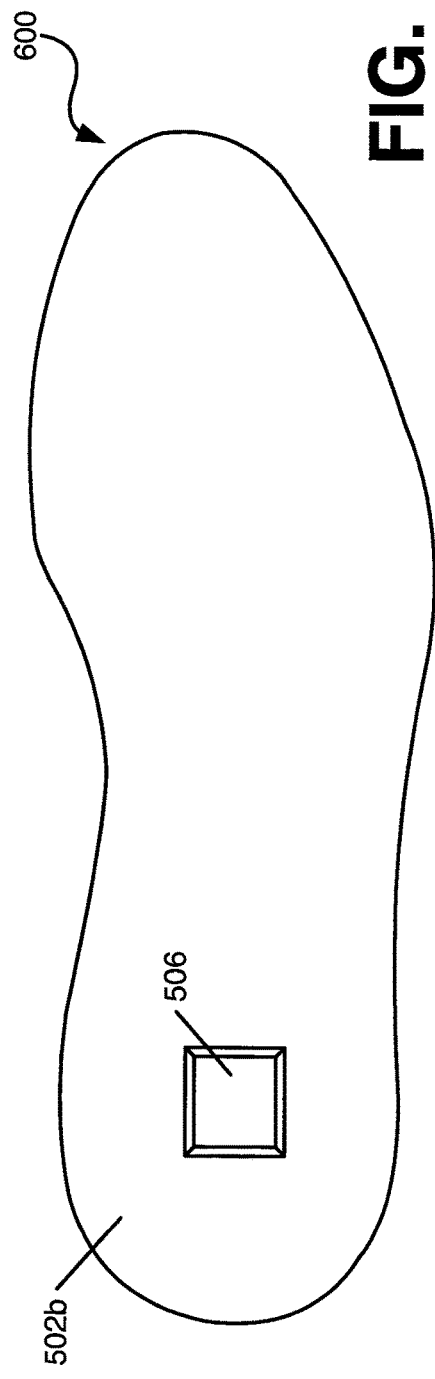
FIGS. 6A through 6C illustrate portions of example articles of footwear including an athletic performance sensing module or other device in a second position in accordance with some examples of this invention.
Figure 6B:
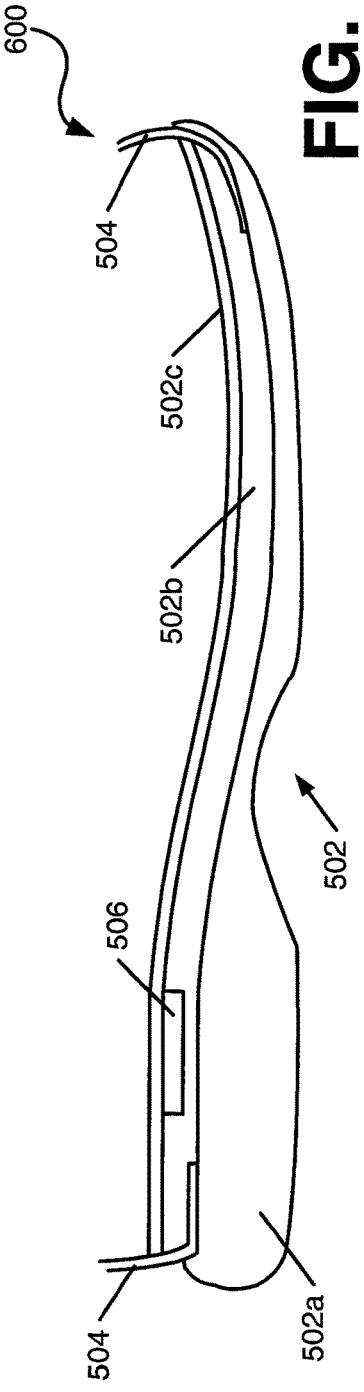

Housings 506 and/or 526 can be provided in a wide variety of different locations in the interior of a footwear structure 500 without departing from this invention. FIGS. 6A and 6B illustrate another partial view of an example footwear structure 600 in which the housing 506 is provided in the heel area. While the same basic footwear structure 600 is shown in FIGS. 6A and 6B as that shown in FIGS. 5A and 5B, those skilled in the art will appreciate, of course, that wide variations in the overall footwear structure, construction, and materials may be made without departing from this invention. Again, in the example structure 600 shown in FIGS. 6A and 6B, the insole member or sock liner 502c of the article of footwear 600 fits over and at least partially covers the housing 506, thereby providing a layer of padding between the wearer's foot and the housing 506.

Figure 6C:
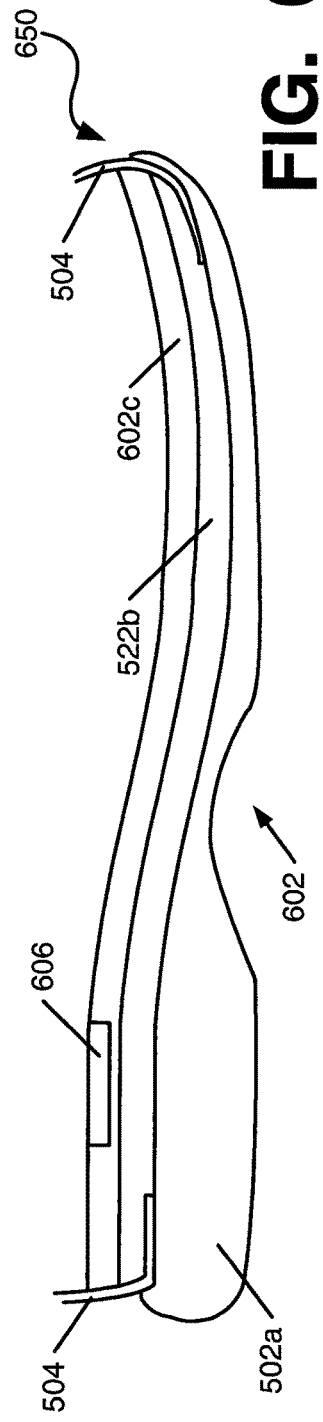

FIG. 6C illustrates another partial view of an example footwear structure 650 similar to those shown in FIGS. 5A through 6B. In this example structure 650, however, the housing 606 is provided as part of an overall sole structure 602 in the heel area of the footwear structure 650 and also as part of the insole member, sock liner, or bootie member structure 602c. In this example structure 650, the opening to the housing 606 is provided through the upper surface of the insole member, sock liner, or bootie member structure 602c. If necessary or desired, the housing 606 and/or electronic module may include structures and/or may be made from materials so as to modulate the feel at the user's foot. Additionally or alternatively, if desired, additional comfort and feel modulating elements may be provided. Any of the various features described above that help reduce or avoid contact between the wearer's foot and a housing (or an element received in the housing) and improve the overall comfort of the footwear structure may be provided without departing from this invention, including the various features described above in conjunction with FIGS. 5A and 5B, as well as those described in more detail below, e.g., with reference to FIGS. 9A through 9C. As still another alternative, if desired, access to the housing 606 may be provided via the bottom surface of the insole member, sock liner, or bootie member structure 602c, e.g., in a manner similar to that described above in conjunction with FIG. 5C.

Figure 7:
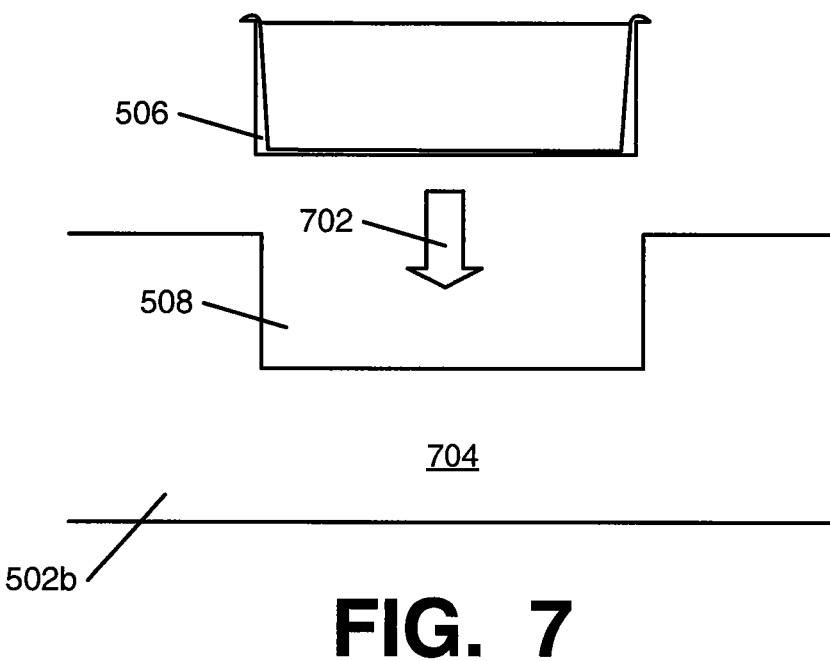
FIG. 7 illustrates an example procedure for forming a housing for an electronic module or other device in an article of footwear.

FIG. 7 generally illustrates an example method for providing a housing member 506 in an article of footwear, e.g., of the various types illustrated in FIGS. 5A through 6B. As shown, a midsole element 502b for interior and/or exterior use in an article of footwear is provided, e.g., formed of any desired material, such as impact-attenuating materials like rubber, polymeric materials (e.g., polyurethane, ethylvinylacetate, phylon, phylite, foams, etc.), and the like, and this element 502b may be made of any desired thickness and/or of varying thicknesses over its surface area. A hole or recess 508 is formed in the midsole element 502b. This hole or recess 508 may be formed at any desired time in the overall midsole element 502b and/or article of footwear manufacture process, such as during molding of the midsole element 502b, before the midsole element 502b is incorporated into a footwear structure, after the midsole element 502b is incorporated into a footwear structure, etc. Additionally, the hole or recess 508 may be formed in any desired manner, such as by molding it in to the midsole structure 502b, by cutting techniques, by rolling or pressing techniques, by laser ablation or laser cutting techniques, by heating techniques, etc.

Next, as shown in FIG. 7, the housing member 506 may be fit into and secured in the hole or recess 508 (as indicated by arrow 702). Any desired manner of securing the housing member 506 in the hole or recess 508 may be used without departing from this invention, including, for example, the use of adhesives, cements, or other fusing techniques; the use of mechanical connectors or other retaining elements; etc. The housing member 506 may be fit into the hole or recess 508 at any desired time in the overall midsole element 502b and/or article of footwear manufacturing process, including at any of the times mentioned above.

The housing member 506 may be made from any desired material(s) and/or in any desired number of pieces without departing from the invention, including, for example: from rigid plastic or polymeric materials, such as PEBAX® (a polyether-block co-polyamide polymer available from Atofina Corporation of Puteaux, France), thermoplastics, and the like; from metal materials; from ceramic materials; from fiberglass materials; from carbon fiber or other fiber materials; from combinations of different materials; etc. As additional examples, if desired, the housing member 506 may be made from a somewhat flexible material so that it may deform, at least somewhat, under force, such as the force produced when a footwear wearer steps down, lands a jump, etc.; such as the force applied as an electronic module and/or other element is inserted therein and/or engaged therewith; etc. As shown in FIG. 7, in this illustrated example, the midsole element 502b includes impact-attenuating material 704 directly beneath the housing member 506, e.g., to enable impact forces applied to the housing member 506 to be attenuated.

Of course, a wide variety in structures of the various elements, methods of making these elements, and overall constructions are possible without departing from this invention. For example, if desired, the midsole element 502b may include an opening completely through (e.g., material 704 may be absent), and the housing element may be made to include, mounted on, or otherwise engaged with an impact-attenuating material (e.g., an impact-attenuating material included as part of the housing member 506 or engaged with housing member 506 to take the place of some or all of material 704). As another example, if desired, the midsole element 502b may be made from multiple pieces, and one piece may be constructed to include the housing member 506 and/or a housing member assembly (optionally an assembly including a housing member 506 and an impact-attenuating material, e.g., attached at its bottom surface) may be provided between individual pieces of the midsole element 502b.

Figure 8:
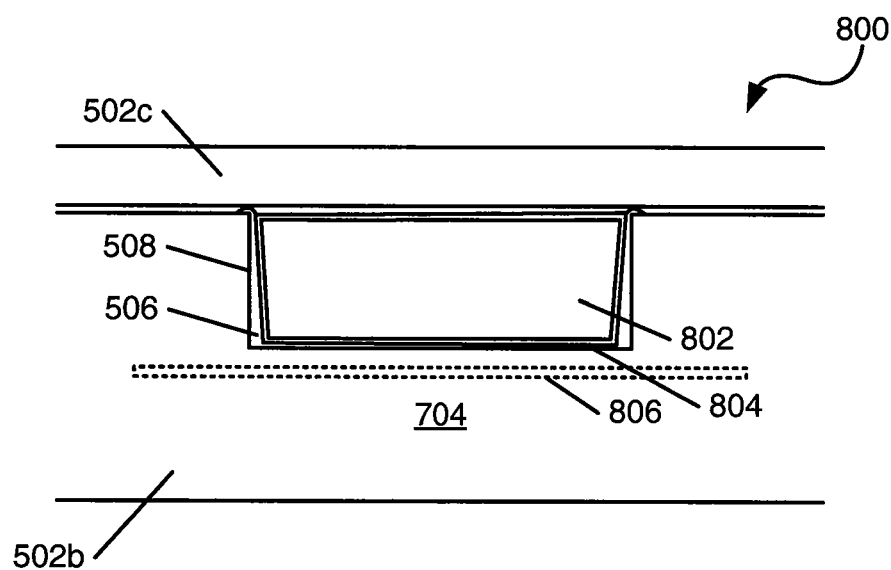
FIG. 8 illustrates a portion of an example article of footwear including an electronic athletic performance measuring module or other device mounted therein.

FIG. 8 illustrates a view of an example final assembly 800 with the housing member 506 fit into the opening or recess 508 provided in the midsole element 502b, as shown in FIG. 7. Additionally, in this illustrated example assembly 800, the housing member 506 includes an element 802 received therein. A wide variety of different elements 802 may be provided in the housing member 506 without departing from this invention. For example, as described above in conjunction with FIGS. 1-4, the element 802 may constitute an electronic module (e.g., module 102) for measuring a physical or physiological parameter associated with use of an article of footwear containing the assembly 800 or sensors and/or components for various other uses, including, for example, the various uses described above in conjunction with FIGS. 1-4.

In some instances, however, the housing member 506 may not include an electronic module, e.g., of the various types described above (such as module 102). For example, in a retail or other sales environment, an article of footwear may be available (e.g., to users, resellers, purchasers, etc.) without the added expense or complication of an electronic module, physical and/or physiological parameter sensing capabilities, and/or athletic or other performance sensing capabilities. In such instances, to make the article of footwear "ready-to-wear," a manufacturer, marketer, seller, or others might include a non-electronic "blank" or "dummy" element in the housing 506 as element 802. The "blank" or "dummy" element may take on any desired form or shape, such as a rigid member (e.g., made of plastic, metal, ceramic, etc.), a deformable member (e.g., made of rubber or polymeric materials, such as foams or materials, like those used to make the midsole element 502b), or combinations of different materials. The blank or dummy element may at least help maintain a consistent and non-irritating feel for the shoe on the wearer's foot (e.g., to help prevent the wearer from feeling the open chamber of the housing 506, if the opening is exposed, etc.). The blank or dummy element may include any desired shape or structures, e.g., to allow it to be secured in and/or released from the housing 506, e.g., in the same manners as described in more detail below for electronic modules.

Other reasons may exist for placing a non-electronic blank or dummy element 802 in the housing 506. For example, shoes typically are marketed and used in pairs. If desired, only one shoe of the pair may be constructed to include structures for holding an electronic module 102 (e.g., the opening 508, housing 506, and/or element 802 therein (with the other shoe of the pair having a more conventional structure, without these features)). Alternatively, if desired, each shoe of the pair may include structures for holding an electronic module 102 (e.g., the opening 508 and housing 506), and a single electronic module 102 may be selectively mounted in either shoe with a non-electronic blank or dummy element 802 mounted in the other shoe. The ability to selectively mount the electronic module 102 in either shoe may be advantageous, in at least some instances, for various reasons. For example, when the electronic module 102 transmits data or information, e.g., to a remote device 110 carried by the user 104 (e.g., see FIG. 1) or at another location, transmission of the data or information to the remote device may be better from one shoe as compared to the other (e.g., depending on the side of the body or arm on which remote device 110 is located, depending on the location of transmission towers or other transmission means with respect to the user and/or the user's general movement direction, etc.).

As another example, if desired, different electronic modules may be mounted in the different shoes of the pair, and these modules may provide information relating to the same or different physical or physiological parameters, may be used to provide the same or different types of information to a remote system, may be used to provide information for controlling the same or different external devices, may provide different combinations of information and functions, etc. In this manner, if desired, a broader scope of functions may be performed and/or information may be provided to the user or others, and/or more reliable and/or redundant data or information may be made available during the course of the performance.

The bottom 804 of the housing member 506 as shown in FIG. 8 may be formed of a hard plastic (or other material) (e.g., the same material as that making up the remainder of the housing member 506), to help protect the element 802 in the housing member 506. Additionally or alternatively, if desired, a separate protection member 806 may be provided, e.g., in the midsole member 502b or other portion of the sole or shoe structure, to protect the element 802 from impact forces or the like (e.g., particularly if the bottom 804 of the housing member 506 is open or partially open, if bottom surface 804 is omitted, etc. Additionally or alternatively, if desired, the protecting member 806 may extend around the sides and/or top of the housing. Such a structure may be useful in situations to help contain and protect electronic and other devices included in the midsole element 502b or other portions of the foot-wear structure, such as activation systems, transmission systems, data processing systems, securing systems, authentication systems, and/or release systems of the various types described in more detail below.

Various ways of preventing or modulating user feel of the housing member 506 and/or the electronic module or other element 802 may be provided without departing from this invention. FIGS. 9A through 9C illustrate various example structures that may be used. In the example structure 900 illustrated in FIG. 9A, the insole member, sock liner, or bootie element 502c includes an extra thickness 902 of impact-attenuating material at the location of (and shaped to fit within) the top of the hole 508 and/or the housing member 506. While any desired material may be used for the extra thickness 902 of the insole member, sock liner, or bootie element 502c (including, for example, rubber, polymers (such as polyurethane foam, ethylvinylacetate, phylon, phylite, or the like), fabric materials, etc.), it may be the same material and continuous with the material making up the remainder of the insole member, sock liner, or bootie element 502c or it may be a different, separate material without departing from the invention (optionally attached with the insole member, sock liner, or bootie element 502c).

In the example structure 920 shown in FIG. 9B, on the other hand, an independent pad or cover element 922 is placed over the element 802 and between the element 802 and the insole member, sock liner, or bootie element 502c. The pad or cover element 922 may be made from any desired materials, such as foam or other impact attenuating materials, as described above. As another example, if desired, the cover element 922 may be made from a more rigid material, such as a plastic material (e.g., like that making up the housing 506), optionally with foam or other material applied to its upper and/or lower surfaces. While the illustrated pad or cover element 922 is shown as a separate and independent part that is shaped to fit in the opening of the hole 508 and/or housing member 506, if desired, the pad or cover element 922 may be made to attach to at least one of the housing member 506, the midsole member 502b, the element 802, and/or the insole member, sock liner, or bootie element 502c. Optionally, in at least some example structures 920, the cover element 922 may be engaged with (movably and optionally removably) at least one of the housing member 506 (on either of its interior and/or exterior surfaces), the midsole member 502b, and/or the element 802, e.g., in the various manners that cover elements are provided for battery chambers of various electronic devices, such as electronic games or other electronic equipment, such as cameras, audio and/or video recording devices, audio and/or video playback devices, etc.

FIG. 9C illustrates another example of a structure 940 including a cover element 942 over the hole 508, housing 506, and/or element 802. In this example structure 940, the cover element 942 has elongated sides 944 and 946 with gradually sloping surfaces that cover the housing 506. The cover element 942 may be fixed to the housing 506, midsole element 502b, and/or insole member, sock liner, or bootie element 502c (e.g., by mechanical connectors, adhesives, hook-and-loop fasteners, or the like), or it may be held in place by retaining elements (e.g., like retaining grooves 948 that engage ridges 950 provided on the upper surface of the housing 506. Other ways of engaging the cover element 942 in the overall structure 940 are possible without departing from the invention. Of course, the cover element 942 may be made from multiple pieces, if desired, without departing from the invention. Also, if necessary or desired, an additional fill material may be provided, e.g., between the cover element 942 and the element 802 and/or between the cover element 942 and the insole member, sock liner, or bootie element 502c (e.g., positioned like material 922 in FIG. 9B). This additional material, optionally, may be integrally formed with, attached to, or separate from the cover element 942. The cover member 942 also may be made from any desired material, such as a rigid material (e.g., plastics, metals, etc.), impact-attenuating materials, fabric materials, and the like, without departing from the invention. The flexibility of the typical midsole element 502b and insole member, sock liner, or bootie member structure 502c can be relied upon in at least some structures 940 to fill in the areas between these members (e.g., toward the elongated sides 944 and 946 of the cover element 942). Alternatively, if desired, the cover member 942 may be made from a flexible material or at least somewhat flexible material and simply laid in place over the housing 506 and element 802, optionally relying on a user's weight and/or grooves 948 (or other structures) to hold it in place.

Figure 10A:
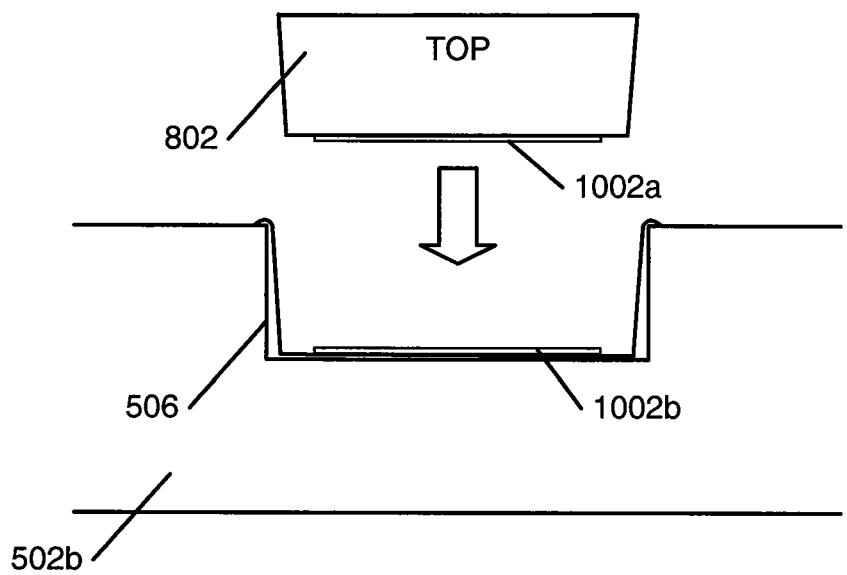
FIGS. 10A and 10B illustrate various asymmetric features of electronic modules and housings therefor in accordance with some examples of this invention.

FIG. 10A illustrates additional example features that may be present in at least some examples of footwear systems, performance sensing systems, and methods in accordance with this invention. As illustrated in FIG. 10A, the element 802 (e.g., an electronic module of the various types described above, a non-electronic blank or dummy element, etc.) may be received in the housing 506, and if desired, some means may be provided for securing the element 802 in the housing 506 (optionally, if desired, gravity, the weight or fit of the insole member or sock liner, and/or the weight of the user may be relied upon alone to secure the element 802 in the housing 506 without separate structures for holding the element 802 in place with respect to the housing 506). While various example securing structures will be described below, in this illustrated example, the bottom of the element 802 and the bottom of the housing 506 include mating hook-and-loop fastener elements 1002a and 1002b, respectively, that help releasably hold the element 802 in place with respect to the housing 506. Alternatively, if desired, adhesives, cements, epoxies, or the like may be used, e.g., optionally to permanently mount the element 802 in the housing 506, without departing from this invention. Optionally, if desired, the element 802 may include a handle or other element (e.g., at its top) to assist in its placement in and/or removal from the housing 506 chamber.

Figure 10B:
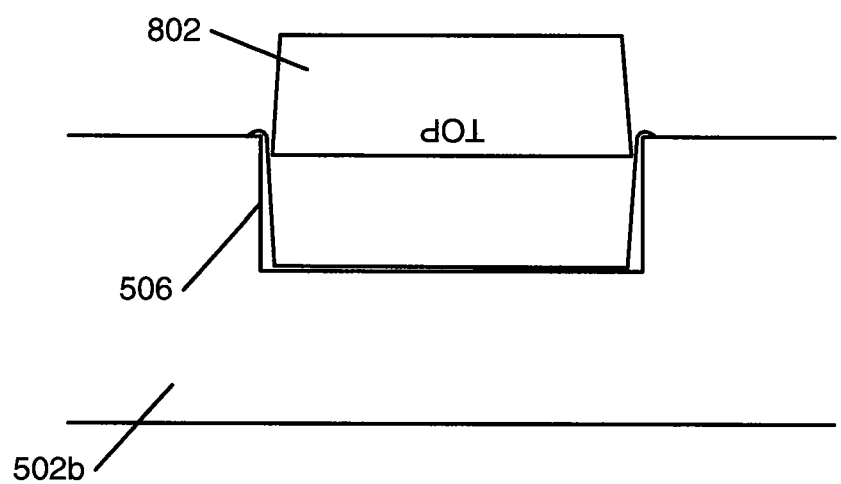

FIGS. 10A and 10B illustrate still additional features that may be available in at least some example systems and methods according to this invention. As illustrated in these figures, the receptacle of the housing member 506 and the element 802 (e.g., an electronic module of the various types described above, a non-electronic blank or dummy element, etc.) may be geometrically asymmetrical in at least one direction (e.g., from the top to the bottom direction) such that the element 802 will fit in the housing member 506 in a limited number of orientations (in some examples, in only one orientation). In the example of FIGS. 10A and 10B, the upper perimeter of the housing member 506 has a larger perimeter or circumference than its lower perimeter or circumference. Alternatively or additionally, if desired, the upper perimeter or circumference may be shaped different from the lower perimeter or circumference. In such structures, the element 802, when oriented in the manner shown in FIG. 10A, will easily slide into and fit into the chamber of housing member 506 (as shown, for example, in FIGS. 9A through 9C). When inverted, however, as shown in FIG. 10B, the sides of the element 802 will contact the sides of the housing member 506 before the element 802 is fully received within the chamber. In this manner, a user will immediately recognize (e.g., visually, due to discomfort in the foot, due to feel, etc.) that the element 802 is not properly mounted in the housing 506 and can take corrective action. This feature can be advantageous, for example, in situations where proper mounting of the element 802 in the housing member 506 can be necessary, for example, for power transfer, electrical contact, data transmission, data reception, activation, authentication, and/or other purposes (as also will be described in more detail below).

Figure 11A:
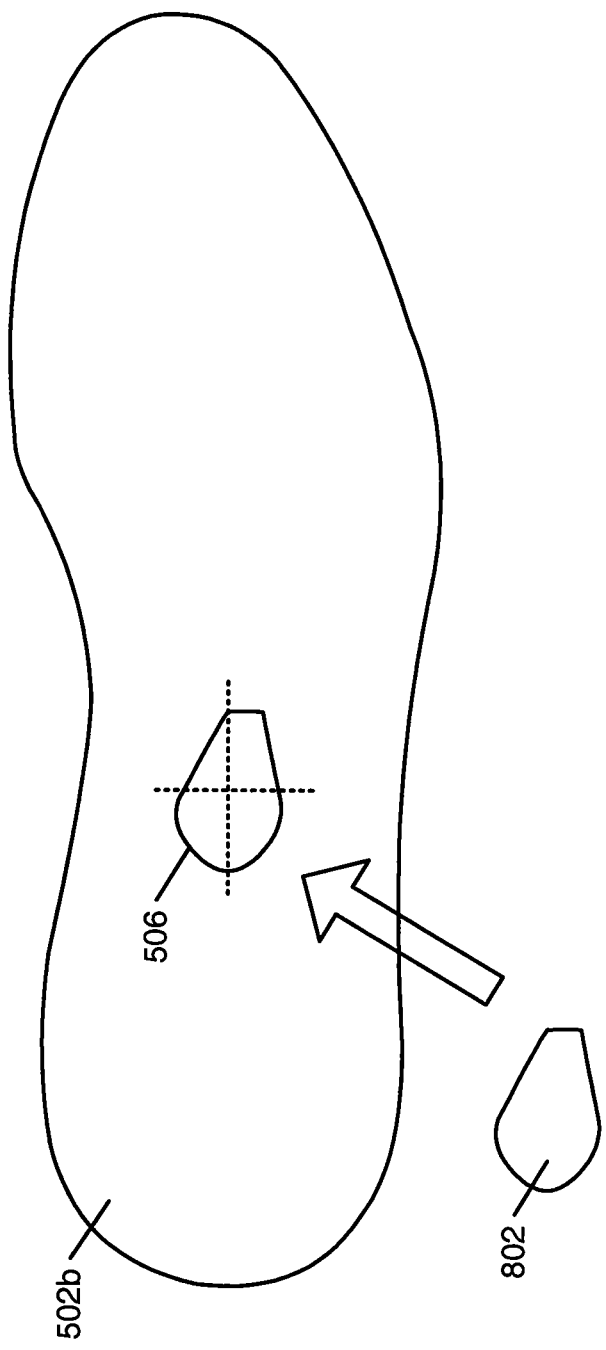
FIGS. 11A through 11C illustrate additional asymmetric features of electronic modules and housings therefor in accordance with some examples of this invention.
Figure 11C:
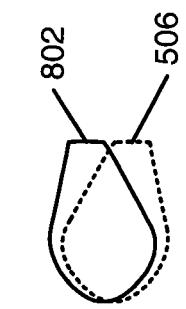
Figure 11B:
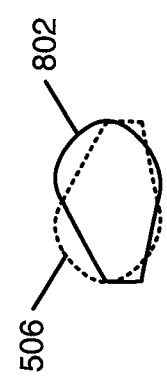

The housing 506 and element 802 (e.g., an electronic module of the various types described above, a non-electronic blank or dummy element, etc.) may be asymmetrical in other ways as well. For example, FIGS. 11A through 11C illustrate an example of an asymmetrical housing 506 and element 802 with an asymmetrical exterior perimeter to be received therein, again in a midsole structure 502b of an overall footwear structure. The element 802 will easily fit in the housing 506 in the orientation illustrated in FIG. 11A. In other orientations, however, as illustrated in FIGS. 11B and 11C, the element 802 does not fit in the housing 506. Depending on the exterior perimeter shape of the element 802 and the housing 506 opening, the element 802 may fit into the chamber in a predetermined number of orientations (e.g., one orientation for asymmetric perimeter shapes, two orientations for rectangular shapes, three orientations for some triangular shapes, four orientations for square shapes, etc.). Again, this feature can be particularly advantageous, for example, in situations where proper mounting of the element 802 in the housing member 506 is necessary, for example, for power transfer, electrical contact, data transmission, data reception, activation, authentication, and/or other purposes.

Of course, a wide variety of exterior perimeter and other shapes may be used to limit the number of orientations at which an element 802 will be accepted in a housing member 506 (e.g., to one, two, three, or four predetermined acceptable orientations). If desired, when two predetermined orientations are allowed (e.g., using a rectangular or triangular exterior perimeter shape), one predetermined acceptable orientation might place the element 802 in an activated or ON condition (e.g., by providing electrical contact, as will be described in more detail below) and a second predetermined acceptable orientation might place the element 802 in a deactivated or OFF condition (e.g., by not providing electrical contact). This feature can be particularly advantageous, for example, to allow reliable storage of the element 802 within the housing 506 in an unactivated condition, e.g., for storage to prevent data transmission during airline travel, to reduce battery power consumption, to prevent data transmission during non-athletic performance or non-event use, etc. Additionally, storing the element 802 in the housing 506 even in this unactivated condition avoids any undesirable user feel of the empty housing 506 during use of the shoe and/or helps prevent loss or inadvertent failure to have the element 802 available for use.

Of course, a wide variety of other electronic module or other element 802 locations are possible without departing from this invention. FIGS. 12A and 12B illustrate another example footwear structure 1200 in which a housing 506 is formed at a medial posting location, e.g., in the heel area of the midsole element 502b. While in this illustrated example structure 1200 the element 802 is loaded into the housing 506 from the top of the midsole element 502b, if desired, the element 802 may be loaded into a housing member 506 formed as a pocket element in the side of the midsole element 502b or the outsole element 502a (as shown in broken lines at reference number 1202 in FIG. 12B). The pocket element 1202 may include an openable and securable cover, and it may be accessed from the footwear 1200 exterior. As will be explained in more detail below, the transmission system 106 may be included as part of the element 802 or separately provided (e.g., included as part of the sole structure 502, if desired).

While many of the same reference numbers and specific structures are used in FIGS. 12A and 12B as those used in various figures described above, those skilled in the art will appreciate, of course, that a wide variety of different upper member 504, sole member 502, and/or overall shoe structures constructions, materials, and construction methods may be used without departing from this aspect of the invention, including the use of conventional constructions, materials, and constructions methods that are known and used in the art.

Figure 13:
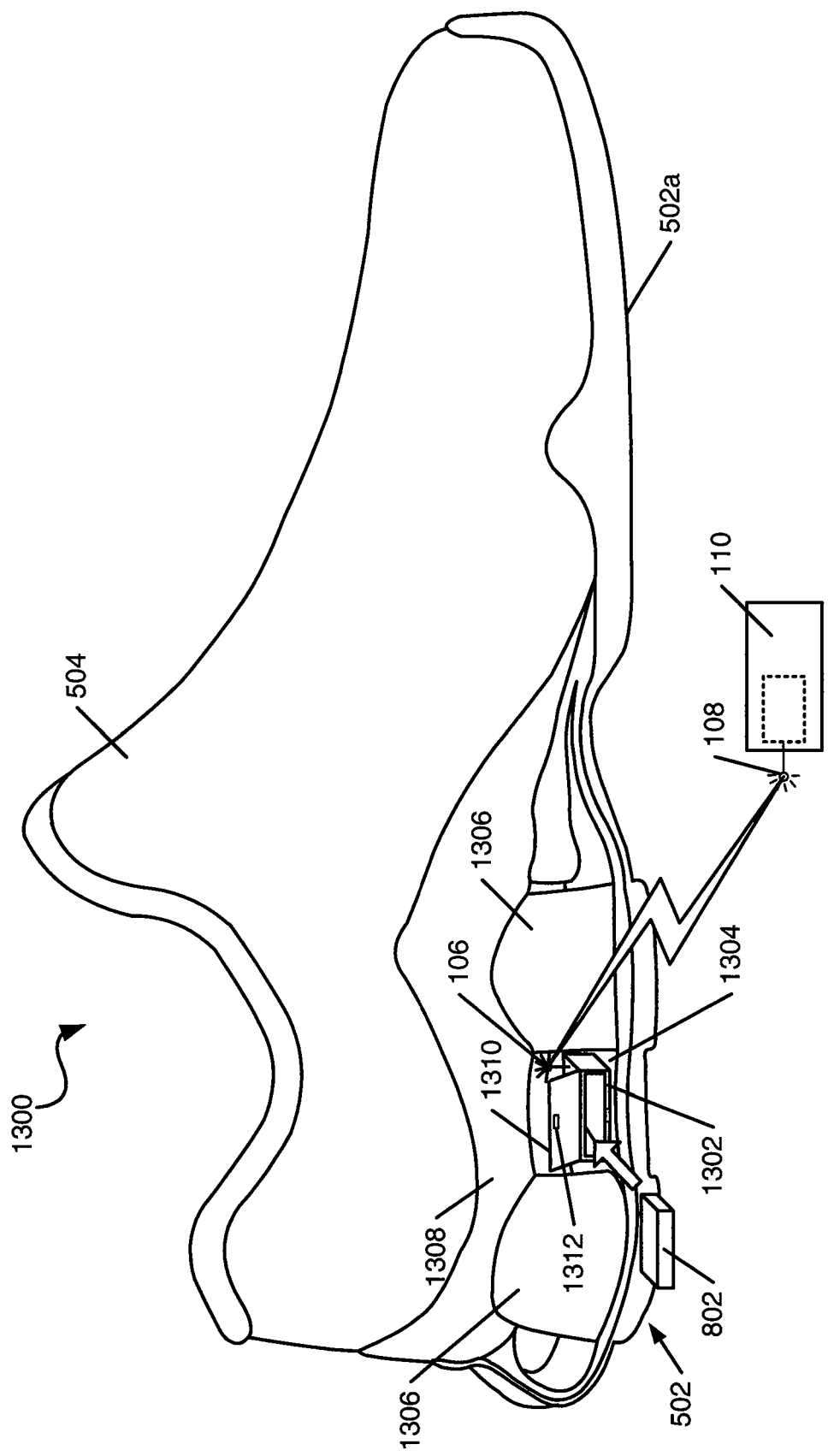
FIG. 13 illustrates an example article of footwear including an athletic performance sensing module or other device in an externally accessible position in accordance with some examples of this invention.

FIG. 13 illustrates another example footwear structure 1300 that may be provided in accordance with some examples of this invention. In this illustrated example structure 1300, the housing member 1302 for the element 802 (e.g., an electronic module) is provided and is accessible from the exterior of the footwear structure 1300. More specifically, in this illustrated example, the housing member 1302 is formed on a lower plate member 1304 of a footwear sole structure 502. This housing member 1302 is provided between plural impact-attenuating columns 1306 of the sole structure 502. This overall sole structure 502 is akin to those included in various footwear products available under the SHOX® trademark from NIKE, Inc. of Beaverton, Oregon, U.S.A. Of course, if desired, the housing member 1302 could be provided (or additional housing members 1302 could be provided) at other locations in the footwear structure 1300, such as on the underside of upper plate member 1308, in or on one of the impact-attenuating columns 1306, etc.

In the example structure 1300 illustrated in FIG. 13, the housing 1302 includes a cover member 1310 movably or removably engaged therewith. The cover member 1310 may be secured, e.g., to the housing 1302, the lower plate member 1304, or other portion of the structure 1300 in any desired manner without departing from the invention, including, for example, a hook-and-loop fastener arrangement; a clamp, clasp, hinge, or other mechanical fastener arrangement; an adhesive, cement, weld, or other fusing techniques; etc. This cover fastening arrangement is generally represented in FIG. 13 at reference number 1312, which in this illustrated example constitutes a hook-and-loop type fastener. Additionally, by structures that will be described in more detail below, in this example structure 1300, the data transmission system 106 is at least partially separate from the element 802, and in this illustrated example, it forms part of the housing member 1302.

Figure 14:
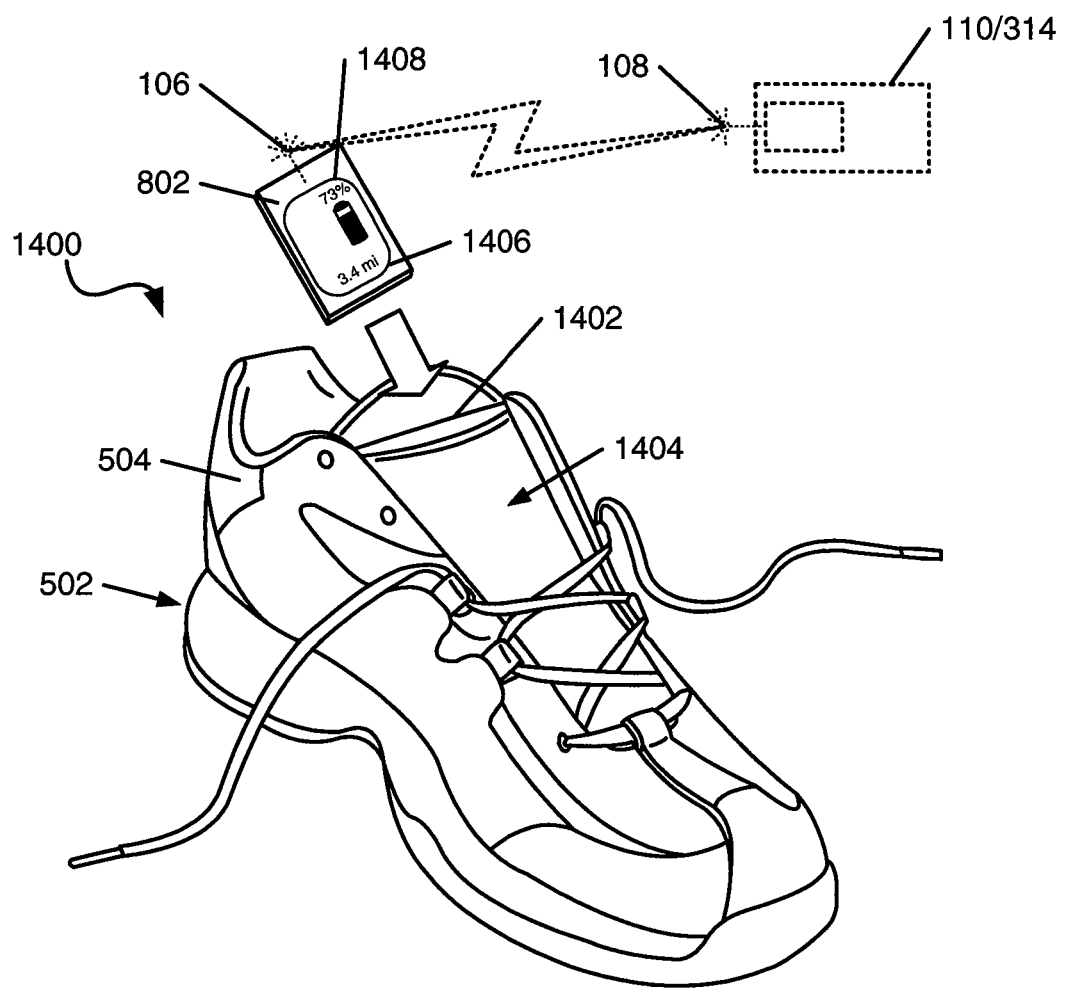
FIG. 14 illustrates an example article of footwear including an athletic performance sensing module or other device engaged with a portion of an upper member in accordance with some examples of this invention.

FIG. 14 illustrates still another example footwear structure 1400 including a system for mounting an electronic module 802. In this example structure 1400, rather than mounting in the sole structure 502, the electronic module 802 is mounted as part of the upper member structure 504. Even more specifically, in this example footwear structure 1400, the electronic module 802 is mounted in a pocket type housing 1402 provided with or defined in or on the tongue element 1404 of the article of footwear 1400. While a simple fabric type pocket member 1402 is illustrated in FIG. 14, if desired, the pocket member 1402 may have some or all of the various features of the housing member 506 described above (and/or those that are described in more detail below), such as, for example: a rigid or relatively rigid construction or shape; an asymmetric mounting opening that will accept the module 802 in a limited number of orientations (e.g., one, two, three, four, etc.); separate power source and/or data transmission/reception capabilities (e.g., as will be described in more detail below); activation/authentication capabilities (e.g., as will be described in more detail below); etc. The material of the remainder of the tongue member 1404 (e.g., a soft, thick fabric and/or foam containing material) on which the pocket member 1402 is defined or engaged, can be made sufficiently thick to prevent or modulate user feel or discomfort when the module 802 is present and/or if the housing 1402 is rigid or relatively rigid.

Additional potential features of aspects of the invention are illustrated in FIG. 14. Like the various systems and methods described above, if desired, the electronic module 802 may transmit data to and/or receive data from a remote system 110/314, e.g., via wireless transmission or other data transmission capabilities, as shown by transmission/receiver elements 106 and 108. This is not a requirement. Rather, if desired, the electronic module 802 may include a display 1406 that can provide any desired information to the user, such as information relating to the athletic performance, measured physical or physiological data or information, etc. This module 802 also can control other components, such as active impact-attenuating elements. While any type of information may be measured by and/or provided to and/or sent from the electronic module 802, in the illustrated example, the module 802 provides at least distance traveled (e.g., pedometer-based) information. Also, as illustrated in FIG. 14, the module 802 may provide remaining battery life information (see the example battery life icon 1408). Of course, if desired, a module 802 of the type illustrated in FIG. 14 may be used in any of the systems described above, and if desired, the use of transmission and/or remote display or other devices may be avoided.

The tongue location, e.g., as illustrated in FIG. 14, can be desirable for a variety of reasons. For example, locating the electronic module 802 at the tongue 1404 allows for easy access to the module 802, e.g., for module insertion, removal, exchange, ON/OFF switching, etc. (more specifically, a user does not need to remove his/her shoe completely and/or remove or move the shoe's insole member or sock liner to obtain access to the housing 1402 or the module 802). Additionally, the tongue location can provide better antenna transmission for data exchange with a remote system, e.g., systems 110 or 314 (more specifically, transmission and/or reception capabilities are not blocked and/or attenuated by the sole structure, the user's foot, etc.).

C. Electronic Module Connection Features

In many of the example structures above, the housing member, as well as various parts of the shoe structures, have been passive, i.e., they generally simply receive the electronic modules 102 and do not perform any data transmission, transfer, and/or processing functions. In other words, in at least most of these structures (e.g., with the exception of the structures shown in FIGS. 13 and 14), the electronic module 102 and/or 802 housed the power supply and/or all components necessary to perform the data collection, processing, transmission, and/or reception functions. This is not a requirement. FIG. 15A illustrates an example structure 1500 in which some portion of the sole structure 502 contains or houses at least some portions of a data transmission/reception system 1502 (e.g., akin to element 106 in FIG. 1) with an antenna member 1504 extending between and/or along side elements of the sole structure 502, e.g., to be exposed at the shoe exterior. Of course, if desired, the antenna member 1504 need not extend to the shoe's exterior (assuming that the data carrier waves can penetrate into the shoe structure 1500 to reach an internal antenna). The transmission/reception system 1502 may connect with an electronic module 102 mounted in the housing member 1506 via connections made through the housing member 1506, examples of which will be described in more detail below. The transmission/reception system 1502 can communicate with a remote system 1508 (e.g., like systems 110 and/or 314 described above) through any suitable or desired protocol, including conventional systems, methods, and protocols that are known and used commercially. If desired, the antenna member 1504 may extend to and form a portion of the exterior of the sole structure 502, e.g., fashioned as a decorative element provided in, on, and/or along some portion of the sole structure 502.

Additionally or alternatively, if desired, some portion of the sole structure 502 may include at least some portion of a power supply 1510 that supplies power for operating one or more components of the electronic module 102, the transmission/reception system 1502, and/or other processing systems. The power supply 1510 may connect with the electronic module 102 mounted in the housing member 1506 via connections made through the housing member, as will be described in more detail below. If desired, the sole structure 502 may include an access window to the power supply 1510 location, e.g., to allow insertion or exchange of a battery member, etc.

FIG. 15B shows a structure 1520 similar to that shown in FIG. 15A, but in this instance, the antenna member 1522 extends to and/or forms part of the upper member structure 504. If desired, the antenna member 1522 may be shaped and located so as to provide suitable communications with a remote system 1508. Moreover, if desired, the antenna member may form at least a portion of a decorative pattern in or on the upper member structure 504, and/or it may be wholly or partially contained in or covered by, if desired, e.g., a thin layer of fabric, plastic, or other material (e.g., upper member material), provided the covering material is permeable to the signal carrier waves for data transmission and reception in this system 1522.

Figure 16:
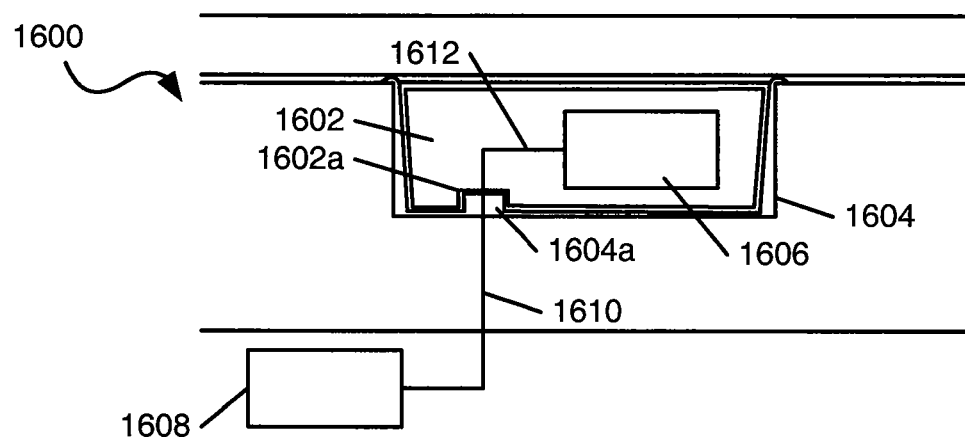
FIGS. 16-19 illustrate various example features and structures for activating, powering, and providing electrical communications with a module mounted in a housing member.

FIG. 16 illustrates an example electrical connection structure 1600 that may be used between an electronic module 1602 mounted in a housing member 1604 and other electronic components, e.g., of the types described above. These connections may be used, for example, to provide electrical communication between components 1606 included as part of the electronic module 1602 and components 1608 included as part of the footwear structure (e.g., in or on a sole structure, in or on an upper structure, etc.), such as a power supply, a transmission/reception system, etc. More specifically, in this illustrated example, the housing member 1604 includes a raised element 1604a that engages with a receptacle 1602a defined in the electronic module 1602. The raised element 1604a may include one or more electrical conductors 1610 that extend to component 1608. Likewise, recessed receptacle 1602a may include one or more electrical conductors 1612 that extend to component 1606. Electrical contact between conductors 1610 and 1612 at the raised element 1604a and receptacle 1602a junction can be used for various purposes, such as to transfer power, to transmit/receive data (including data sensed by sensors included in module 1602), and/or other purposes. Of course, the electrical connection at this junction may be made in any desired manner using any desired structures, including structures that are conventionally known and used for making connections between electronic devices, such as pins, contact pads, and the like.

Of course, if desired, any number of junctions (e.g., recess receptacles 1602a and raised elements 1604a) may be provided and each receptacle/raised element pair may include any desired number of contacts without departing from this invention. Also, if desired, the recessed receptacles 1602a and raised elements 1604a may be omitted and electrical contacts, pins, pads, or other suitable structures may be provided directly in the housing member 1604 and/or the electronic module 1602 without departing from this invention. Also, if desired, one or more recessed receptacles 1602a, raised elements 1604a, and/or other electrical contact structures may be provided in the side and/or top walls of the housing 1604, the electronic module 1602, and/or any cover element, without departing from this invention.

As still additional examples, if desired, particularly when multiple contact locations are provided between a housing 1604 and an electronic module 1602, the locations and/or pattern of electrical conductivity in the various contact locations may be used to provide authentication information and/or other information to the electronic module and/or an associated data processing system. For example, processing systems on board the electronic module 1602 and/or the footwear structure 1600 may be looking for electrical contact at specific, predetermined locations and/or in a specific, predetermined pattern or order for the purpose of confirming that the electronic module 1602 is authorized for use in that specific shoe 1600. If electrical contact is not made in the expected locations or in the expected order, the electronic module 1602 (or at least certain functions thereof) may be deactivated. Additionally or alternatively, electrical contact at specific, predetermined locations and/or in a specific predetermined pattern or order over the plural electrical contacts may be used to provide information as to the type of shoe or the specific (right or left) shoe in which the electronic module 1602 is mounted, which information may be used in a data algorithm selection process (e.g., to tell the electronic module 1602 or other processing equipment the type of physical or physiological parameters to measure, to tell the module 1602 or other processing equipment the type of information to provide for display, to tell the module 1602 or other processing equipment the specific components to operate and/or the manner in which they should be operated, etc.).

Figure 17:
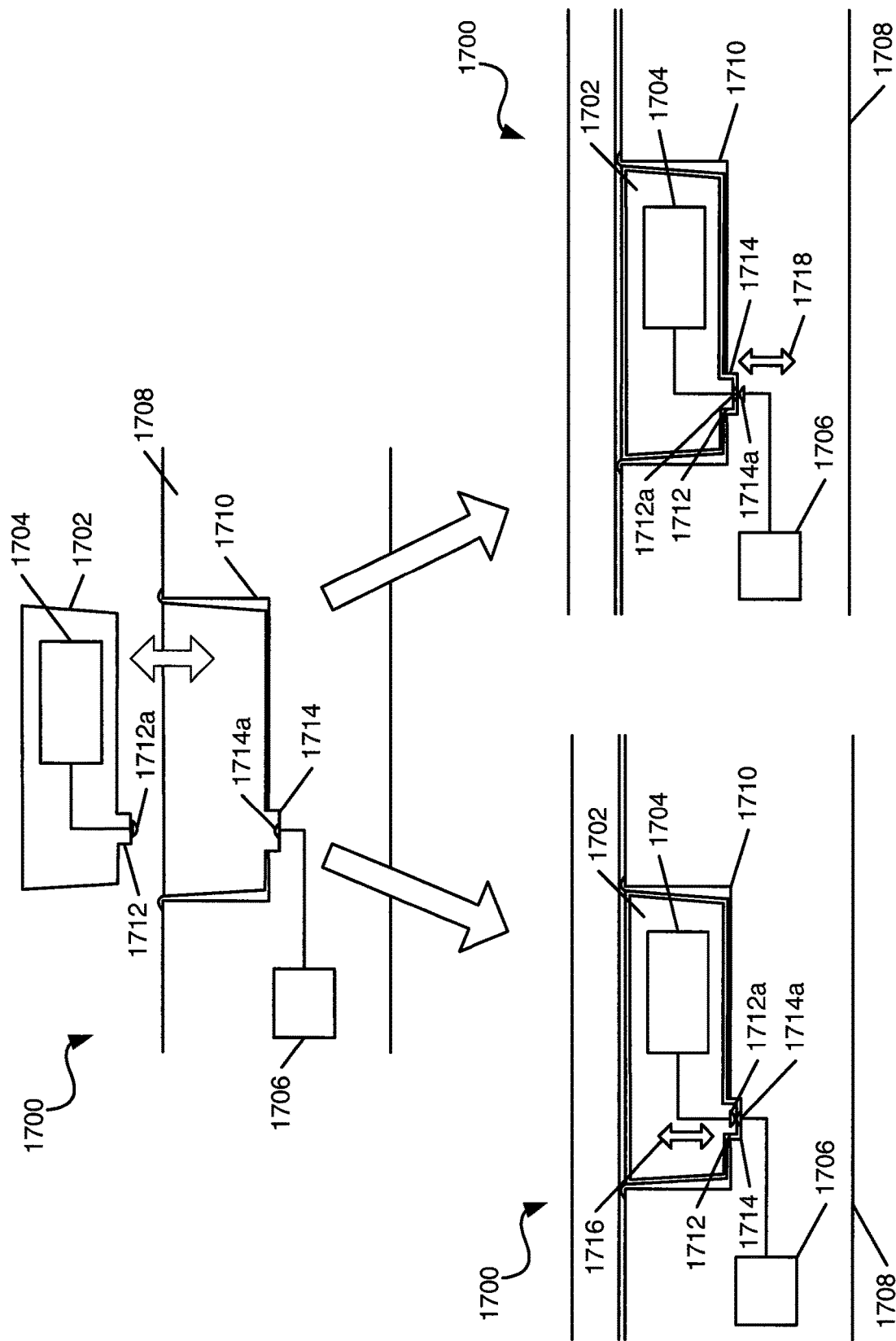

FIG. 17 illustrates additional examples of structures 1700 for providing and maintaining electrical contact and electrical communication between an electronic module 1702 (and one or more of its electronic components 1704) and electronic components 1706 included in an article of footwear 1708 through a housing member 1710. In this example structure 1700, the electronic module 1702 includes an extending portion 1712 and the housing 1710 includes an opening, recess, groove, or other discontinuity 1714. Any number of extending portions 1712 and/or corresponding openings, recesses, grooves, or discontinuities 1714 may be provided, and if desired, the housing 1710 may include one or more extending portions 1712 and the electronic module 1702 may include one or more of the openings, recesses, grooves, or discontinuities 1714. Also, if desired, a single opening, recess, groove, or discontinuity 1714 may receive more than one extended portion 1712 without departing from the invention. As still another example, if desired, the extended portions 1712 and the openings, recesses, grooves, or discontinuities 1714 may be omitted, if desired, and electrical contact may be provided in the manners described in more detail below, e.g., by providing the electrical contacts (e.g., pins, pads, receptacles, etc.) on surfaces flush or substantially flush or substantially flush with the remainder of the electronic module 1702 and housing 1710.

As shown in FIG. 17, the end of the extended portion 1712 in this example structure 1700 includes at least one electrical contact 1712a that extends outward somewhat from the end of the extended portion 1712. Similarly, the bottom of the opening, recess, groove, or discontinuity 1714 in this example structure 1700 includes at least one electrical contact 1714a that extends upward somewhat from the bottom of the opening, recess, groove, or discontinuity 1714. Electrical contact between components 1706 in the article of footwear 1708 (e.g., one or more of the power supply components, the data transmission/reception components, the data processing components, etc.) and components 1704 in the electronic module 1702 can be made via the contacts 1712a and 1714a, as shown in the bottom portions of FIG. 17 (i.e., when the electronic module 1702 is mounted in the housing 1710). If desired, the contacts 1712a and 1714a need not be raised from their respective surfaces, but rather, contact can be made with these contact elements 1712a and 1714a provided flush or substantially flush with their respective surfaces.

The structures 1700 illustrated in FIG. 17, however, can provide additional useful features in some examples of this invention. For example, when at least one of the contact elements 1712a and 1714a is raised up (as shown in the figures), it can be structured so as to move inward by contact with the other contact element (which may be stationary), and this movement of the contact element 1712a and/or 1714a can be used as a type of activation switch to turn the power supply and/or other electronic components on and off (and/or otherwise activate and disable the power supply or various components of the system). For example, in the example structure 1700 illustrated in the bottom left side of FIG. 17, the recess contact 1714a is stationary and the module contact 1712a is mounted in a movable manner (e.g., spring loaded, etc.) such that mounting the electronic module 1702 in the housing 1710 will cause the contact element 1712*a* to push upward somewhat into the module 1702 (see arrow 1716). This movement, if desired, can be used to activate an ON/OFF switch for the electronic module 1702 and/or enable or disable at least some functions of the electronic module 1702 (e.g., activate a power supply, activate transmission of data to/from the electronic module 1702 to/from the external components 1706, activate processing systems, etc.). Similarly, in the example structure 1700 illustrated in the bottom right side of FIG. 17, the electronic module contact 1712*a* is stationary and the recess contact 1714*a* is mounted in a movable manner (e.g., spring loaded, etc.) such that mounting the electronic module 1702 in the housing 1710 will cause the contact element 1714*a* to push downward somewhat into the shoe structure 1708 (see arrow 1718). This movement, if desired, can be used to activate an ON/OFF switch for the electronic components 1706 and/or enable or disable at least some functions of these components 1706 (e.g., activate a power supply, activate transmission of data to/from the electronic module 1702, activate processing systems, etc.). Of course, if desired, both contact elements 1712*a* and 1714*a* may be movable or may be stationary without departing from this invention. Additionally, if desired, as noted above, multiple contact elements 1712*a* and 1714*a* may be provided in the electronic module 1702 and/or associated with the housing 1710, and these various contact elements 1712*a* and 1714*a* may have any desired combination of fixation and movability without departing from this invention.

Figure 18:
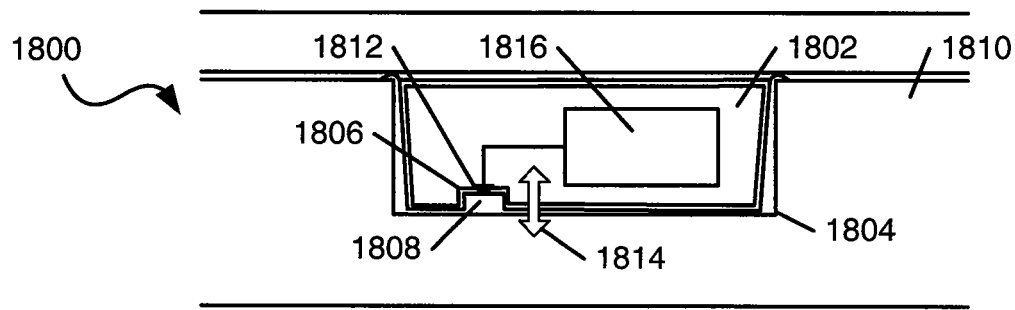

It is not necessary for an electronic module to make electrical contact through a housing member to components in the interior of an article of footwear to take advantage of various features of the extending portion and/or recesses, openings, grooves, and/or discontinuities of the types described above in conjunction with FIGS. 16 and 17. Rather, one or more extending portions and corresponding receiving recesses, openings, grooves, and/or discontinuities may be used as features simply to assure that an electronic module is correctly mounted in a housing (e.g., in a single predetermined orientation or in a predetermined number of different orientations), to activate the module or various components thereof (e.g., by activating an ON/OFF switch), and/or to provide authentication information, irrespective of whether the power source, transmission/reception components, antenna components, or the like are included as part of the overall shoe structure and/or as part of the electronic module structure. FIG. 18 illustrates an example of such a structure 1800. As shown in this figure, the structure 1800 includes an electronic module 1802 mounted in a housing 1804. The electronic module 1802 in this example structure 1800 includes an opening, recess, groove, or discontinuity 1806 that engages an extending portion 1808 provided, e.g., in the housing member 1804, as part of the shoe structure (e.g., the midsole element 1810), etc. Of course, if desired, the electronic module 1802 may include one or more extending portions 1808 and the housing 1804 or shoe structure (e.g., midsole element 1810) may include one or more corresponding openings, recesses, grooves, or discontinuities 1806 without departing from the invention. Also, if desired, plural extending portions and corresponding openings, recesses, grooves, or discontinuities may be provided, optionally either types of structures on both the electronic module 1802 and in the housing 1804 and/or other portions of the shoe structure (e.g., such that the locations of the extending portions and corresponding openings, grooves, recesses, or discontinuities provide a type of "key" structure to assure proper insertion of the electronic module 1802 in the housing 1804). Also, one or more of the extending portions 1808 and/or openings, recesses, grooves, and/or discontinuities 1806 may be provided in other walls of the electronic module 1802 and/or the housing member 1804 or shoe structure without departing from this invention.

While the extending portions 1808 and corresponding openings, recesses, grooves, and/or discontinuities 1806 may be "passive," e.g., simply to prevent mis-orientation of electronic modules 1802 and/or insertion of unauthorized modules, these structures may provide additional functions as well. For example, as illustrated in FIG. 18, the interior wall of the opening, recess, groove, or discontinuity 1806 of the electronic module 1802 may be equipped with a "switch" activating mechanism 1812. As generally described above in conjunction with FIG. 17, insertion of the electronic module 1802 into the housing 1804 may result in movement of or toggling of the switch activating mechanism 1812 (generally depicted by arrow 1814), which in turn can be used to activate or enable one or more functions of electronic components 1816 included in the module 1802. Accordingly, electrical connection need not be made across the housing/electronic module junction (as shown for example in FIG. 17) to make use of the general extending portion/corresponding openings, grooves, recesses, or discontinuities or "key" type structures described above.

Figure 19:
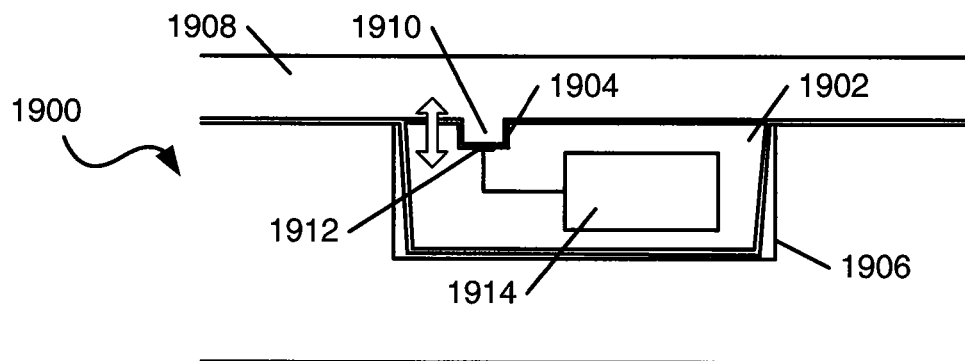

FIG. 19 illustrates another example structure 1900 including general extending portion/corresponding openings, grooves, recesses, or discontinuities or "key" type structures. In this example structure 1900, the electronic module 1902 again includes one or more openings, recesses, grooves, and/or discontinuities 1904. In this example structure 1900, however, there are no corresponding extending portions provided in the housing member 1906. Rather, the insole element or sock liner 1908 (or an element attached thereto, engaged therewith, or located over the module 1902) includes one or more extending portions 1910 that extend into the opening(s), recess(es), groove(s), and/or discontinuity(ies) 1904. Again, as described above in conjunction with FIG. 18, while the arrangement of FIG. 19 may be simply passive (e.g., to assure proper mounting of the electronic module 1902 in the housing 1906), the structure 1900 of FIG. 19 also may be used to activate a switching mechanism 1912 for electronic components 1914 (e.g., of the module 1902 or carried by the footwear) as described above in conjunction with FIG. 18.

Of course, combinations of the various electrical contact, activation, and authentication structures, systems, and methods of the types described in conjunction with FIGS. 16-19 may be used without departing from this invention. Additionally, the various electrical contact, activation, and authentication structures, systems, and methods of the types described in conjunction with FIGS. 16-19 may be used at various different positions on an article of footwear structure, such as at the various positions described above in conjunction with FIGS. 5A-6B and 12A-14, without departing from this invention.

Figure 20:
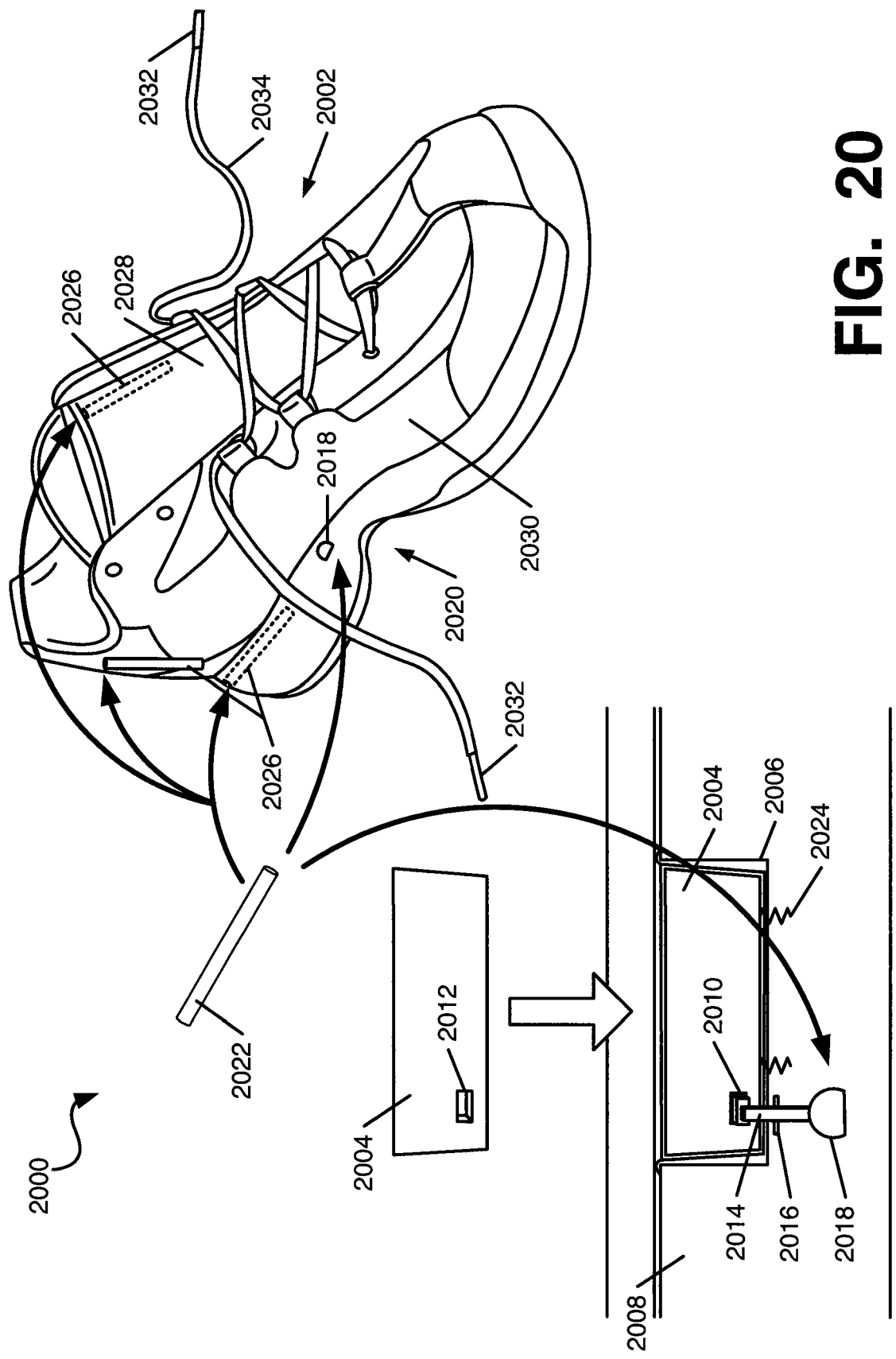

D. Selective Engagement, Release, Activation, and Authentication Systems and Methods Articles of footwear and footwear systems in accordance with at least some examples of this invention may have a variety of other features and/or combinations of features. FIG. 20 illustrates one example of a footwear structure and system 2000 that includes various additional features. FIG. 20 generally illustrates an article of footwear 2002 that includes an electronic module 2004 mounted in a housing member 2006, e.g., in the various manners described above (such as in the heel or arch area of a midsole member 2008), but this example system 2000 includes various module securing structures and release systems. Once an electronic module 2004 is mounted in an article of footwear 2002, it may be difficult to grab, e.g., when a user wishes to remove it, exchange it for another, replace batteries, etc., particularly if the module 2004 is secured in a rigid housing 2006, if it tightly fits in the housing 2006, and/or if its top surface is below the top of the housing 2006. FIG. 20 illustrates an example securing system and release system that may be used in conjunction with electronic modules 2004, e.g., of the various types described above.

In this illustrated example system 2000, the electronic module 2004 is held in place in the housing at least in part via a retaining member 2010 that extends into a mating chamber 2012 provided in the electronic module 2004 side wall. The retaining member 2010 may be spring biased and shaped so as to allow the module 2004 to easily slide into the housing 2006 while pushing the retaining member 2010 against the spring force, and then when properly positioned, the retaining member 2010 may "snap into" the chamber 2012 under the force of the spring. In this illustrated example, the retaining member 2010 further is mounted on a lever member 2014 that is movably mounted on a fulcrum member 2016. This structure can be used, at least in part, to securely hold the electronic module 2004 in the housing member 2006. Alternatively, if desired, an electronically controlled and/or activated retaining member 2010 may be used as opposed to this more mechanical arrangement.

The free end of the lever member 2014 (away from the retaining member 2010) in this example system 2000 is located adjacent an opening 2018 provided at an appropriate location to access a module release mechanism. In this instance, the opening 2018 is provided in the side of the sole structure 2020 of the shoe (e.g., in a midsole member 2008, in an outsole member, etc.). Additionally, a release tool 2022 is provided, an end of which can be inserted into the opening 2018. When the release tool 2022 is pushed into the opening 2018, it will engage the lever member 2014, which then will rotate about the fulcrum member 2016 to move the retaining member 2010 outside of the electronic module's retaining chamber 2012. If necessary or desired, one or more spring members 2024 (or other structures) may be provided to help push the module 2004 upward and out of the housing 2006 once the retaining member 2010 is moved out of the chamber 2012. This feature can help make it even easier for the user to remove the module 2004.

If desired, the release tool 2022 may be shaped so as to be received in the opening 2018 in one orientation (e.g., akin to a type of "key" mechanism). As illustrated in FIG. 20, a separate release tool 2022 may be provided, optionally storable along with the shoe, e.g., in a pocket element 2026 provided in the sole structure 2020, in the tongue element 2028, in the upper member 2030, or the like. As another option or alternative, if desired, the aglet 2032 for the shoelaces 2034 of the shoe 2002 may be used for the release tool. Optionally, if desired, at least the end portion of one or more of the aglets 2032 may be specially shaped to fit into the opening 2018 when the opening 2018 is specially shaped.

If desired, the lever member 2014 and retaining member 2010 may be included in the electronic module 2004, and a retaining chamber may be provided in the housing 2006. In such an arrangement, the opening 2018 may be provided in the electronic module 2004, and the release tool 2022 may interact with the release mechanisms included with the module 2004 rather in than the footwear structure. Again, if desired, electronically movable and/or activated securing and/or release mechanisms may be provided as opposed to these more mechanical structures.

Of course, a wide variety of different securing systems and/or release systems may be used without departing from this invention. FIGS. 21A and 21B illustrate another example structure 2100 that includes electronic module 2102 securing systems and/or release systems. In this example structure 2100, the electronic module 2102 again is mounted in the interior of the footwear structure (e.g., through an opening defined in a housing 2104 provided in a midsole element 2106). The electronic module 2102 tightly fits in the housing member 2104 and/or may be secured therein, e.g., using adhesives, hook-and-loop fasteners, other mechanical fasteners, detent mechanisms, flexible retaining elements (e.g., in the walls of housing 2104 that fit into small recesses provided in the electronic module 2102 or vice versa), etc. Once secured in the housing member 2104, as noted above, the electronic module 2102 can be difficult to grasp for removal purposes and may mot release under the force of gravity by simply turning the shoe upside down and/or shaking it (particularly if some type of restraining or securing system is utilized, e.g., like those described above).

The release mechanism in the example structure 2100 illustrated in FIGS. 21A and 21B includes a lever member 2108 provided within the midsole element 2106 or other portion of the shoe structure. This lever member 2108 is movably mounted on a fulcrum member 2110 such that it can rotate up and down. To release the electronic module 2102 from the housing member 2104, a release tool 2112 (e.g., of the various types described above) may be inserted into a release mechanism access opening 2114 provided in the midsole member 2106. A portion of the lever member 2108 may be engaged by the release tool 2112 and pushed downward, which causes the lever member 2108 to rotate about the fulcrum 2110. This action, in turn, causes the opposite end of the lever member 2108 to move upward. In this illustrated example, the opposite end of lever member 2108 includes an engaging element 2116 that is capable of extending upward through an opening 2118 defined in the housing member 2104 to engage the electronic module 2102 and push it upward, as shown in the progression of FIG. 21B. Once pushed upward, the electronic module 2102 can clear the top portion of the housing member 2104 and be readily available for the user to grasp (or fall out under the force of gravity). If desired, the lever member 2108 may be weighted and/or the fulcrum 2110 may be biased (e.g., spring biased) such that the engaging element 2116 will automatically return to a location outside the housing member 2104 when the force of the release tool 2112 is relaxed. Alternatively, if desired, a force applied to the engaging element 2116 inside the housing member (e.g., by a user's hand, by insertion of an electronic module 2102 or blank, etc.) may be used to return the engaging element 2116 to the position shown at the left side of FIG. 21B.

A wide variety of structures may be used to provide securing structures and/or release systems of the types illustrated by FIGS. 21A and 21B. As one example, if desired, as shown in these figures, the insole member or sock liner may include an opening that essentially overlaps with or aligns with the opening 2114 provided in the midsole element 2106. An opening of some sort also may be provided in the insole member or sock liner to allow removal of and access to the electronic module 2102. In this manner, the user can easily access and utilize the release mechanism without the need to remove the insole member or sock liner 2118. Alternatively, if desired, all or some portion of the insole member or sock liner 2118 may be removed to allow access to the opening 2114 and/or the housing member 2104. As still another example, if desired, the insole member or sock liner may include an opening defined therein that corresponds with the location of the module 2102, and the module 2102 may include a similar material to the insole member or the sock liner at its top surface (e.g., optionally attached thereto, laying over its top surface, etc.). In this manner, lifting of the electronic module 2102 under the force of engaging element 2116 can directly lift the electronic module 2102 and its covering material upward and out through the opening provided in the insole member or sock liner. In such an arrangement, it is not necessary for the user to remove the sock liner or insole member to remove the module 2102. Wide variations in the locations of the various elements, openings, and their specific structures also are possible without departing from this invention.

If desired, the engagement system of FIGS. 21A and 21B may be electronically activated and/or operated (e.g., by moving element 2116 under force applied via an electronic component rather than a mechanical lever) without departing from this invention.

While FIGS. 20 through 21B illustrate examples of mechanical securing and release systems, this is not a requirement. FIGS. 22A and 22B illustrate an example footwear system 2200 in which an electronic securing and release system is utilized. The system 2200 includes an electronic module 2202 mounted in a housing member 2204, e.g., in the various manners described above. The electronic module 2202 of this example structure 2200 includes grooves, recesses, openings, or discontinuities 2202a along one or more of its side surfaces that, as will be described below, are used for securing the module 2202 in the housing 2204. In this illustrated example structure 2200, insertion of the electronic module 2202 in the housing 2204 will cause an interaction with a switch mechanism 2206 (e.g., a mechanical switch, an electronic sensor, etc.), which in turn sends a signal to a processing system 2208. In response to this signal, processing system 2208 sends signals to electronically activated (e.g., and movable) retaining members 2210 to move inward to engage the grooves, recesses, openings, or discontinuities 2202a of the electronic module 2202. This action securely engages the electronic module 2202 in the housing 2204. If desired, the retaining members 2210 may form a part of the housing 2204 and/or may extend through openings provided in the housing 2204.

To release the module 2202 from the housing 2204, again a release tool 2212 may be used (e.g., inserted through an opening 2214), in the general manner described above. Insertion of the release tool 2212, in this example structure 2200, in some manner triggers a switch or otherwise activates a processing system (e.g., system 2208) to send a signal to the electronically activated (e.g., and movable) retaining members 2210 to retract from the grooves, recesses, openings, or discontinuities 2202a to thereby release the electronic module 2202. If necessary or desired, one or more spring elements 2216 or other structures may be provided (e.g., inside the housing 2204, extending through openings provided in the housing 2204, etc.) to help push the electronic module 2202 out of the housing 2204.

Figure 23:
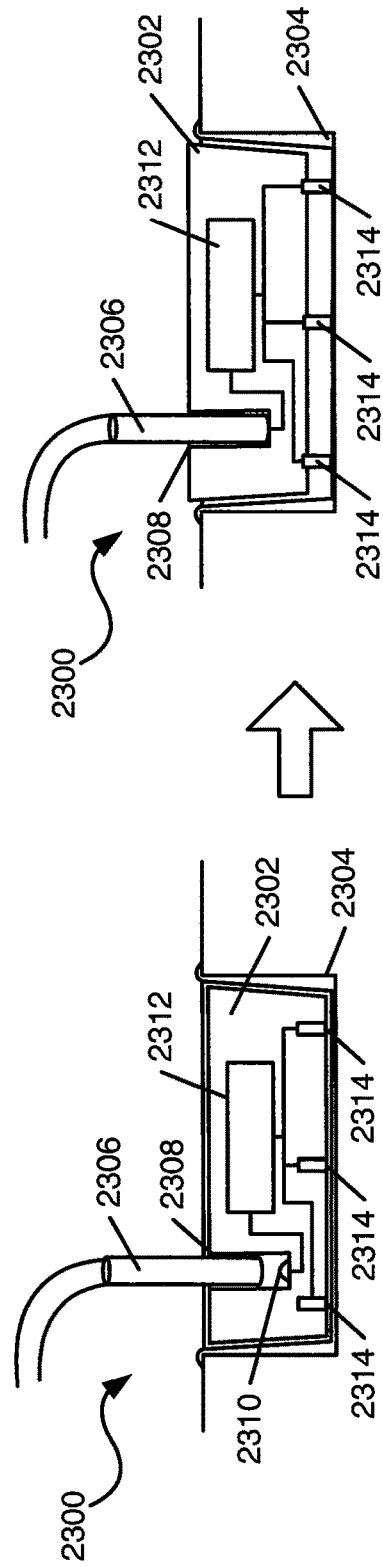

FIG. 23 illustrates another example structure 2300 including securing and/or releasing mechanisms that may be used in accordance with examples of the invention. In this example structure 2300, the module 2302 is mounted in a housing 2304 and may be secured therein in any desired manner (e.g., by friction fit, by detent structures, by retaining elements, and/or by any of the various structures described above). In this structure 2300, when release of the module 2302 is desired, a release tool 2306 is inserted into an opening 2308 provided in the module 2302 to activate a switch or other interaction mechanism 2310. Interaction between the tool 2306 and the switch 2310 sends a signal to a processing system 2312 (in this illustrated example on board the module 2302, but not a requirement), which in turn sends release signals to one or more engaging elements 2314 provided in or on the module 2302. As shown by the progression in FIG. 23, this action causes the engaging elements 2314 to extend outward and downward from the bottom of the module 2302, against the bottom of the housing 2304, to thereby move the module 2302 upward with respect to the housing 2304. Raising the module 2302 upward in this manner allows the user to more easily grasp it and thereby completely remove it from the housing 2304 and/or releases it from its tight fit or from any retaining structures to thereby allow it to fall out of the housing 2304, e.g., when shaken and/or under the force of gravity.

Of course, any number of engaging elements 2314, at any desired positions, may be provided without departing from the invention. Also, if desired, a mechanically activated and/or operated system may be provided (including various structures such as lever arms, fulcrum elements, and the like, as described above), rather than the electronically activated and operated system 2300 described above.

Figure 24:
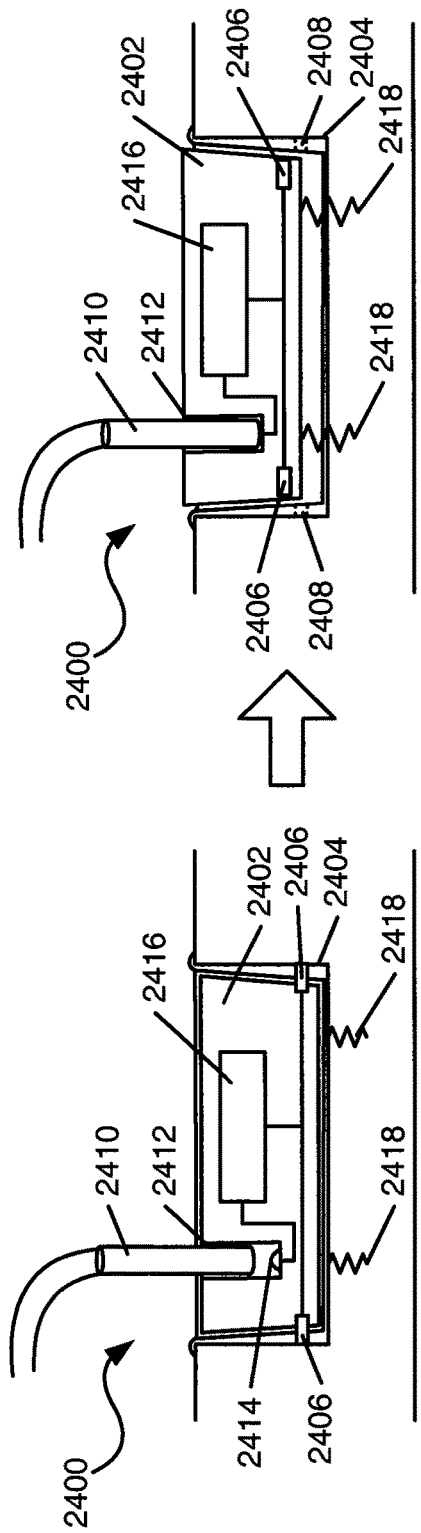

FIG. 24 illustrates another example structure 2400 that includes various securing and/or releasing mechanisms. In this example structure 2400, the module 2402 is mounted in a housing 2404 and held therein by retaining elements 2406 that extend out from the module 2402 into recesses or openings 2408 provided in the housing 2404 wall. Any desired manner of engaging the retaining elements 2406 in the openings 2408 may be used without departing from the invention. For example, if desired, the retaining elements 2406 may be spring loaded such that they slide inside the module 2402 against the biasing force of a spring while insertion of the module 2402 into the housing 2404 is taking place until they reach the openings 2408, at which point they automatically extend outward under the biasing force. As another example, if desired, an activation tool 2410 may be used once the module 2402 is properly inserted into the housing 2404 to then electronically activate the retaining elements 2406 and force them outward into the openings 2408. Other ways of making this engagement between the retaining elements 2406 and the openings 2408 may be used without departing from this invention. Of course, any number of retaining elements 2406 and openings 2408 may be provided, at any desired locations, without departing from this invention.

In this structure 2400, when release of the module 2402 is desired, a release tool 2410 is inserted into an opening 2412 provided in the module 2402 to activate a switch or other interaction mechanism 2414. Interaction between the tool 2410 and the switch 2414 sends a signal to a processing system 2416 (in this illustrated example on board the module 2402, but not a requirement), which in turn sends release signals to the retaining elements 2406. As shown by the progression in FIG. 24, this action causes the retaining elements 2406 to retract back into the module 2402 and out of the openings 2408 in the housing 2404, to thereby release the module 2402 (this same tool 2410 and system may be used to secure the retaining elements 2406 in the openings 2408, as described above). Once released, the module 2402 may be raised upward, e.g., under the force of spring members 2418, which in turn allows the user to more easily grasp it and thereby completely remove it from the housing 2404. Alternatively, release of the retaining elements 2406 from openings 2408 may be sufficient to simply allow the module 2402 to release from the housing 2404 under the force of gravity (e.g., fall out when shaken and/or turned upside-down).

Of course, if desired, a mechanically activated and/or operated system may be provided (including various structures such as lever arms, fulcrum elements, and the like, as described above), rather than the electronically activated and operated system 2400 described above.

A wide variety of different structures and arrangements for mechanically, electronically, and/or electromechanically securing and/or releasing an electronic module in a housing may be used without departing from the invention. Moreover, any number, structure, and/or arrangement of retaining elements and/or grooves, recesses, openings, and/or discontinuities may be used without departing from this invention.

As another alternative, if desired, rather than release tools as shown in FIGS. 20 through 24, if desired, the footwear structure could simply be structured to include a button or other activation system integrally formed, e.g., in the sole structure, so as to avoid the need for a separate release tool.

Other features may be available in footwear and performance sensing systems and methods according to this invention. For example, a single electronic module might be useful in a wide variety of different types of shoes, such as running shoes (e.g., to measure and provide data and information relating to speed, distance, time, etc., optionally based on GPS information); walking shoes (e.g., to measure and provide data and information relating to speed, distance, time, etc., optionally based on GPS or pedometer based information); basketball shoes (e.g., to measure and provide data relating to jump height, playing time, etc.); golf shoes (e.g., to measure yardage, distance traveled, etc.); etc. The manner in which the electronic module engages with the article of footwear may be used to provide information, for example, for use in activation, authentication, data processing algorithm selection, and the like.

FIGS. 25A and 25B illustrate examples. FIG. 25A shows an example portion of an area of engagement between an electronic module 2502 and a housing element 2504 provided in an article of footwear of a first type (e.g., a basketball sneaker). The electronic module 2502 and housing element 2504 may be of any desired construction or arrangement, including any of the various structures and arrangements described above. In this example structure 2500, the housing member 2504 includes an engaging surface 2506 that engages a corresponding engaging surface 2508 provided on the electronic module 2502. In this example structure 2500, the electronic module 2502 (which may be used in a variety of different types of footwear or for a variety of different sensing, monitoring, data transmission, and/or data reception purposes) includes five contact pads 2508a through 2508e. These contact pads 2508a through 2508e engage one or more contact pads provided on the engagement surface 2506 of the housing member 2504. In this illustrated example, the housing member 2504 includes four contact pads 2506a, 2506b, 2506c, and 2506e arranged to engage contact pads 2508a, 2508b, 2508c, and 2508e of the electronic module 2502. Notably, no contact pad is provided in the housing member 2504 corresponding to the location of contact pad 2508d. Therefore, when the electronic module 2502 engages the housing 2504 and contact is made between surfaces 2506 and 2508, a processing system, e.g., provided on board the module 2502 or included with the footwear, can sense electrical contact through pads 2508a, 2508b, 2508c, and 2508e and no electrical contact through pad 2508d (e.g., akin to a binary number 11101).

FIG. 25B shows an arrangement 2550 wherein the same electronic module 2502 as used in FIG. 25A is mounted in a housing member 2552 of a different type of shoe (e.g., a walking shoe or golf shoe). In this illustrated example, the housing member 2552 includes three contact pads on its contact surface 2554, namely contact pads 2554a, 2554c, and 2554d, which are arranged to engage with contact pads 2508a, 2508c, and 2508d of the electronic module 2502. Notably, no contact pads are provided in the housing member 2554 corresponding to the locations of contact pads 2508b and 2508e. Therefore, when the electronic module 2502 engages the housing 2554 and contact is made between surfaces 2554 and 2508, a processing system, e.g., provided on board the module 2502 or included with the article of footwear, can sense electrical contact through pads 2508a, 2508c, and 2508d and no electrical contact through pads 2508b and 2508e (e.g., akin to a binary number 10110).

A great deal of information can be provided through the differences in the electrical contact, e.g., of the types described in conjunction with FIGS. 25A and 25B. For example, as described above, each type of footwear by a specific manufacturer (or a group of manufacturers) may include a different type of contact pad pattern (e.g., zero or more of contact elements 2506a through 2506e). Utilizing these patterns of contact information, a processing system (e.g., on board the electronic module 2502 or elsewhere) can determine the type of footwear to which the electronic module 2502 is attached (e.g., based on the binary value of the contact pattern). The contact pattern also could convey other information, such as whether the module 2502 is mounted in the left shoe or the right shoe. This information, in turn, may be used by the electronic module 2502 for a variety of different purposes, e.g., to determine what data processing algorithm to utilize (e.g., for golf and/or measuring walking distance v. for basketball and measuring jump height); to determine which sensors to activate; to determine data polling frequency; to determine the type of data to transmit to a remote device, e.g., for display to the user, further processing, etc.; the manner, format, and/or protocol by which data is transmitted; and the like. In this manner, a single electronic module 2502 can be obtained and used in a wide variety of different shoe structures by a user for a wide variety of different measurement purposes, etc.

Of course, other ways of providing electrical contact, e.g., including this type of predetermined pattern or framework, may be used without departing from this invention. For example, if desired, the various contact pads may be provided on a variety of different surfaces of the housing member and/or electronic module (e.g., one or more of the top surface, the bottom surface, the side surface(s), engagement surface(s), etc.). As another example, if desired, the contact members may be provided through a series of extending elements or pins provided on the housing and/or module that extend into one or more corresponding recesses or openings provided in the other member (wherein contacts are provided in the openings or recesses). As still another example, if desired, a full set of contact members may be provided on the housing member as well as on the electronic module, and processing capabilities associated with the article of footwear and the module may be relied upon to provide predetermined activation and/or authentication information, e.g., to assure that the electronic module is authorized for use with a particular article of footwear (e.g., if desired, connection between the electronic module and the housing member may initiate transmission of a password or other authentication information, a user may be prompted to enter a password, a user may actively initiate the activation/ authentication processes, and the processing system then may be used to determine whether the electronic module and article of footwear are authorized for use with one another (e.g., by confirming use of the correct password, etc.)). If desired, the password and/or authentication signal may be encrypted in some manner to prevent unauthorized articles of footwear and/or modules from operating with one another. Other activation restriction and/or authentication systems and methods may be used without departing from this invention.

Figure 26:
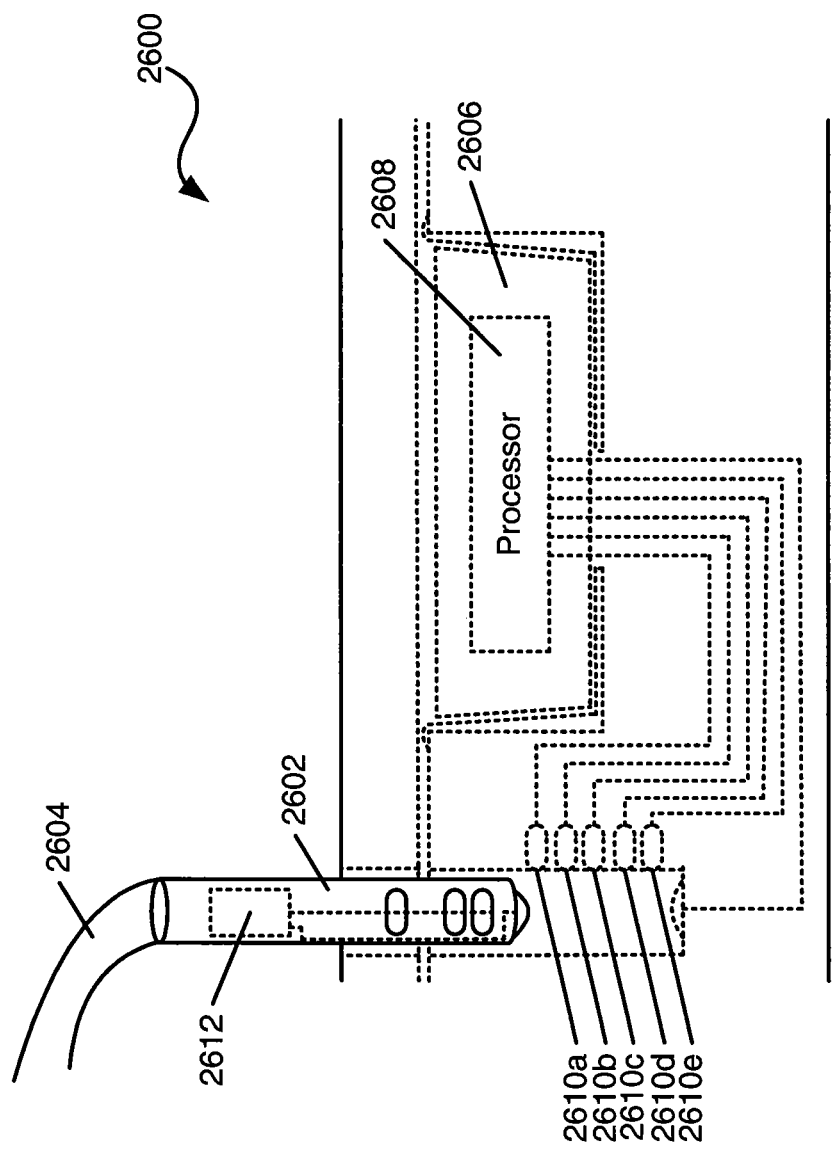

FIG. 26 illustrates another example system 2600 that has activation and/or authentication capabilities. Various example structures described above include a tool used for various purposes, e.g., to activate a securing system, to activate a release system, etc. A similar tool (or optionally, the same physical tool, such as the aglet 2602 for a shoelace 2604) may be used for activating an electronic module 2606 and/or some other portion of the overall system 2600, such as a processing system 2608 on board the article of footwear and/or included in the electronic module 2606 (e.g., by having the tool 2602 press an activation button, by having the tool 2602 initiate or complete electrical contact between various components, by having the tool 2602 in some manner initiate the production of a binary signal (e.g., due to initiation or completion of electrical contact between components, etc.), and the like).

As still another example, if desired, the activation tool 2602 (which also may be used for securing, releasing, and the like) also may be used to provide authentication and/or data algorithm selection information to the electronic module 2606. FIG. 26 illustrates an example of such an arrangement 2600. In this example structure 2600, the interior of the shoe includes contact members 2610a through 2610e that interconnect to the electronic module 2606 (e.g., via one or more of the various connection methods described above). The activation tool 2602 includes zero or more contact pads or elements (e.g., 2606b, 2606d, and 2606e in this illustrated example), which connect with the corresponding contact members 2610b, 2610d, and 2610e in the shoe structure. Notably, no contact pads are provided in the activation tool 2602 corresponding to the locations of contact pads 2610a and 2610c. Therefore, when the activation tool 2602 is inserted into the opening of the shoe, contact is made between the corresponding pads, and a processing system 2608, e.g., provided on board the module 2606 or with the shoe, can sense electrical contact through pads 2610b, 2610d, and 2610e and no electrical contact through pads 2610a and 2610c (e.g., akin to a binary number 01011). If desired, a user-activated or automatic switch, trigger system, or processing system 2612 (e.g., on board the tool 2602 or on board the shoe, such as at the bottom of the tool-receiving opening) may be used to initiate flow of electricity to the various contact pads 2606b, 2606d, and 2606e once the activation tool 2602 is fully inserted into the opening (e.g., so that any contact made between pads 2606 and 2610 during the course of tool insertion does not erroneously send information to the processor 2608).

Of course, a wide variety in the parts, structure, and arrangement of elements may be provided to the example system illustrated in FIG. 26 without departing from the invention. For example, if desired, the activation tool 2602 may be inserted into an appropriate opening provided directly in the electronic module 2606 rather than in a portion of the shoe structure (e.g., if desired, contact members 2610a through 2610e may be provided in or as part of the electronic module 2606). Also, an activation tool of the type illustrated in FIG. 26 may be used to provide any desired type of information, including the various information described above with reference to FIGS. 25A and 25B (e.g., authentication information, footwear style or type information, left foot/right foot information, data algorithm selection information, data transmission/reception/display information, data transmission/reception/display format information, etc.).

In view of their ability to receive data and information in accordance with at least some examples of this invention, e.g., in the various manners described above, the electronic modules also may be programmed, e.g., to produce or display specific user desired data or information; to activate selected sensors; to receive input for engagement, release, activation, authentication, and/or other purposes; etc. This input feature may be used for other purposes as well. For example, the electronic module may receive input allowing it to automatically detect different communication protocols and thereby address its communications (transmissions, receptions, etc.) appropriately. In this manner, the module could be designed to automatically receive and communicate in any number of different standard and/or non-standard protocols, such as the BodyLan protocol, the Bluetooth protocol (available from Bluetooth Sig Inc., of Belleview, Washington), Wifi protocols, RFID protocols, cellular telephone protocols, UDP broadcast protocols, TCP/IP broadcast protocols, other broadcast protocols, internet protocols, etc.

Moreover, as described above, different triggers could be used to trigger different communication protocols and/or data processing algorithms (e.g., optionally automatically when the module is snapped into certain shoes: for running shoes—it may initiate a running profile, for training shoes—it may initiate a gym/workout profile, for basketball shoes—it may sense vertical leap, etc.). Additionally or alternatively, if desired, different communication protocols and/or data processing algorithms may be triggered depending, for example, on the type of activity being sensed by the module (e.g., different communication protocols and/or data processing algorithms can be triggered based on certain detected types of motions or activity: running versus spinning, running outdoors versus on a treadmill, running versus jumping, etc.). As still another example, the location of use (e.g., based on data received via wireless communication with the module from a remote source) could trigger different communication protocols and/or data processing algorithms (e.g., when a user walks into his/her gym, the system may communicate on one type of communication protocol and/or use one data processing algorithm, but when they walk into a retail store, it may communicate on another communication protocol and/or use another data processing algorithm, and/or when they run outdoors, it may communicate on yet another communication protocol and/or use another data processing algorithm, etc.).

As still additional examples, if desired, the electronic module may be used to communicate with (e.g., provide data or information to and/or receive data and information from) other peer devices (e.g., other users of footwear including electronic modules of the types described above), either directly in a peer-to-peer manner and/or through another intermediate or remote device (e.g., a remote device 314 with which plural modules communicate). This feature may allow one athlete or other user (such as a coach, trainer, etc.) to track the progress of others, provide information to others, etc.

E. Other Devices and/or Features

Figure 27:
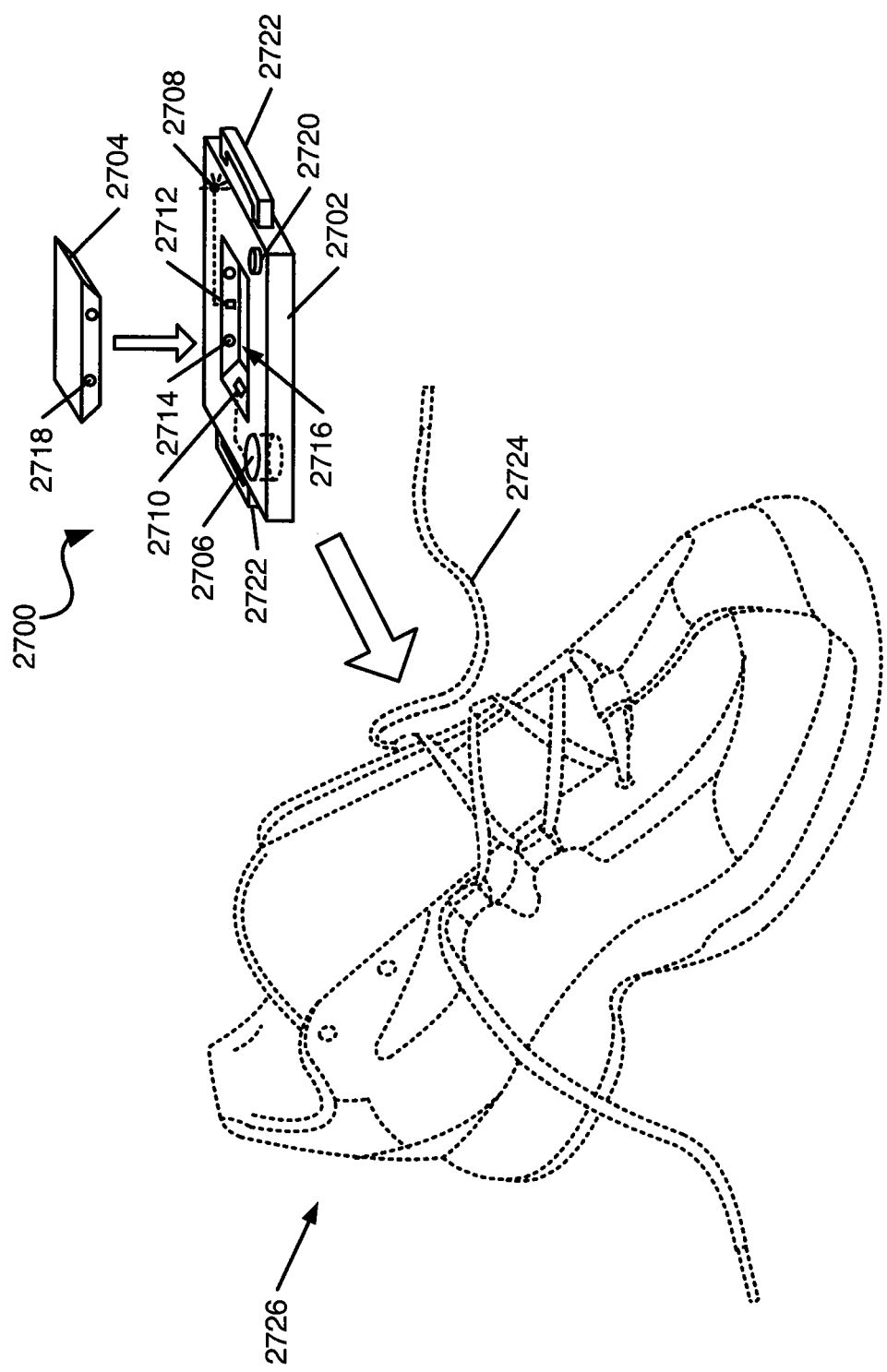
FIGS. 27 and 28 illustrate various example features and structures for a universal housing member that may be provided in accordance with examples of this invention.

The above description focuses primarily on articles of footwear that include one or more housings or other structures integrally formed therewith for holding an electronic module, e.g., for sensing one or more characteristics of an athletic performance, for measuring one or more physical or physiological parameters associated with use of the article of footwear, etc. Not all aspects of this invention relate to footwear integrated systems. FIG. 27 illustrates an example system 2700 including a "universal" housing member 2702 to which an electronic module 2704 may be mounted. The electronic module 2704 may provide and/or receive any desired type of information, including the various types of information described above. Moreover, the universal housing member 2702 may provide any desired functionality and/or structures, including, for example, the various functions and structures described for inclusion in the various housings and/or footwear structures described above. In this illustrated example, the housing member 2702 includes a power source 2706 (e.g., a battery) that can provide power to any components in the housing member 2702 (such as a data transmission/reception system 2708 (e.g., antenna, transmission/reception components, etc.), as well as power to any electronic components provided in the electronic module 2704 (e.g., via electrical contact member 2710 between the housing 2702 and the module 2704), if desired. Also, the universal housing member 2702 may include data processing capabilities and/or data processing capabilities may be provided on board the electronic module 2704. In this illustrated example structure 2700, data for transmission to a remote device is transmitted from the electronic module 2704 to the data transmission/reception system 2708 via an electrical contact 2712 between the module 2704 and the housing member 2702.

While any desired manner of connecting the electronic module 2704 with the housing member 2702 may be provided without departing from this invention, in this illustrated example, the housing member 2702 includes spring-loaded ball elements 2714 that extend around the perimeter of and somewhat into the opening 2716 into which the module 2704 is mounted. The module 2704, on the other hand, includes small recesses or detents 2718 into which the ball elements 2714 extend under the spring biasing force. Such engagement mechanisms are commercially available. In this manner, the module 2704 can be snapped into place by pushing it into the opening 2716, which forces the balls 2714 back against the spring force until they align with the corresponding recesses 2718. One or more release buttons 2720 may be provided to relax the spring force and enable the module to be easily slid back out of the opening 2716. If desired, electrical contact also could be made between the housing 2702 and the module 2704 at these ball 2714 and receptacle 2718 structures (or via other present securing structures), rather than providing separate contact areas 2710 and 2712.

Of course, any desired manner of engaging and securing the module and a universal housing, making electrical contact between the module and housing (if necessary), providing activation and/or authentication information, and/or releasing the module from the housing may be used without departing from this invention, including any of the various systems and methods described above with respect to the footwear based systems.

Also, any desired manner of connecting the universal housing 2700 to another object may be used, if desired, without departing from this invention. The illustrated example structure 2700 includes plural engagement openings 2722 that enable the housing 2700 to be releasably attached to a relatively long, thin element, like a shoelace 2724, a strap provided on an upper member of a shoe 2726 (e.g., on its tongue, instep, sides, sole, etc.) or other device, or a belt or other strap member 2804 (see FIG. 28). As additional or alternative examples, if desired, the universal housing 2700 may include a clamp or clip member (e.g., optionally spring biased) integrally formed therewith and/or engaged therewith, to allow it to be easily attached to another object (akin to carrying and securing members for cellular telephones and the like); it may include a hook-and-loop fastener or other mechanical fastener arrangement; it may be attached to another object by an adhesive; etc. Other holding and/or securing systems also may be used without departing from the invention, such as straps or other systems for carrying and handling electronic devices that are known and used in the art.

Figure 28:
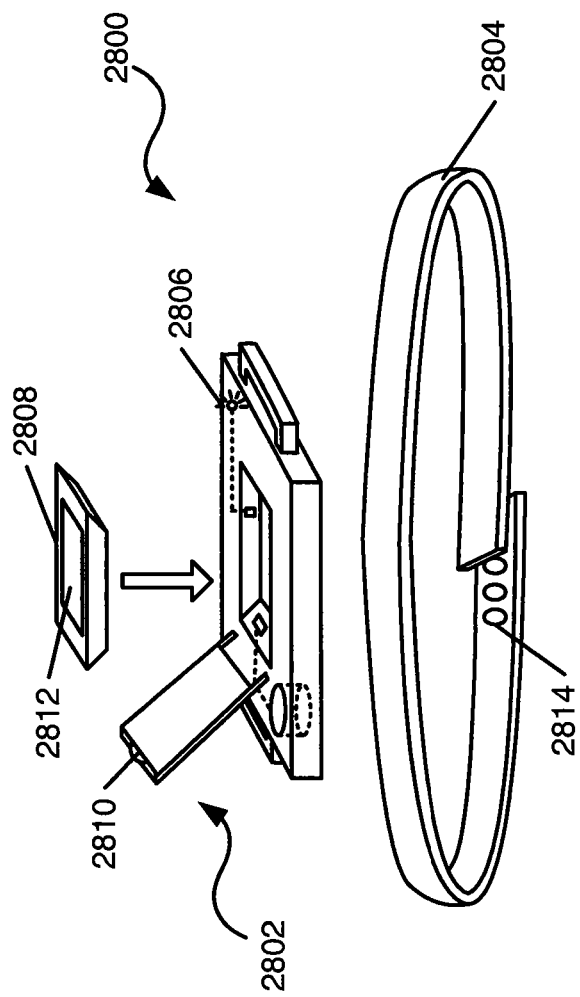

FIG. 28 illustrates another example structure 2800, as noted above, in which a universal housing member 2802, including a housing device 2806 and an electronic module 2808 are mounted to a strap member 2804. In this example structure 2800, the module 2808 is secured to the housing device 2806 using a cover element 2810. If desired, the cover element 2810 may be relatively transparent, e.g., to allow users to view the module 2808, should the module include any type of video or alphanumeric display 2812. The cover element 2810 may be secured, e.g., to the housing device 2806 and/or the module 2808, in a wide variety of different manners, including, for example, the manner in which covers for battery compartments are held in place in conventional electronic devices, such as games, cameras, video or audio recorders, or the like. Of course, a wide variety of systems may be used to hold the module 2808 in the housing 2806, including any of the various types of systems described above (e.g., cover element 2810 may be provided simply to protect display 2812). Additionally, the housing member 2802 may be engaged with the band 2804 in any desired manner, including, for example, the manners in which watches or other wrist-borne elements are formed or engaged with their corresponding bands. Additionally, any desired type of band 2804 may be used, with any desired type(s) of securing structures, such as stretchable bands, bands with buckle systems, bands with hook-and-loop fastener systems 2814, etc. The band 2804 may be used to attach the overall system 2800 to any desired object, such as a wearer's arm, ankle, or neck; a shoe or article of clothing; a piece of athletic equipment; another piece of equipment (e.g., something carried by the athlete); etc.

Still other examples of systems including electronic modules of the types described above (e.g., for sensing one or more characteristics of an athletic performance, for sensing one or more physical or physiological parameter(s), etc.) are possible without departing from the invention. For example, rather than including the module as part of a pair of shoes, it may be included in and/or mounted on a pair of socks or other foot-receiving devices (optionally using a universal housing member of the types described above). For socks, the module (optionally with one of the universal housing members described above) may be mounted in a pocket provided, for example, in the lateral or medial ankle side of the sock, along the top, foot-receiving opening of the sock, etc. Other host devices for carrying the module (optionally with one of the universal housing members described above) also are possible.

III. CONCLUSION

While the invention has been described with respect to specific examples including presently preferred modes of carrying out the invention, those skilled in the art will appreciate that there are numerous variations and permutations of the above described systems and methods. For example various aspects of the invention may be used in different combinations and various different subcombinations of aspects of the invention may be used together in a single system or method without departing from the invention. Also, various method steps described above may be changed, changed in order, omitted, and/or additional steps may be added without departing from this invention. Thus, the invention should be construed broadly as set forth in the appended claims.

We claim:

1. A performance sensing system, comprising:
an electronic module configured to provide data relating to at least one physical or physiological parameter associated with a performance;
a housing member configured to mount the electronic module thereto and to provide power to the electronic module when mounted thereto;
an electronic module securement system configured to releasably secure the electronic module to the housing member; and
a housing member securement system configured to releasably secure the housing member to a wearable article,
wherein the electronic module securement system includes a plurality of spring-loaded elements extending around at least a portion of a perimeter of an opening in the housing member, and wherein the opening is configured to receive the electronic module, and
wherein the electronic module securement system includes a plurality of recesses extending around at least a portion of a perimeter of the electronic module, and wherein each of the plurality of recesses is configured to receive a respective spring-loaded element that extends therein under a spring biasing force when the electronic module is mounted to the housing member.

2. The performance sensing system according to claim 1, wherein the housing member includes a power source configured to provide power to the electronic module via an electrical contact member in the housing member positioned to contact the electronic module.

3. The performance sensing system according to claim 1, wherein the plurality of spring-loaded elements and the plurality of recesses create an electrical contact between the electronic module and the housing member.

4. The performance sensing system according to claim 1, wherein the housing member includes:
a data transmission system configured to transmit data relating to the physical or physiological parameters from the electronic module to a remote device.

5. The performance sensing system according to claim 4, wherein the electronic module is in electrical communication with the data transmission system via the housing member.

6. The performance sensing system according to claim 4, wherein the remote device is remote from the housing member and the data transmission system includes a wireless transmission system.

7. The performance sensing system according to claim 6, wherein the housing member securement system includes a clamp or clip member integrally formed with the housing member or engaged with the housing member.

8. The performance sensing system according to claim 6, wherein the electronic module includes a display device configured to display at least data relating to the physical or physiological parameters.

9. The performance sensing system according to claim 1, wherein the electronic module securement system includes a release mechanism configured to enable removal of the electronic module from the housing member upon a user interaction with the release mechanism.

10. The performance sensing system according to claim 1, wherein the housing member securement system includes an engagement opening configured to enable the housing members to be releasably attached to a strap of the wearable article.

11. The performance sensing system according to claim 1, wherein the electronic module provides data relating to at least one of location, movement speed, or movement distance.

12. The performance sensing system according to claim 1, wherein the electronic module securement system includes a cover element engaged with the housing member, and wherein the cover element extends across an electronic module receiving chamber of the housing member.

13. An apparatus, comprising:
an electronic module configured to sense and record data relating to at least one physical or physiological parameter associated with a performance; and
a housing member including:
an electronic module receiving chamber configured to receive the electronic module therein;
an electrical contact component configured to provide power to the electronic module when mounted in the housing member; and
a securement system configured to releasably secure the electronic module in the housing member and to attach the housing member to a wearable article,
wherein the securement system includes a plurality of spring-loaded elements extending around at least a portion of a perimeter of an opening in the housing member and wherein the opening is configured to receive the electronic module, and
wherein the securement system includes a plurality of recesses extending around at least a portion of a perimeter of the electronic module, and wherein each of the plurality of recesses is configured to receive a respective spring-loaded element that extends therein under a spring biasing force when the electronic module is mounted to the housing member.

14. The apparatus according to claim 13, wherein the securement system includes a retaining device engaged with the housing member that extends at least partially across the electronic module receiving chamber.

15. The apparatus according to claim 13, wherein the securement system includes a fastener for holding the electronic module in place in the housing member.

16. The apparatus according to claim 13, wherein the securement system includes a member that extends into a recess, opening, or groove defined in the electronic module so as to secure the electronic module in the housing member.

17. The apparatus according to claim 13, wherein the securement system includes a belt, band, or lace member engaged with the housing member configured to attach to an article or to a portion of a user body.

18. An apparatus, comprising:
a housing member configured to releasably secure an electronic module thereto and to provide power to the electronic module when mounted thereto, wherein the electronic module is configured to provide data relating to at least one physical or physiological parameter associated with a performance; and a housing member securement system configured to releasably secure the housing member to a wearable article, wherein the housing member securement system includes a plurality of spring-loaded elements extending around at least a portion of a perimeter of an opening in the housing member, and wherein the opening is configured to receive the electronic module, and wherein the housing member securement system includes a plurality of recesses extending around at least a portion of a perimeter of the electronic module, and wherein each of the plurality of recesses is configured to receive a respective spring-loaded element that extends therein under a spring biasing force when the electronic module is mounted to the housing member.

* * * * *